US011702469B2

(12) United States Patent
Dorrance et al.

(10) Patent No.: US 11,702,469 B2
(45) Date of Patent: Jul. 18, 2023

(54) RECOMBINANT EGFL7, EGFL7 ANTIBODIES, AND USES THEREOF

(71) Applicant: Ohio State Innovation Foundation, Columbus, OH (US)

(72) Inventors: Adrienne M. Dorrance, Columbus, OH (US); Ramiro Garzon, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 482 days.

(21) Appl. No.: 16/607,930

(22) PCT Filed: Apr. 24, 2018

(86) PCT No.: PCT/US2018/029059
§ 371 (c)(1),
(2) Date: Oct. 24, 2019

(87) PCT Pub. No.: WO2018/200465
PCT Pub. Date: Nov. 1, 2018

(65) Prior Publication Data
US 2020/0277363 A1 Sep. 3, 2020

Related U.S. Application Data

(60) Provisional application No. 62/489,015, filed on Apr. 24, 2017.

(51) Int. Cl.
| | |
|---|---|
| C07K 16/22 | (2006.01) |
| A61P 35/02 | (2006.01) |
| C12N 15/113 | (2010.01) |
| A61K 31/5377 | (2006.01) |
| A61K 45/06 | (2006.01) |
| A61K 39/395 | (2006.01) |
| C12N 5/0789 | (2010.01) |
| A61K 39/00 | (2006.01) |

(52) U.S. Cl.
CPC .............. *C07K 16/22* (2013.01); *A61P 35/02* (2018.01); *C12N 5/0647* (2013.01); *C12N 15/113* (2013.01); *A61K 31/5377* (2013.01); *A61K 39/395* (2013.01); *A61K 45/06* (2013.01); *A61K 2039/505* (2013.01); *C12N 2310/113* (2013.01)

(58) Field of Classification Search
CPC .......... C07K 16/22; A61P 35/02; A61P 35/00; A61K 31/5377; A61K 45/06; A61K 31/136; A61K 31/4745; A61K 31/475; A61K 31/704; A61K 31/7048; A61K 31/7068; A61K 31/7076; A61K 39/395; C12N 2310/113; C12N 5/0647; C12N 15/113
See application file for complete search history.

(56) References Cited

U.S. PATENT DOCUMENTS

| | | | |
|---|---|---|---|
| 8,398,976 | B2 | 3/2013 | Ye et al. |
| 8,574,576 | B2 | 11/2013 | Ye et al. |
| 2010/0203041 | A1 | 8/2010 | Ye et al. |
| 2010/0285009 | A1 | 11/2010 | Ye et al. |
| 2013/0004498 | A1 | 1/2013 | Bai et al. |
| 2013/0129733 | A1 | 5/2013 | Ye et al. |
| 2013/0129735 | A1* | 5/2013 | Ye .......................... A61P 27/00 424/136.1 |
| 2013/0129749 | A1 | 5/2013 | Ye et al. |
| 2013/0149307 | A1 | 6/2013 | Ye et al. |
| 2013/0287779 | A1 | 10/2013 | Ye et al. |
| 2013/0324704 | A1 | 12/2013 | Ye et al. |
| 2014/0051120 | A1 | 2/2014 | Ye et al. |
| 2014/0286955 | A1 | 9/2014 | Aifantis et al. |
| 2015/0071855 | A1 | 3/2015 | Lewis et al. |

FOREIGN PATENT DOCUMENTS

| | | |
|---|---|---|
| EP | 2468772 | 6/2012 |
| WO | 2005117968 | 12/2005 |
| WO | 2007106915 | 9/2007 |
| WO | 2010129904 | 11/2010 |
| WO | 2012009705 | 1/2012 |
| WO | 2012106473 | 8/2012 |
| WO | 2012109624 | 8/2012 |
| WO | 2012162561 | 11/2012 |
| WO | 2013142961 | 10/2013 |
| WO | 2014028776 | 2/2014 |
| WO | 2014144600 | 9/2014 |

OTHER PUBLICATIONS

Garcia-Carbonero R, et al. Randomized Phase II Trial of Parsatuzumab (Anti-EGFL7) or Placebo in Combination with FOLFOX and Bevacizumab for First-Line Metastatic Colorectal Cancer. Oncologist. Apr. 2017;22(4):375-e30. (Year: 2017).*
Hong G, Kuek V, Shi J, Zhou L, Han X, He W, Tickner J, Qiu H, Wei Q, Xu J. EGFL7: Master regulator of cancer pathogenesis, angiogenesis and an emerging mediator of bone homeostasis. J Cell Physiol. Nov. 2018;233(11):8526-8537. doi: 10.1002/jcp.26792. Epub Jun. 19, 2018. PMID: 29923200. (Year: 2018).*
Johnson L, Huseni M, Smyczek T, et al. Anti-EGFL7 antibodies enhance stress-induced endothelial cell death and anti-VEGF efficacy. J Clin Invest. 2013;123(9):3997-4009. doi:10.1172/JCI67892 (Year: 2013).*
NCI, "parsatuzumab", Dictionary of Cancer Terms (Year: 2022).*
NCI, "antiangiogenesis agent", Dictionary of Cancer Terms (Year: 2022).*
Edwards et al. 2003. The remarkable flexibility of the human antibody repertoire; isolation of over one thousand different antibodies to a single protein, BlyS. Journal of Molecular Biology 334:103-118 (Year: 2003).*

(Continued)

*Primary Examiner* — Hong Sang
*Assistant Examiner* — Sung Min Yoon
(74) *Attorney, Agent, or Firm* — Meunier Carlin & Curfman LLC

(57) ABSTRACT

The present disclosure relates to recombinant EGFL7, EGFL7 antibodies, and uses thereof.

8 Claims, 40 Drawing Sheets

Specification includes a Sequence Listing.

(56) References Cited

OTHER PUBLICATIONS

Trujillo A, McGee C, Cogle CR. Angiogenesis in acute myeloid leukemia and opportunities for novel therapies. J Oncol. 2012;2012:128608. doi: 10.1155/2012/128608. Epub Sep. 5, 2011. PMID: 21904549; PMCID: PMC3167188. (Year: 2011).*
Shen et al., EGFL7 Antagonizes NOTCH Signaling, Stimulates Blast Proliferation and Confers Poor Prognosis in Cytogenetically-Normal Acute Myeloid Leukemia (CN-AML). Blood 2016; 128 (22): 2689. doi: https://doi.org/10.1182/blood.V128.22.2689.2689 (Year: 2016).*
Lee LY, Hernandez D, Rajkhowa T, Smith SC, Raman JR, Nguyen B, Small D, Levis M. Preclinical studies of gilteritinib, a next-generation FLT3 inhibitor. Blood. Jan. 12, 2017;129(2):257-260. doi: 10.1182/blood-2016-10-745133. Epub Dec. 1, 2016. PMID: 27908881; PMCID: PMC5234222. (Year: 2016).*
International Search Report and Written Opinion issued by the International Searching Authority (ISA/US) in PCT Application No. PCT/US2018/029059 dated Oct. 4, 2018. 12 pages.
Garcia-Carbonero, Rocio, et al. "Randomized phase II trial of parsatuzumab (anti-EGFL7) or placebo in combination with FOLFOX and bevacizumab for first-line metastatic colorectal cancer." The oncologist 22.4 (2017): 375-e30.
Shen, Changxian, et al. "EGFL7 Antagonizes NOTCH Signaling, Stimulates Blast Proliferation and Confers Poor Prognosis in Cytogenetically-Normal Acute Myeloid Leukemia (CN-AML)." Blood. (2016) vol. 128, No. 22: 2689-2689.
Extended European Search Report and Opinion, issued by the European Patent Office in European Application No. 18791023.7 dated Dec. 18, 2020. 13 pages.
Nishida, Chiemi, et al. "Epidermal Growth Factor-like Domain 7 Promotes Hematopoietic Stem Cell Expansion and Increases Myeloid-Megakaryocytic Lineage Priming through beta3 Integrin." Blood. (2014): 2919-2919.
Pullarkat, Vinod A., and Edward M. Newman. "BCL2 inhibition by venetoclax: targeting the Achilles' heel of the acute myeloid leukemia stem cell? " Cancer discovery 6.10 (2016): 1082-1083.
Sun, Yanqin, et al. "miR-126 inhibits non-small cell lung cancer cells proliferation by targeting EGFL7." Biochemical and biophysical research communications 391.3 (2010): 1483-1489.
Bill, Marius, et al. "EGFL7 antagonizes NOTCH signaling and represents a novel therapeutic target in acute myeloid eukemia." Clinical Cancer Research 26.3 (2020): 669-678.
Acar, Ahmet, et al. "A role for notch signalling in breast cancer and endocrine resistance." Stem cells international 2016 (2016).
Anders, Simon, Paul Theodor Pyl, and Wolfgang Huber. "HTSeq—a Python framework to work with high-throughput sequencing data." Bioinformatics 31.2 (2015): 166-169.
Badiwala, Mitesh V., et al. "Epidermal growth factor-like domain 7 suppresses intercellular adhesion molecule 1 expression in response to hypoxia/reoxygenation injury in human coronary artery endothelial cells." Circulation 122.11_suppl_1 (2010):S156-S161.
Badiwala, Mitesh V., et al. "Epidermal Growth Factor-Like Domain 7 Is a Novel Inhibitor of Neutrophil Adhesion to Coronary Artery Endothelial Cells Injured by Calcineurin Inhibition." Circulation 124.11_suppl_1 (2011): S197-S203.
Baer, Maria R., et al. "Low-dose interleukin-2 immunotherapy does not improve outcome of patients age 60 years and older with acute myeloid leukemia in first complete remission: Cancer and Leukemia Group B Study 9720." Journal of clinical oncology 26.30 (2008): 4934.
Baer, Maria R., et al. "Phase 3 study of the multidrug resistance modulator PSC-833 in previously untreated patients 60 years of age and older with acute myeloid leukemia: Cancer and Leukemia Group B Study 9720." Blood, The Journal of the American Society of Hematology 100.4 (2002): 1224-1232.
Bambino, Kathryn, et al. "Epidermal growth factor-like domain 7 is a marker of the endothelial lineage and active angiogenesis." Genesis 52.7 (2014): 657-670.
Becker, Heiko, et al. "Favorable prognostic impact of NPM1 mutations in older patients with cytogenetically normal de novo acute myeloid leukemia and associated gene-and microRNA-expression signatures: a Cancer and Leukemia Group B study." Journal of clinical oncology 28.4 (2010): 596.
Blum, William, et al. "Maintenance therapy with decitabine in younger adults with acute myeloid leukemia in first remission: a phase 2 Cancer and Leukemia Group B Study (CALGB 10503)." Leukemia 31.1 (2017): 34-39.
Briot, Anais, Anne Bouloumié, and M. Luisa Iruela-Arispe. "Notch, lipids, and endothelial cells." Current opinion in lipidology 27.5 (2016): 513.
Cheson, Bruce D., et al. "Report of the National Cancer Institute-sponsored workshop on definitions of diagnosis and response in acute myeloid leukemia." Journal of Clinical Oncology 8.5 (1990): 813-819.
D'Souza, Brendan, Laurence Meloty-Kapella, and Gerry Weinmaster. "Canonical and non-canonical Notch ligands." Current topics in developmental biology. vol. 92. Academic Press, 2010. 73-129.
De Leeuw, David C., et al. "Attenuation of microRNA-126 expression that drives CD34+ 38− stem/progenitor cells in acute myeloid leukemia leads to tumor eradication." Cancer research 74.7 (2014): 2094-2105.
Dobin, Alexander, et al. "STAR: ultrafast universal RNA-seq aligner." Bioinformatics 29.1 (2013): 15-21.
Döhner, Hartmut, et al. "Diagnosis and management of AML in adults: 2017 ELN recommendations from an international expert panel." Blood 129.4 (2017): 424-447.
Dorrance, Adrienne M., et al. "Targeting leukemia stem cells in vivo with antagomiR-126 nanoparticles in acute myeloid leukemia." Leukemia 29.11 (2015) 2143-2153.
Dorrance, Adrienne M., et al. "The Rac GTPase effector p21-activated kinase is essential for hematopoietic stem/progenitor cell migration and engraftment." Blood, The Journal of the American Society of Hematology 121.13 (2013): 2474-2482.
Dufour, Annika, et al. "Acute myeloid leukemia with biallelic CEBPA gene mutations and normal karyotype represents a distinct genetic entity associated with a favorable clinical outcome." Journal of clinical oncology 28.4 (2010): 570-577.
Fan, Chun, et al. "The expression of Egfl7 in human normal tissues and epithelial tumors." The International journal of biological markers 28.1 (2013): 71-83.
Gandemer, Virginie, et al. "Five distinct biological processes and 14 differentially expressed genes characterize TEL/AML1-positive leukemia." BMC genomics 8.1 (2007): 385.
Garzon, Ramiro, et al. "Expression and prognostic impact of lncRNAs in acute myeloid leukemia." Proceedings of the National Academy of Sciences 111.52 (2014): 18679-18684.
Guinn, Daphne, et al. "The regulation of tumor-suppressive microRNA, miR-126, in chronic lymphocytic leukemia." Cancer medicine 6.4 (2017): 778-787.
Hannon, Maura M., et al. "Elevated TRIB 2 with NOTCH 1 activation in paediatric/adult T-ALL." British journal of haematology 158.5 (2012): 626-634.
Harrow, Jennifer, et al. "GENCODE: the reference human genome annotation for The Encode Project." Genome research 22.9 (2012): 1760-1774.
He, Qiuping, et al. "Inflammatory signaling regulates hematopoietic stem and progenitor cell emergence in vertebrates." Blood, The Journal of the American Society of Hematology 125.7 (2015): 1098-1106.
Heidel, Florian H., et al. "Evolutionarily conserved signaling pathways: acting in the shadows of acute myelogenous leukemia's genetic diversity." Clinical cancer research 21.2 (2015): 240-248.
Huang, Chun-hai, et al. "Expression and clinical significance of EGFL7 in malignant glioma." Journal of cancer research and clinical oncology 136.11 (2010): 1737-1743.
Johnson, Leisa, et al. "Anti-EGFL7 antibodies enhance stress-induced endothelial cell death and anti-VEGF efficacy." The Journal of clinical investigation 123.9 (2013): 3997-4009.
Kannan, Sankaranarayanan, et al. "Notch activation inhibits AML growth and survival: a potential therapeutic approach." Journal of Experimental Medicine 210.2 (2013): 321-337.

(56) References Cited

OTHER PUBLICATIONS

Kaplan, Edward L., and Paul Meier. "Nonparametric estimation from incomplete observations." Journal of the American statistical association 53.282 (1958): 457-481.
Kato, T., et al. "Hes1 suppresses acute myeloid leukemia development through FLT3 repression." Leukemia 29.3 (2015): 576-585.
Köhler, Georges, and Cesar Milstein. "Continuous cultures of fused cells secreting antibody of predefined specificity." nature 256.5517 (1975): 495-497.
Kolitz, Jonathan E., et al. "Dose escalation studies of cytarabine, daunorubicin, and etoposide with and without multidrug resistance modulation with PSC-833 in untreated adults with acute myeloid leukemia younger than 60 years: final induction results of Cancer and Leukemia Group B Study 9621." Journal of Clinical Oncology 22.21 (2004): 4290-4301.
Kolitz, Jonathan E., et al. "P-glycoprotein inhibition using valspodar (PSC-833) does not improve outcomes for patients younger than age 60 years with newly diagnosed acute myeloid leukemia: Cancer and Leukemia Group B study 19808." Blood, The Journal of the American Society of Hematology 116.9 (2010): 1413-1421.
Kroll, Karl W., et al. "MuCor: mutation aggregation and correlation." Bioinformatics 32.10 (2016): 1557-1558.
Lechman, Eric R., et al. "miR-126 regulates distinct self-renewal outcomes in normal and malignant hematopoietic stem cells." Cancer cell 29.2 (2016): 214-228.
Lee, Edward J., et al. "Parallel phase I studies of daunorubicin given with cytarabine and etoposide with or without the multidrug resistance modulator PSC-833 in previously untreated patients 60 years of age or older with acute myeloid leukemia: results of Cancer and Leukemia Group B study 9420." Journal of clinical oncology 17.9 (1999): 2831-2831.
Li, J. J., et al. "Prognostic role of epidermal growth factor-like domain 7 protein expression in laryngeal squamous cell carcinoma." The Journal of Laryngology & Otology 125.11 (2011): 1152-1157.
Li, Zejuan, et al. "Distinct microRNA expression profiles in acute myeloid leukemia with common translocations." Proceedings of the National Academy of Sciences 105.40 (2008): 15535-15540.
Lobry, Camille, et al. "Notch pathway activation targets AML-initiating cell homeostasis and differentiation." Journal of Experimental Medicine 210.2 (2013) 301-319.
Lobry, Camille, et al. "Notch signaling: switching an oncogene to a tumor suppressor." Blood, The Journal of the American Society of Hematology 123.16 (2014): 2451-2459.
Lu, Jie, et al. "Oncogenic role of the Notch pathway in primary liver cancer (Review) Corrigendum in/10.3892/ol. 2016.5145." Oncology letters 12.1 (2016): 3-10.
Luo, Bai-Hua, et al. "Epidermal Growth Factor-Like Domain-Containing Protein 7 (EGFL7) Enhances EGF Receptor—AKT Signaling, Epithelial—Mesenchymal Transition, and Metastasis of Gastric Cancer Cells." PLoS One 9.6 (2014).
Marcucci, G., et al. "A phase III randomized trial of intensive induction and consolidation chemotherapy±oblimersen, a pro-apoptotic Bcl-2 antisense oligonucleotide in untreated acute myeloid leukemia patients> 60 years old." Journal of Clinical Oncology 25.18_suppl (2007): 7012-7012.
Marcucci, Guido, et al. "Age-related prognostic impact of different types of DNMT3A mutations in adults with primary cytogenetically normal acute myeloid leukemia." Journal of clinical oncology 30.7 (2012): 742.
Marcucci, Guido, et al. "IDH1 and IDH2 gene mutations identify novel molecular subsets within de novo cytogenetically normal acute myeloid leukemia: a Cancer and Leukemia Group B study." Journal of clinical oncology 28.14 (2010): 2348.
Marcucci, Guido, et al. "MicroRNA expression in cytogenetically normal acute myeloid leukemia." New England Journal of Medicine 358.18 (2008): 1919-1928.
Marcucci, Guido, et al. "Prognostic significance of, and gene and microRNA expression signatures associated with, CEBPA mutations in cytogenetically normal acute myeloid leukemia with high-risk molecular features: a Cancer and Leukemia Group B Study." Journal of clinical oncology 26.31 (2008): 5078.
Massimiani, Micol, et al. "Epidermal growth factor-like domain 7 promotes migration and invasion of human trophoblast cells through activation of MAPK, PI3K and Notch signaling pathways." Mhr: Basic science of reproductive medicine 21.5 (2015): 435-451.
Mayer, Robert J., et al. "Intensive postremission chemotherapy in adults with acute myeloid leukemia." New England Journal of Medicine 331.14 (1994): 896-903.
Mendler, Jason H., et al. "RUNX1 mutations are associated with poor outcome in younger and older patients with cytogenetically normal acute myeloid leukemia and with distinct gene and MicroRNA expression signatures." Journal of clinical oncology 30.25 (2012): 3109.
Metzeler, Klaus H., et al. "ASXL1 mutations identify a high-risk subgroup of older patients with primary cytogenetically normal AML within the ELN Favorable genetic category." Blood, The Journal of the American Society of Hematology 118.26 (2011): 6920-6929.
Metzeler, Klaus H., et al. "TET2 mutations improve the new European LeukemiaNet risk classification of acute myeloid leukemia: a Cancer and Leukemia Group B study." Journal of clinical oncology 29.10 (2011): 1373.
Moore, Joseph O., et al. "Granulocyte colony-stimulating factor (filgrastim) accelerates granulocyte recovery after intensive postremission chemotherapy for acute myeloid leukemia with aziridinyl benzoquinone and mitoxantrone: Cancer and Leukemia Group B study 9022." Blood, The Journal of the American Society of Hematology 89.3 (1997): 780-788.
Moore, Joseph O., et al. "Sequential multiagent chemotherapy is not superior to high-dose cytarabine alone as postremission intensification therapy for acute myeloid leukemia in adults under 60 years of age: Cancer and Leukemia Group B Study 9222." Blood 105.9 (2005): 3420-3427.
Mrózek, Krzysztof, et al. "Central review of cytogenetics is necessary for cooperative group correlative and clinical studies of adult acute leukemia: the Cancer and Leukemia Group B experience." International journal of oncology 33.2 (2008): 239-244.
Nichol, Donna, and Heidi Stuhlmann. "EGFL7: a unique angiogenic signaling factor in vascular development and disease." Blood, The Journal of the American Society of Hematology 119.6 (2012): 1345-1352.
Nichol, Donna, et al. "Impaired angiogenesis and altered Notch signaling in mice overexpressing endothelial Egfl7." Blood, The Journal of the American Society of Hematology 116.26 (2010): 6133-6143.
Nikolić, Iva, et al. "EGFL7 ligates αvβ3 integrin to enhance vessel formation." Blood, The Journal of the American Society of Hematology 121.15 (2013): 3041-3050.
Nikolic, Iva, Karl-Heinz Plate, and Mirko HH Schmidt. "EGFL7 meets miRNA-126: an angiogenesis alliance." Journal of angiogenesis research 2.1 (2010): 9.
Ntziachristos, Panagiotis, et al. "From fly wings to targeted cancer therapies: a centennial for notch signaling." Cancer cell 25.3 (2014): 318-334.
Oh, Jinju, et al. "High expression of epidermal growth factor-like domain 7 is correlated with poor differentiation and poor prognosis in patients with epithelial ovarian cancer." Journal of gynecologic oncology 25.4 (2014): 334-341.
Oh, Philmo, et al. "In vivo mapping of notch pathway activity in normal and stress hematopoiesis." Cell stem cell 13.2 (2013): 190-204.
Papaioannou, Dimitrios, et al. "Prognostic and biological significance of the proangiogenic factor EGFL7 in acute myeloid leukemia." Proceedings of the National Academy of Sciences 114.23 (2017): E4641-E4647.
Paschka, Peter, et al. "Wilms' tumor 1 gene mutations independently predict poor outcome in adults with cytogenetically normal acute myeloid leukemia: a cancer and leukemia group B study." Journal of Clinical Oncology 26.28 (2008): 4595.
Renz, Marc, et al. "Regulation of β1 integrin-Klf2-mediated angiogenesis by CCM proteins." Developmental cell 32.2 (2015): 181-190.

(56) References Cited

OTHER PUBLICATIONS

Schmidt, Mirko HH, et al. "Epidermal growth factor-like domain 7 (EGFL7) modulates Notch signalling and affects neural stem cell renewal." Nature cell biology 11.7 (2009): 873-880.
Schmitt, Thomas M., et al. "Induction of T cell development and establishment of T cell competence from embryonic stem cells differentiated in vitro." Nature immunology 5.4 (2004): 410-417.
Shen, Xiaochun, et al. "Epidermal growth factor-like domain 7 promotes cell invasion and angiogenesis in pancreatic carcinoma." Biomedicine & Pharmacotherapy 77 (2016): 167-175.
Short, Nicholas J., and Farhad Ravandi. "Acute myeloid leukemia: past, present, and prospects for the future." Clinical Lymphoma Myeloma and Leukemia 16 (2016) S25-S29.
Stein, Sarah J., et al. "Trib2 suppresses tumor initiation in Notch-driven T-ALL." PloS one 11.5 (2016).
Stone, Richard M., et al. "Postremission therapy in older patients with de novo acute myeloid leukemia: a randomized trial comparing mitoxantrone and intermediatedose cytarabine with standard-dose cytarabine." Blood, The Journal of the American Society of Hematology 98.3 (2001): 548-553.
Stone, Richard M., et al. "The multi-kinase inhibitor midostaurin (M) prolongs survival compared with placebo (P) in combination with daunorubicin (D)/cytarabine (C) induction (ind), high-dose C consolidation (consol), and as maintenance (maint) therapy in newly diagnosed acute myeloid leukemia (AML) patients (pts) age 18-60 with FLT3 mutations (muts): an international prospective randomized (rand) P-controlled double-blind trial (CALGB 10603/ Ratify [Alliance])." (2015): 6-6.
Suresh, Sukanya, and Alexandra E. Irvine. "The Notch signaling pathway in normal and malignant blood cell production." Journal of cell communication and signaling 9.1 (2015): 5-13.
Takeuchi, Kimio, et al. "EGF-like-domain-7 is required for VEGF-induced Akt/ERK activation and vascular tube formation in an ex vivo angiogenesis assay." PloS one 9.3 (2014).
Wang, Weihuan, et al. "Aberrant Notch signaling in the bone marrow microenvironment of acute lymphoid leukemia suppresses osteoblast-mediated support of hematopoietic niche function." Cancer research 76.6 (2016): 1641-1652.
Wang, Xiao-Xia, et al. "Attenuation of EGFL7 inhibits human laryngocarcinoma cells growth and invasion." International journal of clinical and experimental medicine 8.3 (2015): 3141.
Whitman, Susan P., et al. "Absence of the wild-type allele predicts poor prognosis in adult de novo acute myeloid leukemia with normal cytogenetics and the internal tandem duplication of FLT3: a cancer and leukemia group B study." Cancer research 61.19 (2001): 7233-7239.
Whitman, Susan P., et al. "FLT3 D835/I836 mutations are associated with poor disease-free survival and a distinct gene-expression signature among younger adults with de novo cytogenetically normal acute myeloid leukemia lacking FLT3 internal tandem duplications." Blood, The Journal of the American Society of Hematology 111.3 (2008): 1552-1559.
Wouters, Bas J., et al. "Double CEBPA mutations, but not single CEBPA mutations, define a subgroup of acute myeloid leukemia with a distinctive gene expression profile that is uniquely associated with a favorable outcome." Blood, The Journal of the American Society of Hematology 113.13 (2009): 3088-3091.
Yan, Pearlly, et al. "Genome-wide methylation profiling in decitabine-treated patients with acute myeloid leukemia." Blood, The Journal of the American Society of Hematology 120.12 (2012): 2466-2474.
Zorko, Nicholas A., et al. "Mll partial tandem duplication and Flt3 internal tandem duplication in a double knock-in mouse recapitulates features of counterpart human acute myeloid leukemias." Blood, The Journal of the American Society of Hematology 120.5 (2012): 1130-1136.
International Preliminary Report on Patentability issued for Application No. PCT/US2018/029059, dated Nov. 7, 2019.

* cited by examiner

Parsatuzumab/Gilteritinib

SEQUENCE LISTING

<160> NUMBER OF SEQ ID NOS: 6

<210> SEQ ID NO 1
<211> LENGTH: 1764
<212> TYPE: DNA
<213> ORGANISM: Homo sapiens

<400> SEQUENCE: 1

| | | | | | | |
|---|---|---|---|---|---|---|
| gcaccaagct | ggccctgcac | ggctgcaagg | gaggctcctg | tggacaggcc | aggcaggtgg | 60 |
| gcctcaggag | gtgcctccag | gcggccagtg | ggcctgaggc | cccagcaagg | gctagggtcc | 120 |
| atctccagtc | ccaggacaca | gcagcggcca | ccatggccac | gcctgggctc | cagcagcatc | 180 |
| agagcagccc | ctgtggttgg | cagcaaagtt | cagcttggct | gggcccgctg | tgagggcttt | 240 |
| cgcgctacgc | cctgcggtgt | cccgagggct | gaggtctcct | catcttctcc | ctagcagtgg | 300 |
| atgagcaacc | caacgggggc | cggggaggg | gaactggccc | cgaggagag | gaaccccaaa | 360 |
| gccacatctg | tagccaggat | gagcagtgtg | aatccaggca | gccccagga | ccggggaggc | 420 |
| acaggtggcc | cccaccaccc | ggaggagcag | ctcctgcccc | tgtccggggg | atgactgatt | 480 |
| ctcctccgcc | aggccaccca | gaggagaagg | ccaccccgcc | tggaggcaca | ggccatgagg | 540 |
| ggctctcagg | aggtgctgct | gatgtggctt | ctggtgttgg | cagtgggcgg | cacagagcac | 600 |
| gcctaccggc | ccggccgtag | ggtgtgtgct | gtccgggctc | acggggaccc | tgtctccgag | 660 |
| tcgttcgtgc | agcgtgtgta | ccagcccttc | ctcaccacct | gcgacgggca | ccgggcctgc | 720 |
| agcacctacc | gaaccatcta | taggaccgcc | taccgccgca | gccctgggct | ggcccctgcc | 780 |
| aggcctcgct | acgcgtgctg | ccccggctgg | aagaggacca | gcgggcttcc | tggggcctgt | 840 |
| ggagcagcaa | tatgccagcc | gccatgccgg | aacggaggga | gctgtgtcca | gcctggccgc | 900 |
| tgccgctgcc | ctgcaggatg | gcggggtgac | acttgccagt | cagatgtgga | tgaatgcagt | 960 |
| gctaggaggg | gcggctgtcc | ccagcgctgc | gtcaacaccg | ccggcagtta | ctggtgccag | 1020 |
| tgttgggagg | ggcacagcct | gtctgcagac | ggtacactct | gtgtgcccaa | gggagggccc | 1080 |
| cccaggtgg | cccccaaccc | gacaggagtg | gacagtgcaa | tgaaggaaga | agtgcagagg | 1140 |
| ctgcagtcca | gggtggacct | gctggaggag | aagctgcagc | tggtgctggc | cccactgcac | 1200 |
| agcctggcct | cgcaggcact | ggagcatggg | ctccccggacc | ccggcagcct | cctggtgcac | 1260 |
| tccttccagc | agctcggccg | catcgactcc | ctgagcgagc | agatttcctt | cctggaggag | 1320 |
| cagctggggt | cctgctcctg | caagaaagac | tcgtgactgc | ccagcgcccc | aggctggact | 1380 |
| gagcccctca | cgccgccctg | cagccccat | gcccctgccc | aacatgctgg | gggtccagaa | 1440 |
| accacctcgg | ggtgactgag | cggaaggcca | ggcagggcct | tcctcctctt | cctcctcccc | 1500 |
| ttcctcggga | ggctccccag | accctggcat | gggatgggct | gggatcttct | ctgtgaatcc | 1560 |
| accccctggct | accccaccc | tggctacccc | aacggcatcc | caaggccagg | tgggccctca | 1620 |
| gctgagggaa | ggtacgagct | ccctgctgga | gcctgggacc | catggcacag | gccaggcagc | 1680 |
| ccggaggctg | ggtggggcct | cagtgggggc | tgctgcctga | ccccagcac | aataaaaatg | 1740 |
| aaacgtgaaa | aaaaaaaaaa | aaaa | | | | 1764 |

<210> SEQ ID NO 2
<211> LENGTH: 273
<212> TYPE: PRT
<213> ORGANISM: Homo sapiens

<400> SEQUENCE: 2

Met Arg Gly Ser Gln Glu Val Leu Leu Met Trp Leu Leu Val Leu Ala

```
                1               5                  10                 15
        Val Gly Gly Thr Glu His Ala Tyr Arg Pro Gly Arg Arg Val Cys Ala
                        20                 25                 30

Val Arg Ala His Gly Asp Pro Val Ser Glu Ser Phe Val Gln Arg Val
                        35                 40                 45

Tyr Gln Pro Phe Leu Thr Thr Cys Asp Gly His Arg Ala Cys Ser Thr
                        50                 55                 60

Tyr Arg Thr Ile Tyr Arg Thr Ala Tyr Arg Ser Pro Gly Leu Ala
        65                 70                 75                 80

Pro Ala Arg Pro Arg Tyr Ala Cys Cys Pro Gly Trp Lys Arg Thr Ser
                        85                 90                 95

Gly Leu Pro Gly Ala Cys Gly Ala Ala Ile Cys Gln Pro Pro Cys Arg
                        100                105                110

Asn Gly Gly Ser Cys Val Gln Pro Gly Arg Cys Arg Cys Pro Ala Gly
                        115                120                125

Trp Arg Gly Asp Thr Cys Gln Ser Asp Val Asp Glu Cys Ser Ala Arg
        130                135                140

Arg Gly Gly Cys Pro Gln Arg Cys Val Asn Thr Ala Gly Ser Tyr Trp
        145                150                155                160

Cys Gln Cys Trp Glu Gly His Ser Leu Ser Ala Asp Gly Thr Leu Cys
                        165                170                175

Val Pro Lys Gly Gly Pro Pro Arg Val Ala Pro Asn Pro Thr Gly Val
                        180                185                190

Asp Ser Ala Met Lys Glu Glu Val Gln Arg Leu Gln Ser Arg Val Asp
                        195                200                205

Leu Leu Glu Glu Lys Leu Gln Leu Val Leu Ala Pro Leu His Ser Leu
        210                215                220

Ala Ser Gln Ala Leu Glu His Gly Leu Pro Asp Pro Gly Ser Leu Leu
        225                230                235                240

Val His Ser Phe Gln Gln Leu Gly Arg Ile Asp Ser Leu Ser Glu Gln
                        245                250                255

Ile Ser Phe Leu Glu Glu Gln Leu Gly Ser Cys Ser Cys Lys Lys Asp
                        260                265                270
        Ser

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Met Arg Gly Ser Gln Glu Val Leu Leu Met Trp Leu Leu Val Leu Ala
1               5                   10                  15

Val Gly Gly

<210> SEQ ID NO 4
<211> LENGTH: 78
<212> TYPE: PRT
<213> ORGANISM: Artificial Sequence
<220> FEATURE:
<223> OTHER INFORMATION: Synthetic Construct

<400> SEQUENCE: 4

Gly Arg Arg Val Cys Ala Val Arg Ala His Gly Asp Pro Val Ser Glu
1               5                   10                  15
```

```
-continued

Ser Phe Val Gln Arg Val Tyr Gln Pro Phe Leu Thr Thr Cys Asp Gly
            20                  25                  30

His Arg Ala Cys Ser Thr Tyr Arg Thr Ile Tyr Arg Thr Ala Tyr Arg
            35                  40                  45

Arg Ser Pro Gly Leu Ala Pro Ala Arg Pro Arg Tyr Ala Cys Cys Pro
 50                  55                  60

Gly Trp Lys Arg Thr Ser Gly Leu Pro Gly Ala Cys Gly Ala
 65                  70                  75

<210> SEQ ID NO 5
<211> LENGTH: 28
<212> TYPE: PRT
<213> ORGANISM: Artificial Sequence
<220> FEATURE:
<223> OTHER INFORMATION: Synthetic Construct

<400> SEQUENCE: 5

Cys Gln Pro Pro Cys Arg Asn Gly Gly Ser Cys Val Gln Pro Gly Arg
 1               5                  10                  15

Cys Arg Cys Pro Ala Gly Trp Arg Gly Asp Thr Cys
            20                  25

<210> SEQ ID NO 6
<211> LENGTH: 36
<212> TYPE: PRT
<213> ORGANISM: Artificial Sequence
<220> FEATURE:
<223> OTHER INFORMATION: Synthetic Construct

<400> SEQUENCE: 6

Cys Ser Ala Arg Arg Gly Gly Cys Pro Gln Arg Cys Val Asn Thr Ala
 1               5                  10                  15

Gly Ser Tyr Trp Cys Gln Cys Trp Glu Gly His Ser Leu Ser Ala Asp
            20                  25                  30

Gly Thr Leu Cys
            35
```

RECOMBINANT EGFL7, EGFL7 ANTIBODIES, AND USES THEREOF

CROSS REFERENCE TO RELATED APPLICATIONS

This application is a national stage application filed under 35 U.S.C. § 371 of PCT/US2018/029059 filed Apr. 24, 2018, which claims the benefit of U.S. Provisional Patent Application Ser. No. 62/489,015 filed Apr. 24, 2017, the disclosures of which are expressly incorporated herein by reference.

REFERENCE TO A SEQUENCE LISTING

The Sequence Listing submitted on Oct. 24, 2019 as a text file named "10336-304US1_Sequence_Listing.txt," created on Oct. 24, 2019, and having a size of 6863 bytes is hereby incorporated by reference pursuant to 37 C.F.R. § 1.52(e)(5).

FIELD

The present disclosure relates to recombinant EGFL7, EGFL7 antibodies, and uses thereof.

BACKGROUND

Acute myeloid leukemia (AML) is a clonal hematopoietic disease characterized by the proliferation of immature blasts in the bone marrow (BM) and blood. Genetic alterations including chromosomal translocations and deletions, and gene mutations leading to aberrant downstream target gene expression contribute to AML initiation and maintenance. Previously, increased microRNA-126-3p (miR-126) expression was detected in patients with cytogenetically normal AML (CN-AML) correlated with shorter overall survival (OS). Furthermore, it was found that miR-126 to be essential for leukemia stem cell (LSC) homeostasis and in vivo targeting of miR-126 in a patient-derived xenograft model resulted in prolonged survival in secondary bone marrow transplant (BMT) recipients. miR-126 is located within intron 7 of a protein-coding gene known as Epithelial Growth Factor-Like 7 (EGFL7). While an important role for miR-126 in AML biology has been shown, no studies have been performed to understand the prognostic and functional implications of expression of its host gene, EGFL7, in AML.

EGFL7 is a secreted protein of approximately 30 KDa and plays an important physiological role in angiogenesis. Unlike other angiogenic factors (e.g., VEGF), physiological EGFL7 expression and function has mainly been restricted to the endothelial cells where it regulates survival, migration, and differentiation. Aberrant expression of EGFL7 has been shown to be involved in tumor growth and disease progression of several solid tumors, including hepatocellular carcinoma, malignant glioma, and breast, lung, and pancreatic cancers, but its role in hematopoietic malignancies is currently unknown. Therefore, what is needed are prognostic markers of hematologic malignancies and new treatments for hematologic malignancies.

The compounds, compositions, and methods disclosed herein address these and other needs.

SUMMARY

Disclosed herein are recombinant EGFL7, EGFL7 antibodies, and uses thereof. For the first time, the inventors have discovered a role for EGFL7 in hematologic malignancies (for example, acute myeloid leukemia (AML)). Thus, in some embodiments, anti-EGFL7 antibodies are useful in preventing or treating hematologic malignancies. In other embodiments, EGFL7 expression levels are useful for predicting a subject's responsiveness to a therapeutic agent. In addition, EGFL7 is important for hematopoiesis, and thus in some embodiments, recombinant EGFL7 can be used for expanding hematopoietic stem and progenitor cells (HSPCs).

In one aspect, disclosed herein is a method for treating acute myeloid leukemia, comprising: administering to a subject in need thereof an effective amount of an antibody or antigen-binding fragment thereof that specifically binds to an EGFL7 polypeptide.

In some embodiments, the antibody or antigen-binding fragment thereof binds to the EGF/DSL domain of EGFL7. In some embodiments, the antibody is a monoclonal antibody. In some embodiments, the antibody is parsatuzumab.

In some embodiments, the antibody or antigen-binding fragment thereof is administered in combination with an NP-antagomiR-126 therapy.

In some embodiments, the antibody or antigen-binding fragment thereof is administered in combination with an additional chemotherapeutic agent. In some embodiments, the additional chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®). In some embodiments, the additional chemotherapeutic agent is a FLT3 inhibitor. In some embodiments, the FLT3 inhibitor is gilteritinib.

In some embodiments, the hematologic malignancy is acute myeloid leukemia. In some embodiments, the acute myeloid leukemia (AML) is cytogenetically normal acute myeloid leukemia (CN-AML). In some embodiments, the antibody or antigen-binding fragment thereof inhibits EGFL7 activity in acute myeloid leukemia blasts.

In another aspect, disclosed herein is a method of predicting responsiveness of a subject with acute myeloid leukemia to an EGFL7 inhibitor, the method comprising:
  assaying a sample from the subject for the expression of EGFL7; and
  comparing the expression of EGFL7 to a healthy control;
  wherein an increase in EGFL7 expression in the sample compared to the healthy control is an indication of responsiveness of the subject to the EGFL7 inhibitor.

In some embodiments, the expression of EGFL7 is detected by measuring EGFL7 protein levels. In some embodiments, the expression of EGFL7 is detected by measuring EGFL7 mRNA levels. In some embodiments, the EGFL7 expression in the sample is increased at least 10% relative to a healthy control.

In some embodiments, the method further comprises treating the subject with an EGFL7 inhibitor if an increase in EGFL7 expression is detected. In some embodiments, the EGFL7 inhibitor is an antibody or antigen-binding fragment thereof that specifically binds to an EGFL7 polypeptide.

In one aspect, disclosed herein is a method of expanding hematopoietic stem and progenitor cells (HSPCs) comprising: administering to a hematopoietic stem and progenitor cell a recombinant EGFL7 protein.

In some embodiments, the recombinant EGFL7 protein does not cause a loss of stem cell potential. In some embodiments, the hematopoietic stem and progenitor cells (HSPCs) are selected from HSC, MPP1-4, CMP, GMP, or MEP populations.

In one aspect, disclosed herein is a composition comprising: an antibody or antigen-binding fragment thereof that specifically binds to an EGFL7 polypeptide; and a FLT3 inhibitor.

In some embodiments, the antibody or antigen-binding fragment thereof binds to the EGF/DSL domain of EGFL7. In some embodiments, the antibody is a monoclonal antibody. In some embodiments, the antibody is parsatuzumab. In some embodiments, the FLT3 inhibitor is gilteritinib.

BRIEF DESCRIPTION OF THE DRAWINGS

The accompanying figures, which are incorporated in and constitute a part of this specification, illustrate several aspects described below.

(FIG. 1E) OS and (FIG. 1F) EFS according to EGFL7 risk group in older CN-AML patients. The favorable risk group was comprised of patients with EGFL7 low expression/high methylation; the unfavorable risk group included the remaining patients (high expression/low methylation, high expression/high methylation, low expression/low methylation). The median values of EGFL7 expression and EGFL7 promoter methylation were used as the high/low cut points.

(FIG. 2A) Normal bone marrow (NBM) samples from healthy donors (n=3) were compared with leukapheresis samples of AML patients (ptAML, n=11). EGFL7 levels were measured in AML samples by real time PCR (RT-PCR) and the results were normalized to β-ACTIN as internal control. The inset shows the mean±SD of EGFL7 mRNA between NBM and AML. * indicates P<0.05. (FIG. 2B) EGFL7 protein levels in human NBM (n=3) and blasts of AML patients (n=11) were determined by immunoblotting with GAPDH as loading control. (FIG. 2C) Total RNA from AML blasts of our $Mll^{PTD/WT}Flt3^{ITD/WT}$ mouse model (mAML, n=4) and wild-type mice (WT, n=4) were extracted for the detection of mouse Egfl7 mRNA by RT-PCR with β-Actin as internal control. Inset shows the mean±SD of Egfl7 mRNA between NBM and AML. **indicates P<0.01. (FIG. 2D) Mouse Egfl7 protein levels in AML blasts from $Mll^{PTD/WT}Flt3^{ITD/WT}$ mice (mAML) (n=4) and WT murine controls (n=4) were assessed by immunoblotting using Gapdh as loading control. (FIG. 2E) Immunohistochemistry of Egfl7 in BM from $Mll^{PTD/WT}Flt3^{ITD/WT}$ leukemic mice (n=3) vs. WT (n=3) controls using an Egfl7 specific antibody along with no antibody controls. Original magnification 100×, insets with same areas across the samples are magnified at same strength.

(FIG. 3A) Blasts of AML patients (ptAML, n=3) were cultured in SFEM medium+10% fetal bovine serum (FBS) supplemented with cytokines for 24 h. EGFL7 protein level in the cell culture supernatant was detected by ELISA and compared with that in media from wells without cultured cells. ** indicates P<0.01, * indicates P<0.05. (FIG. 3B) Blasts of AML patients (n=3) were cultured in SFEM+10% FBS medium supplemented with cytokines for 24 h. The EGFL7 protein in the cell culture supernatant was assessed by immunoblotting with recombinant EGFL7 (rEGFL7) as positive control and media from wells without cultured cells as negative control. Ponceau S staining shows the loading control for protein. (FIG. 3C) EGFL7 protein levels in sera from normal healthy controls (sN, n=6) and AML patients (sAML, n=6) were determined by EGFL7 ELISA kit. SFEM medium alone and 10% FBS serve as blank controls. * indicates P<0.05, ** indicates P<0.01. (FIG. 3D) Equal volume of serum from AML patients (sAML, n=12) or normal healthy donors (sN, n=6) was subjected to the separation of exosomal versus non-exosomal eluant using the ExoQuick kit (SBI, Palo Alto, Calif.). EGFL7 protein levels in both isolated exosomes and the supernatant were determined by immunoblotting. SFEM containing 10% FBS served as a negative control while rEGFL7 was used as a positive control. Ponceau S staining shows the loading of proteins.

(FIG. 4C). Blasts of the indicated AML patients (20,000 cells) were mixed with methylcellulose medium in the absence or presence of 0.25 μM recombinant human EGFL7 (rEGFL7) and plated on to 2 cm dishes for 10 days. The colonies with more than 50 cells were enumerated using a light microscope. Each condition for each patient (n=4) was plated in triplicate,  indicates P<0.01, *** indicates P<0.001. (FIG. 4D) Blasts from AML patients (n=4) were cultured in SFEM+2% BSA in the absence or presence of 0.25 μM rEGFL7 for 20 min. Total proteins were extracted for immunoblotting of phosphorylated AKT-S473 (pAKT-S473), total AKT and GAPDH. (FIG. 4E) AML blasts from $Mll^{PTD/WT}Flt3^{ITD/WT}$ mice (n=3) were cultured in IMDM medium+2% BSA in the absence or presence of 0.25 μl M recombinant rEgfl7 for 20 min. Total proteins were extracted for immunoblotting of pAkt-S473, total Akt and Gapdh.

(FIG. 6C) DFS according to EGFL7 risk group in older CN-AML patients. The favorable risk group comprised patients with EGFL7 low expression/high methylation; the unfavorable risk group comprised the remaining patients (high expression/low methylation, high expression/high methylation, low expression/low methylation). The median values of EGFL7 expression and EGFL7 promoter methylation were used as cut-offs.

(FIG. 7A) Kasumi-1 acute myeloid leukemia (AML) cells were cultured in RPMI-1640 for 24 h. EGFL7 protein levels within the cells and cell culture supernatant were assessed by immunoblotting with recombinant EGFL7 (rEGFL7) as positive control. Ponceau S staining shows the loading of proteins. (FIG. 7B) Kasumi cells were stimulated with 100 nM rEGFL7 for 12 hours in RPMI1640 with 10% FBS. Cell proliferation was assessed using APC-BrdU/7AAD staining coupled with flow cytometry. (FIG. 7C) Kasumi-1 cells (2500 cells) were mixed with methylcellulose medium in the absence or presence of 100 nM recombinant human EGFL7 and plated on to 2 cm dishes for 10 days. The number of colonies with more than 50 cells was counted under a light microscope. Each condition was repeated in triplicate in three independent experiments. * indicates P<0.05. (FIG. 7D) Exponentially growing Kasumi-1 cells were starved in serum free RPMI1640 medium for 1 hr, followed by addition of 100 nM recombinant EGFL7 for 5 min. Total proteins were extracted for immunoblotting of phosphorylated AKT-S473 (pAKT-S473, total AKT and GAPDH FIG. 8A-8C. Kasumi-1 cells were transduced with non-targeting scramble control (shSCR) or anti-EGFL7 short hairpin RNA (shEGFL7) lentiviral vectors. Transduced cells were sorted for Green Fluorescent Protein expression and cultured in RPMI media, supplemented with 20% of Fetal Bovine Serum.

FIG. 15A. Co-IPs in Kasumi-1 cells using anti-EGFL7 antibody or normal rabbit IgG in Protein G Plus/Protein A agarose beads. Eluate was analyzed by immunoblotting for NOTCH1,-3, and EGFL7. FIG. 15B. Co-IPs with rabbit anti NOTCH1-3 antibody or normal rabbit IgG in Protein G Plus/Protein A agarose beads. FIG. 15C. Immunoblot for cleaved and total NOTCH2 in primary AML blasts stimulated in 0.25 µM rEGFL7. FIG. 15D. RT-PCR on primary AML blasts stimulated with 0.25 µM rEGFL7, *P<0.05.

FIG. 16A. Secretion of Egfl7 protein by BMSCs cultured from mice with AML or WT controls. FIG. 16B. Secretion of Egfl7 protein by normal BMSCs exposed to normoxia (21%O2) or hypoxia (1%O2). FIG. 16C. Apoptosis of measured by AnnexinV staining of normal BMSCs stimulated with 250 nM rhEGFL7 or negative control. *P<0.05.

FIG. 17A. qRT-PCR of EGFL7 in LSC-enriched and non-LSC enriched subpopulations of primary AML patient samples normalized to B-ACTIN. Number of quiescent ($CTV^{MAX}$) AML cells treated with FIG. 17B. rEGFL7 or control (vs Unstim). FIG. 17C. anti-EGFL7 (Parsatuzumab) antibody or IgG1 control (vs Unstim). *P<0.05.

FIG. 18A. CFUs on primary AML blasts treated with anti-EGFL7 vs. IGg1 controls. FIG. 18B, HES-1 real time RT-PCR on anti-EGFL7 treated primary AML blasts vs. IGg1 control. (*P<0.05, **P<0.01).

FIG. 20A. CBCs from mice harvested after treatment. FIG. 20B. Percent engraftment of treated BM (CD45.2+) transplanted into BoyJ recipient mice (CD45.1). No significant changes were observed.

FIG. 21A. Immunoblot of Egfl7 in normal BM (NBM) from WT mice (n=4) were compared to blasts from Mll PTD; Flt3 ITD (mAML1-4) mouse AML samples (n=4). FIG. 21B. Egfl7 expression in pre-leukemic BM.

(FIG. 23A) Primary blasts from AML patients (n=3) were cultured in SFEM medium with 2% BSA in the presence or absence (Unstim) of 0.25 µM rEGFL7 for 4 h. Total proteins were extracted for immunoblotting of NICD (cleaved NOTCH1) with GAPDH as loading control. (FIG. 23B) Total RNA was extracted for quantitative real time (qRT-PCR) analysis of HES1 mRNA with β-ACTIN as internal control. $*p<0.05$ vs un-stimulated control (Unstim). (FIG. 23C) qRT-PCR for NOTCH2 mRNA at 4 h and 24 h after stimulation of primary AML blasts with 0.25 uM rEGFL7 or unstim controls. (FIG. 23D) Primary blasts from AML patients (n=3) were cultured in SFEM medium in the absence or presence of 100 µg/ml of normal IgG or anti-human EGFL7 antibody for 2 h. Total protein was extracted for immunoblotting of NICD with GAPDH as loading control. (FIG. 23E) Primary blasts from AML patients (n=3) were cultured in SFEM medium in the absence or presence of 100 µg/ml of normal IgG or anti-human EGFL7 antibody for 2 and 10 h. Total RNA was extracted for quantitative real time RT-PCR analysis of HES1 mRNA with β-ACTIN as internal control. $*p<0.05$, $***p<0.001$ vs IgG.

(FIG. 24A) Overview of experiments using DLL4-FC and IgG-FC control coated plates to induce NOTCH activation. (FIG. 24B) THP-1 cells were pre-treated with 10 µM γ-secretase inhibitor (AVA), 100 µg/ml anti-EGFL7 antibody or 0.25 µM rEGFL7 for 30 min, then transferred to IgG-Fc or DLL4-Fc coated plates. After 4 h of incubation total RNA from THP-1 cells was extracted for qRT-PCR analysis of HES1 with β-ACTIN as internal control. $\#\#\#P<0.001$ DLL4-FC vs IgG-FC; $***P<0.001$ DLL4+AVA, DLL4+rEGFL7, and DLL4+anti-EGFL7 vs DLL4-FC. (FIG. 24C) Primary AML blasts were pretreated with 10 µM γ-secretase inhibitor (AVA), 100 µg/ml anti-EGFL7 antibody or 0.25 µM rEGFL7 for 30 min, then transferred to IgG-Fc or DLL4-Fc coated plates. After 4 h of incubation, total RNA was extracted for RT-PCR analysis of HES1 mRNA with β-ACTIN as internal control. $\#\#\#P<0.001$ DLL4-Fc vs IgG-Fc; $*P<0.05$, $***P<0.001$ vs DLL4 Fc. THP-1 cells were treated with the indicated concentration of anti-EGFL7 (@E7) then assessed for apoptosis using (FIG. 24D) AnnexinV+ staining and FACS; $*P<0.05$ (FIG. 24E) Immuno-blotting for PARP1 and Casp3 cleavage. (FIG. 24F) Cell differentiation was assessed by CD11B and CD14 staining 96-hours post anti-EGFL7 treatments; $*P<0.05$. (FIG. 24G) To determine whether activation of NOTCH by DLL4-Fc could be accentuated by anti-EGFL7 treatment, THP-1 cells were first treated with anti-EGFL7 (100 µg/ml) and then cultured on DLL4-FC or IgG-Fc coated plates and then assessed for apoptosis using AnnexinV+ staining and FACS. $*P<0.05$ DLL4-Fc and anti-EGFL7; vs DLL4-FC+ anti-EGFL7.

(FIG. 25A) Overall survival of transplanted NSG mice which were treated with Parsatuzumab or IgG1 control (4 mice per group; dosage 50 mg/kg intraperitoneal injected). Mice treated with Parsatuzumab had a significant longer overall survival compared to IgG treated mice. (FIG. 25B) HES-1 levels were measured after in vivo treatment with Parsatuzumab and IgG1 control, GAPDH was used as loading control.

DETAILED DESCRIPTION

Figure 1A:
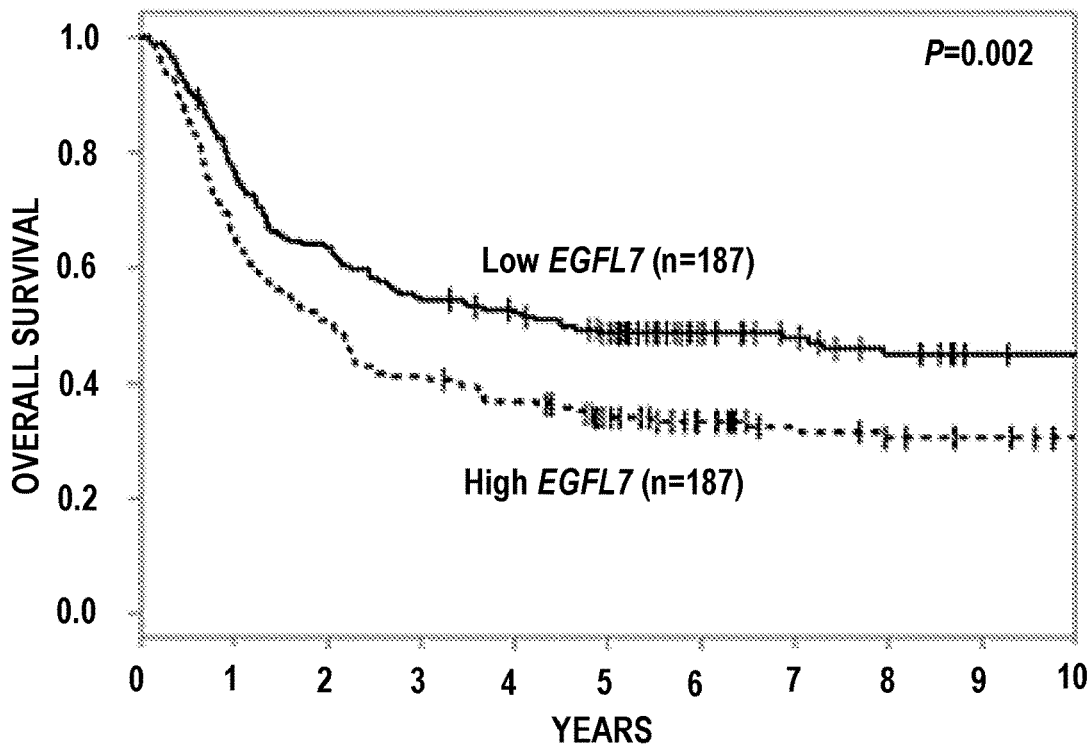
FIG. 1A-1F. Prognostic significance of EGFL7 in younger and older cytogenetically normal acute myeloid leukemia (CN-AML) patients. Association of EGFL7 expression levels with (FIG. 1A) overall (OS) and (FIG. 1B) event-free survival (EFS) of younger (aged <60 years) adult patients. Association of EGFL7 expression levels with (FIG. 1C) overall (OS) and (FIG. 1D) event-free survival (EFS) of older (aged ≥60 years) patients.

Disclosed herein are recombinant EGFL7, EGFL7 antibodies, and uses thereof. For the first time, the inventors have discovered a role for EGFL7 in hematologic malignancies (for example, acute myeloid leukemia (AML)). Thus, in some embodiments, anti-EGFL7 antibodies are useful in preventing or treating hematologic malignancies. In other embodiments, EGFL7 expression is useful for predicting a subject's responsiveness to a therapeutic agent. In addition, EGFL7 is important for hematopoiesis, and thus in some embodiments, recombinant EGFL7 can be used for expanding hematopoietic stem and progenitor cells (HSPCs).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains at least some portion of the epitope binding features of an Ig molecule (for example, allowing it to specifically bind to EGFL7). An antibody is said to be "capable of binding" a molecule if it is capable of specifically reacting with the molecule to thereby bind the molecule to the antibody.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

A "monoclonal antibody" as used herein is intended to refer to a preparation of antibody molecules, which share a common heavy chain and common light chain amino acid sequence, or any functional fragment, mutant, variant, or derivation thereof which retains at least the light chain epitope binding features of an Ig molecule, in contrast with "polyclonal" antibody preparations that contain a mixture of different antibodies. Monoclonal antibodies can be generated by several known technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

The term "EGFL7 protein", as used herein refers to the protein encoded by SEQ ID NO:1 (Accession number NM_016215), and natural variants or homologues thereof. In some embodiments, the EGFL7 amino acid sequence is SEQ ID NO:2 (Accession number NP_057299).

The term "variant" or "derivative" as used herein refers to an amino acid sequence derived from the amino acid sequence of the parent protein having one or more amino acid substitutions, insertions, and/or deletions.

Methods of Treatment

In one aspect, disclosed herein is a method for treating or preventing a hematologic malignancy, comprising: administering to a subject in need thereof an effective amount of an antibody or antigen-binding fragment thereof that specifically binds to an EGFL7 polypeptide.

In one aspect, disclosed herein is a method for treating acute myeloid leukemia, comprising: administering to a subject in need thereof an effective amount of an antibody or antigen-binding fragment thereof that specifically binds to an EGFL7 polypeptide.

In some embodiments, the antibody or antigen-binding fragment thereof binds to the EGF/DSL domain of EGFL7. In some embodiments, the antibody is a monoclonal antibody. In some embodiments, the antibody is parsatuzumab. Additional EGFL7 antibodies, or antigen-binding fragments thereof, are known in the art, for example, see U.S. Pat. No. 8,398,976, WO2007/106915, and WO2010/129904, which are hereby incorporated by reference. Anti-human EGFL7 antibody (parsatuzumab) is commercially available and can be obtained from Creative Biolabs (Shirley, N.Y., USA).

In some embodiments, the antibody or antigen-binding fragment thereof is administered in combination with an NP-antagomiR-126 therapy.

In some embodiments, the antibody or antigen-binding fragment thereof is administered in combination with an additional chemotherapeutic agent. In some embodiments, the additional chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®). In some embodiments, the additional chemotherapeutic agent is a FLT3 inhibitor. In some embodiments, the FLT3 inhibitor is gilteritinib. In some embodiments, the FLT3 inhibitor is quizartinib.

In some embodiments, the antibody or antigen-binding fragment thereof is administered in combination with a BCL-2 inhibitor, an AXL inhibitor, an IDH inhibitor, an MDM inhibitor, a bromodomain inhibitor, a SYK inhibitor, or a combination thereof. In some embodiments, the antibody or antigen-binding fragment thereof is administered in combination with a BCL-2 inhibitor. In some embodiments, the antibody or antigen-binding fragment thereof is administered in combination with a BCL-2 inhibitor is selected from venetoclax, ABT-263, or ABT-737. In some embodiments, the antibody or antigen-binding fragment thereof is administered in combination with venetoclax.

In some embodiments, the antibody or antigen-binding fragment thereof is administered in combination with a kinase inhibitor. In some embodiments, the antibody or antigen-binding fragment thereof is administered in combination with a tyrosine kinase inhibitor.

In some embodiments, the inhibitor is a tyrosine kinase inhibitor, wherein the tyrosine kinase is selected from Flt1, Flt4, KDR, EGFR, Ret, ALK, MET, EML4-ALK, JAK1, JAK2, BRAF, BCR/ABL1, Kit, PDGF-Rα/β, Mek1, Mek2, TEK, ERBβ2, EGFR, BTK, JAK3, PI3-K, VEGFR2, VEGFR3, CDK4, and/or CDK6.

In some embodiments, the tyrosine kinase inhibitor is vandetanib (Caprelsa®). In some embodiments, the tyrosine kinase inhibitor is crizotinib (Xalkori®). In some embodiments, the tyrosine kinase inhibitor is ruxolitinib (Jakafi®/Jakavi®). In some embodiments, the tyrosine kinase inhibitor is vemurafenib (Zelboraf®). In some embodiments, the tyrosine kinase inhibitor is bosutinib (Bosulif®). In some embodiments, the tyrosine kinase inhibitor is axitinib (Inlyta®). In some embodiments, the tyrosine kinase inhibitor is cabozantinib (Cometriq®). In some embodiments, the tyrosine kinase inhibitor is regorafinib (Stivarga®). In some embodiments, the tyrosine kinase inhibitor is ponatinib (Iclusig®). In some embodiments, the tyrosine kinase inhibitor is dabrafenib (Tafinlar®). In some embodiments, the tyrosine kinase inhibitor is trametinib (Mekinist®). In some embodiments, the tyrosine kinase inhibitor is afatinib (Gilotrif®). In some embodiments, the tyrosine kinase inhibitor is ibrutinib (Imbruvica®). In some embodiments, the tyrosine kinase inhibitor is tofacitinib (Xeljanz®). In some embodiments, the tyrosine kinase inhibitor is idelalisib (Zydelig®). In some embodiments, the tyrosine kinase inhibitor is ceritinib (Zykadia®). In some embodiments, the tyrosine kinase inhibitor is lenvatinib (Lenvima®). In some embodiments, the tyrosine kinase inhibitor is palbociclib (Ibrance®).

In one aspect, disclosed herein is a method for treating or preventing a hematologic malignancy, comprising: administering to a subject in need thereof a therapeutically effective amount of an antibody or antigen-binding fragment thereof that specifically binds to an EGFL7 polypeptide.

Hematologic Malignancies

In some embodiments, the methods disclosed herein are used to treat a cancer, for example, a hematologic malignancy. In some embodiments; the hematologic malignancy includes, but is not limited to, myeloid disorder, lymphoid disorder, leukemia; lymphoma, myelodysplastic syndrome (MDS), myeloproliferative disease (MPD), mast cell disorder, and myeloma (e.g., multiple myeloma), among others.

In some embodiments, the hematologic malignancy is leukemia. In some embodiments, the hematologic malignancy is acute myeloid leukemia (AML). In some embodiments, the acute myeloid leukemia (AML) is cytogenetically normal acute myeloid leukemia (CN-AML). In some embodiments, the acute myeloid leukemia (AML) is AML inv(16). In some embodiments, the acute myeloid leukemia (AML) is AML t(8;21). In some embodiments, the acute myeloid leukemia (AML) is AML complex. In some embodiments, the acute myeloid leukemia (AML) is AML t(15;17). In some embodiments, the antibody or antigen-binding fragment thereof inhibits EGFL7 activity in acute myeloid leukemia blasts. In some embodiments, the hematologic malignancy is acute lymphoblastic leukemia (ALL). In some embodiments, the acute lymphoblastic leukemia (ALL) is ALL t(12;21), In some embodiments, the acute lymphoblastic leukemia (ALL) is ALL hyperdiploid. In some embodiments, the acute lymphoblastic leukemia (ALL) is c-/Pre-B-ALL t(9;22). In some embodiments, the acute lymphoblastic leukemia (ALL) is c-/Pre-B-ALL.

Diagnostic Methods

In another aspect, disclosed herein is a method of predicting responsiveness of a subject with a hematologic malignancy to an EGFL7 inhibitor, the method comprising:
assaying a sample from the subject for the expression of EGFL7;
comparing the expression of EGFL7 to a healthy control;
wherein an increase in EGFL7 expression in the sample compared to the healthy control is an indication of responsiveness of the subject to the EGFL7 inhibitor.

In another aspect, disclosed herein is a method of predicting responsiveness of a subject with acute myeloid leukemia to an EGFL7 inhibitor, the method comprising:
assaying a sample from the subject for the expression of EGFL7; and
comparing the expression of EGFL7 to a healthy control;
wherein an increase in EGFL7 expression in the sample compared to the healthy control is an indication of responsiveness of the subject to the EGFL7 inhibitor.

In some embodiments, the expression of EGFL7 is detected by measuring EGFL7 protein levels. In some embodiments, the expression of EGFL7 is detected by measuring EGFL7 mRNA levels. In some embodiments, the EGFL7 expression in the sample is increased at least 10% (for example, at least 10%, at least 20%, at least 30%, at least 40%, at least 50%, at least 60%, at least 70%, at least 80%, at least 90%, at least 100%) relative to a healthy control.

In some embodiments, the method further comprises treating the subject with an EGFL7 inhibitor if an increase in EGFL7 expression is detected. In some embodiments, the EGFL7 inhibitor is an antibody or antigen-binding fragment thereof that specifically binds to an EGFL7 polypeptide.

In some embodiments, the antibody or antigen-binding fragment thereof binds to the EGF/DSL domain of EGFL7. In some embodiments, the antibody is a monoclonal antibody. In some embodiments, the antibody is parsatuzumab.

In some embodiments, the antibody or antigen-binding fragment thereof is administered in combination with an NP-antagomiR-126 therapy.

In some embodiments, the antibody or antigen-binding fragment thereof is administered in combination with an additional chemotherapeutic agent. In some embodiments, the additional chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®). In some embodiments, the additional chemotherapeutic agent is a FLT3 inhibitor. In some embodiments, the FLT3 inhibitor is gilteritinib.

Methods for Expanding Hematopoietic Stem and Progenitor Cells (HSPC)

In one aspect, disclosed herein is a method of expanding hematopoietic stem and progenitor cells (HSPCs) comprising: administering to a cell a recombinant EGFL7 protein.

In one aspect, disclosed herein is a method of expanding hematopoietic stem and progenitor cells (HSPCs) comprising: administering to a hematopoietic stem and progenitor cell a recombinant EGFL7 protein in an amount effective to promote expansion and/or proliferation of a hematopoietic stem and progenitor cell (or a plurality of hematopoietic stem and progenitor cells).

In one aspect, disclosed herein is a method of expanding hematopoietic stem and progenitor cells (HSPCs) in vitro comprising: administering to a cell a recombinant EGFL7 protein.

In one aspect, disclosed herein is a method of expanding hematopoietic stem and progenitor cells (HSPCs) in vitro comprising: administering to a hematopoietic stem and progenitor cell a recombinant EGFL7 protein.

In some embodiments, the recombinant EGFL7 protein does not cause a loss of stem cell potential. In some embodiments, the hematopoietic stem and progenitor cells (HSPCs) are selected from HSC, MPP1-4, CMP, GMP, or MEP populations.

In some embodiments, the hematopoietic stem and progenitor cell (HSPC) lineage is selected from long term hematopoietic stem cells (LT-HSCs), short term hematopoietic stem cells (ST-HSCs), hematopoietic progenitor cells (HPCs), multipotent progenitors (MPPs), oligodendrocyte pre-progenitors (OPPs), monocyte progenitors, granulocyte progenitors, common myeloid progenitors (CNN, common lymphoid progenitors (CLPs), granulocyte-monocyte progenitors (GMPs), granulocyte progenitors, monocyte progenitors, megakaryocyte-erythroid progenitors (MEPs), megakaryocyte progenitors, or erythroid progenitors.

The population of hematopoietic stem and progenitor cells can be obtained from many suitable sources, including, for example, bone marrow, peripheral blood cells, peripheral blood cells that have undergone apheresis, peripheral blood cells that have undergone leukapheresis, umbilical cord blood, amniotic fluid, cultured HSC cells, an immortalized HSC cell line, or a conditionally immortalized HSC cell line.

Compounds and Compositions

In some embodiments, disclosed herein are EGFL7 inhibitors. In some embodiments, the EGFL7 inhibitor is antibody or antigen-binding fragment thereof binds to EGFL7. In some embodiments, the antibody or antigen-binding fragment thereof binds to the EGF/DSL domain of EGFL7. In some embodiments, the antibody is a monoclonal antibody. In some embodiments, the antibody is parsatuzumab.

In some embodiments, the EGFL7 inhibitor is antibody or antigen-binding fragment thereof binds to an EGFL7 amino acid sequence (or EGFL7 fragment). In some embodiments, the EGFL7 amino acid sequence is SEQ ID NO:2. In some embodiments, the antibody or antigen-binding fragment thereof specifically binds to SEQ ID NO:2 (EGFL7 amino acid sequence), or a fragment thereof. In some embodiments, the antibody or antigen-binding fragment thereof specifically binds to the amino acid sequence encoded by SEQ ID NO:3 (EGFL7 signal peptide), or a fragment thereof. In some embodiments, the antibody or antigen-binding fragment thereof specifically binds to the amino acid sequence encoded by SEQ ID NO:4 (EMI domain), or a fragment thereof. In some embodiments, the antibody or antigen-binding fragment thereof specifically binds to the amino acid sequence encoded by SEQ ID NO:5 (EGF/DSL domain), or a fragment thereof. In some embodiments, the antibody or antigen-binding fragment thereof specifically binds to the amino acid sequence encoded by SEQ ID NO:6 (Ca2+ binding domain), or a fragment thereof.

In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:2, or a fragment thereof. In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:3, or a fragment thereof. In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:4, or a fragment thereof. In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:5, or a fragment thereof. In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:6, or a fragment thereof.

In some embodiments, the antibody or antigen-binding fragment thereof is comprised in a composition with an NP-antagomiR-126 therapy.

In some embodiments, the antibody or antigen-binding fragment thereof is comprised in a composition with an additional chemotherapeutic agent. In some embodiments, the additional chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®). In some embodiments, the additional chemotherapeutic agent is a FLT3 inhibitor. In some embodiments, the FLT3 inhibitor is gilteritinib.

In one aspect, disclosed herein is a composition comprising: an antibody or antigen-binding fragment thereof that specifically binds to an EGFL7 polypeptide; and a FLT3 inhibitor.

In some embodiments, the antibody or antigen-binding fragment thereof binds to the EGF/DSL domain of EGFL7. In some embodiments, the antibody is a monoclonal antibody. In some embodiments, the antibody is parsatuzumab. In some embodiments, the FLT3 inhibitor is gilteritinib.

Compositions, as described herein, comprising an active compound and an excipient of some sort may be useful in a variety of applications. For example, pharmaceutical compositions comprising an active compound and an excipient can be useful for the treatment or prevention of a hematologic malignancy. In one embodiment, disclosed herein is a pharmaceutical composition comprising: an antibody or antigen-binding fragment thereof that specifically binds to an EGFL7 polypeptide; and a pharmaceutically acceptable excipient.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethyl cellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Di stearoyl-sn-glycero-3-Phosphoethanolamine-N-[Methoxy(Polyethylene glycol)-2000], and 1,2-Di stearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethyl ene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Prognostic and Biological Significance of the Pro-Angiogenic Factor EGFL7 in Acute Myeloid Leukemia Epithelial Growth Factor Like 7 (EGFL7) is a protein that is secreted by endothelial cells and plays an important role in angiogenesis. Although EGFL7 is aberrantly overexpressed in solid tumors, its role in leukemia has not been evaluated. Here, it is determined that levels of both EGFL7 mRNA and EGFL7 protein are increased in blasts of patients with acute myeloid leukemia (AML) compared with normal bone marrow cells. High EGFL7 mRNA expression associates with lower complete remission rates, shorter event-free and shorter overall survival in older (aged ≥60 years) and younger (aged <60 years) patients with cytogenetically normal AML. In addition, AML blasts secrete EGFL7 protein, and those increased levels of EGFL7 protein are found in the sera from AML patients compared with sera from healthy controls. Treatment of patient AML blasts with recombinant EGFL7 (rEGFL7) in vitro leads to increases in leukemic blast cell growth and levels of phosphorylated AKT. These findings demonstrate that increased EGFL7 expression and secretion is a novel autocrine mechanism supporting growth of leukemic blasts in patients with AML.

In this example, the previously uncharacterized clinical and biological role for EGFL7 in AML is reported. Patients with increased EGFL7 mRNA expression had lower complete remission rates, shorter overall and shorter event-free survival demonstrating the clinical relevance of EGFL7 expression in cytogenetically normal AML. This data shows that patient AML blasts are able to synthesize and secrete EGFL7 protein, promoting autocrine blast cell growth.

Acute myeloid leukemia (AML) is a clonal hematopoietic disease characterized by the proliferation of immature blasts in the bone marrow (BM) and blood (1). Genetic alterations including chromosomal translocations and deletions, and gene mutations leading to aberrant downstream target gene expression contribute to AML initiation and maintenance. Previously, increased microRNA-126-3p (miR-126) expression was detected in patients with cytogenetically normal AML (CN-AML) correlated with shorter overall survival (OS). Furthermore, it was found that miR-126 to be essential for leukemia stem cell (LSC) homeostasis and in vivo targeting of miR-126 in a patient-derived xenograft model resulted in prolonged survival in secondary bone marrow transplant (BMT) recipients (2). miR-126 is located within intron 7 of a protein-coding gene known as Epithelial Growth Factor-Like 7 (EGFL7) (3). While an important role for miR-126 in AML biology has been shown (2,4,5), no studies have been performed to understand the prognostic and functional implications of expression of its host gene, EGFL7, in AML.

EGFL7 is a secreted protein of approximately 30 KDa and plays an important physiological role in angiogenesis (6-8). Unlike other angiogenic factors (e.g., VEGF), physiological EGFL7 expression and function has mainly been restricted to the endothelial cells where it regulates survival, migration, and differentiation (6). Aberrant expression of EGFL7 has been shown to be involved in tumor growth and disease progression of several solid tumors, including hepatocellular carcinoma, malignant glioma, and breast, lung, and pancreatic cancers (9), but its role in hematopoietic malignancies is currently unknown. Therefore, the prognostic and biological function of EGFL7 expression in AML was investigated.

It is also shown that EGFL7 mRNA and protein expression are increased in patient AML blasts compared with normal BM mononuclear cells (NBM-MNCs), and that high EGFL7 mRNA expression levels correlate with worse outcome in both younger adults (aged <60 years) and older (aged ≥60 years) patients with CN-AML. Furthermore, AML blasts are capable of secreting EGFL7 protein leading to enhanced leukemic blast growth. This data shows an independent role for EGFL7 in AML but also highlights the importance of this genetic locus in AML via upregulation of both miR-126 and its host gene EGFL7.

Results

Pretreatment Features and Clinical Outcomes Associated with EGFL7 Expression in CN-AML Patients To evaluate the prognostic significance of EGFL7 mRNA expression in CN-AML, one cohort of younger adults (n=374) and one of older (n=198) patients were analyzed, for whom EGFL7 expression was measured by RNA-seq and microarrays, respectively. The median expression value of EGFL7 was used as a cut point to separate the analyzed cohorts into high and low EGFL7 expressers.

Among younger adults, those with high EGFL7 expression (n=187) were more likely to present with lower platelet (P=0.002) and white blood cell counts (P=0.001) and higher percentages of blood blasts (P<0.001) than patients with low EGFL7 expression (n=187). High EGFL7 expressers were also less likely to have leukemic infiltration at extramedullary sites (P=0.02). With regard to molecular characteristics, patients with high EGFL7 expression harbored more frequently double CEBPA (P<0.001) and WT1 (P=0.02) mutations, and less frequently DNMT3A (P=0.004), FLT3-tyrosine kinase domain (FLT3-TKD; P=0.03), IDH2 (P=0.01) and NPM1 (P<0.001) mutations. EGFL7-expresser status associated with significant differences (P=0.04) in the risk stratification of patients according to the European LeukemiaNet (ELN) guidelines (10). Patients with high EGFL7 expression were more frequently classified in the Adverse and less frequently in the Favorable Risk Group than patients with low EGFL7 expression. High EGFL7 expression status associated with high expression of the BAALC (P<0.001), ERG (P<0.001) and MN1 (P<0.001) genes as well as high expression of miR-181a (P<0.001) and miR-155 (P=0.008). High EGFL7 expressers were also more likely to express miR-3151 (P<0.001; Table 2).

Figure 6A:
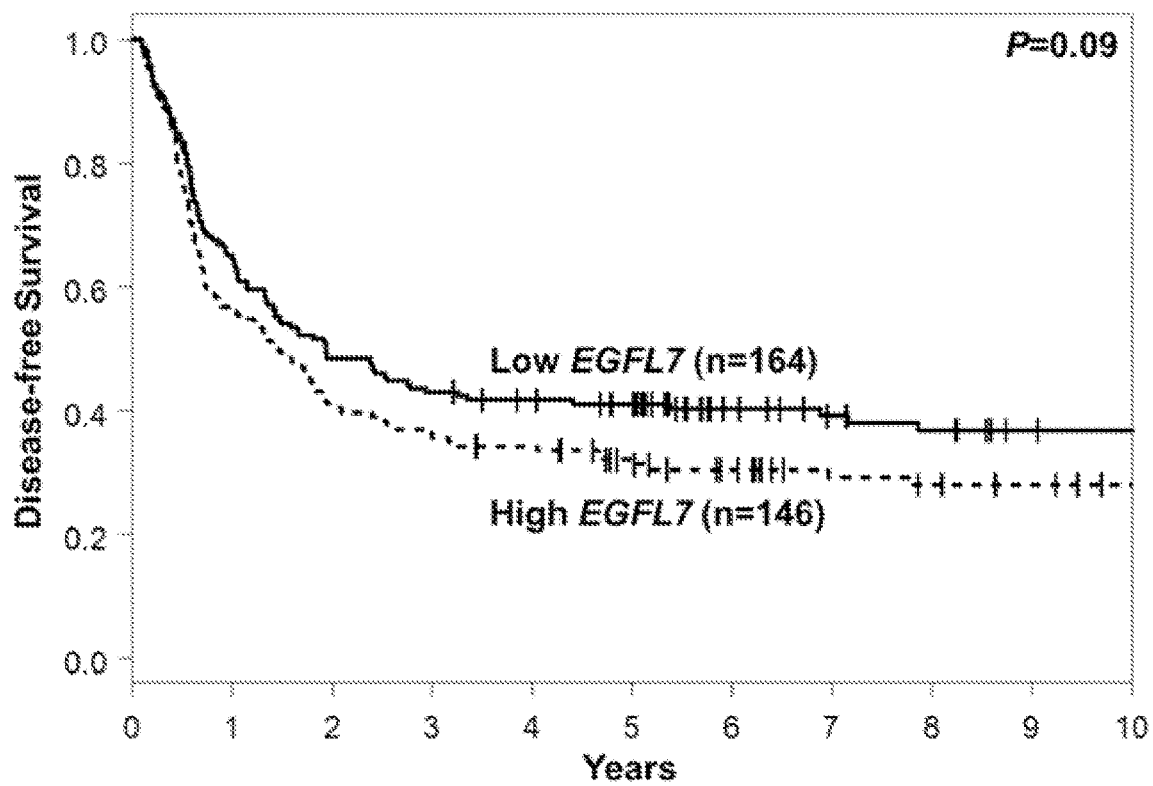
FIG. 6A-6C. Prognostic significance of EGFL7 in younger and older cytogenetically normal (CN) AML patients. Impact of EGFL7 expression levels on disease free-survival (DFS) of (FIG. 6A) younger (aged <60 years) adult patients and (FIG. 6B) older (aged ≥60 years) patients.

With regard to the clinical outcome, high EGFL7 expression status associated with lower complete remission (CR) rate (78% vs. 88%, P=0.01). Patients with high EGFL7 expression showed a trend for shorter disease-free survival (DFS) (P=0.09, 5-year rates, 31% vs. 41% years; FIG. 6A) and had shorter OS (P=0.002, 5-year rates, 34% vs. 49% years; FIG. 1A) in comparison with patients with low EGFL7 expression. High EGFL7 expressers also had shorter event-free survival (EFS) (P=0.005, 5-year rates, 25% vs. 37%; FIG. 1A, Table 3).

In the cohort of older patients, those with high EGFL7 expression harbored more frequently double CEBPA (P=0.01) mutations, FLT3-internal tandem duplications (FLT3-ITD, P<0.001) and RUNX1 mutations (P<0.001), and less frequently NPM1 (P<0.001) and TET2 (P=0.001) mutations. They were also less frequently classified in the Favorable and more frequently in the Intermediate or Adverse Risk Group of the ELN classification than patients with low EGFL7 expression (P<0.001). High EGFL7 expressers were more likely to have high expression of the BAALC (P<0.001), ERG (P<0.001) and MN1 (P<0.001) genes, as well as miR-181a (P=0.02) and miR-155 (P=0.05; Table 4).

Figure 1B:
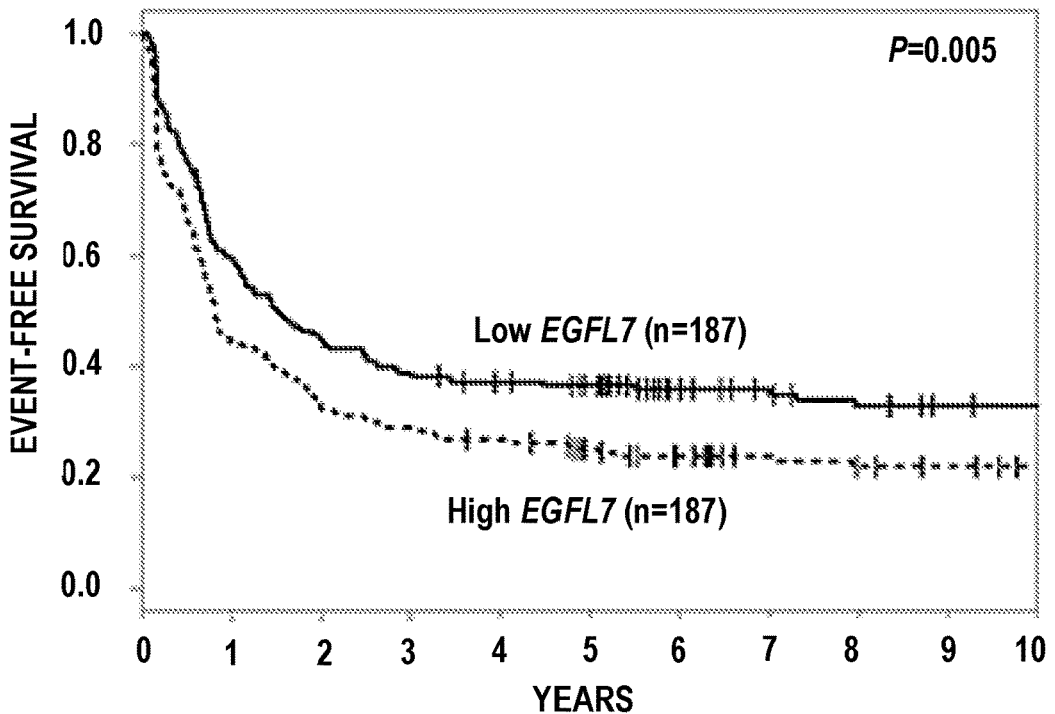
Figure 6B:
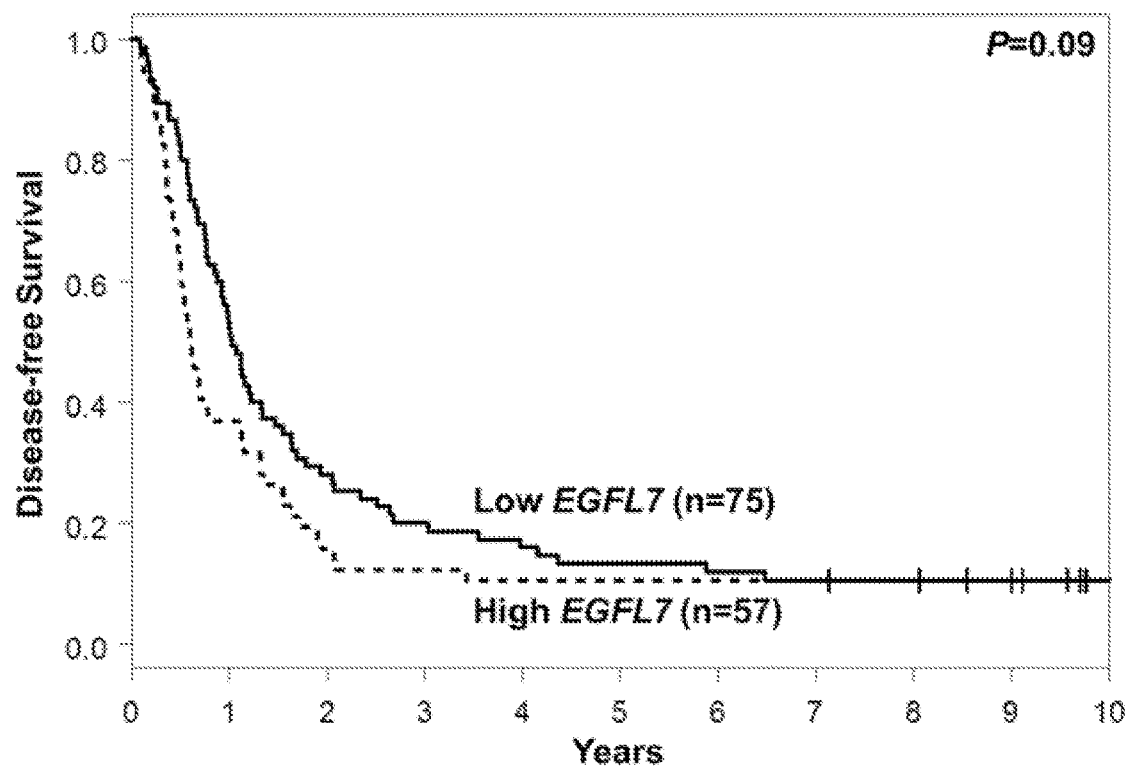

Concerning clinical outcome, older CN-AML patients with high EGFL7 expression were less likely to achieve a CR (58% vs. 76%, P=0.01). High EGFL7 expression status associated with shorter OS (P=0.003, 5-year rates, 9% vs. 19%; FIG. 1B) and EFS (P=0.005, 5-year rates, 6% vs. 10%; FIG. 1B), whereas it showed a trend for association with shorter DFS (P=0.09, 5-year rates, 11% vs. 13%; FIG. 6B, Table 5).

It was hypothesized that the epigenetic regulation of EGFL7 could also provide prognostic information and, thus the EGFL7 promoter methylation status was evaluated in a subgroup of older CN-AML patients (n=126) using a methylated DNA capture technique, followed by next generation sequencing (MethylCap-Seq), as described previously (11). The median value of EGFL7 promoter methylation was used to dissect the cohort and it was found that patients with high EGFL7 promoter methylation showed a trend towards higher CR rates (73% vs 56%, P=0.06) and had longer OS (P=0.05) than patients with low EGFL7 promoter methylation. There was also a trend for longer EFS in patients with high EGFL7 promoter methylation (P=0.09) and no significant association of DFS with EGFL7 promoter methylation status.

Figure 1C:
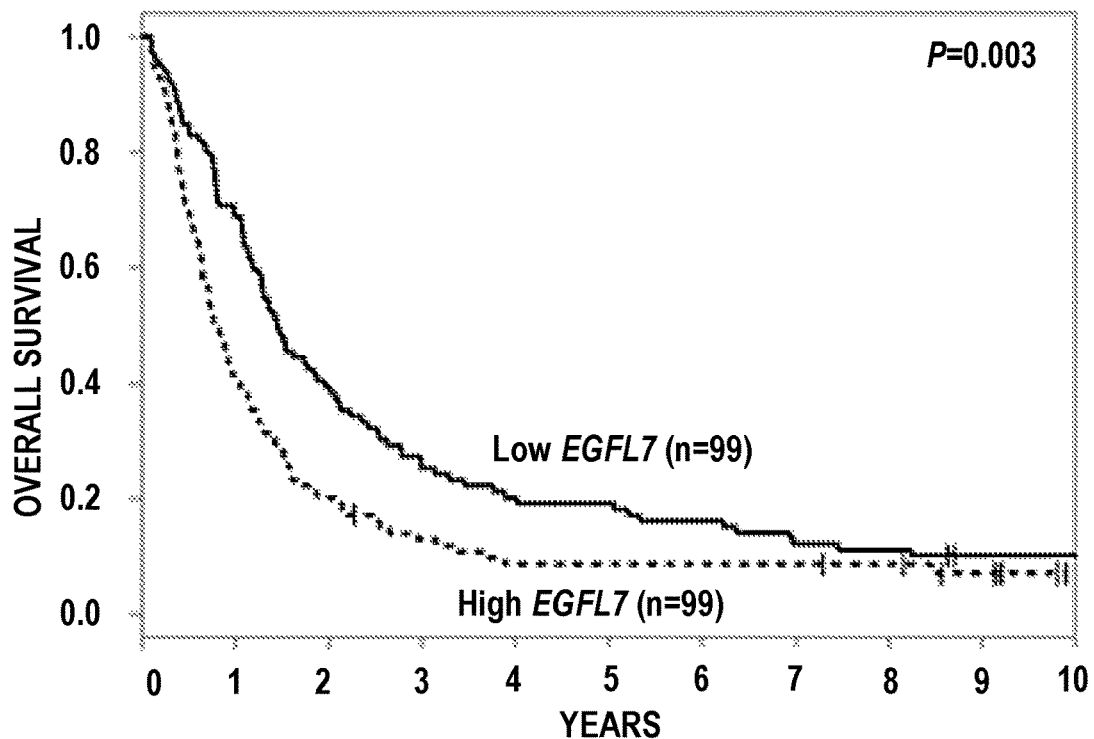
Figure 1D:
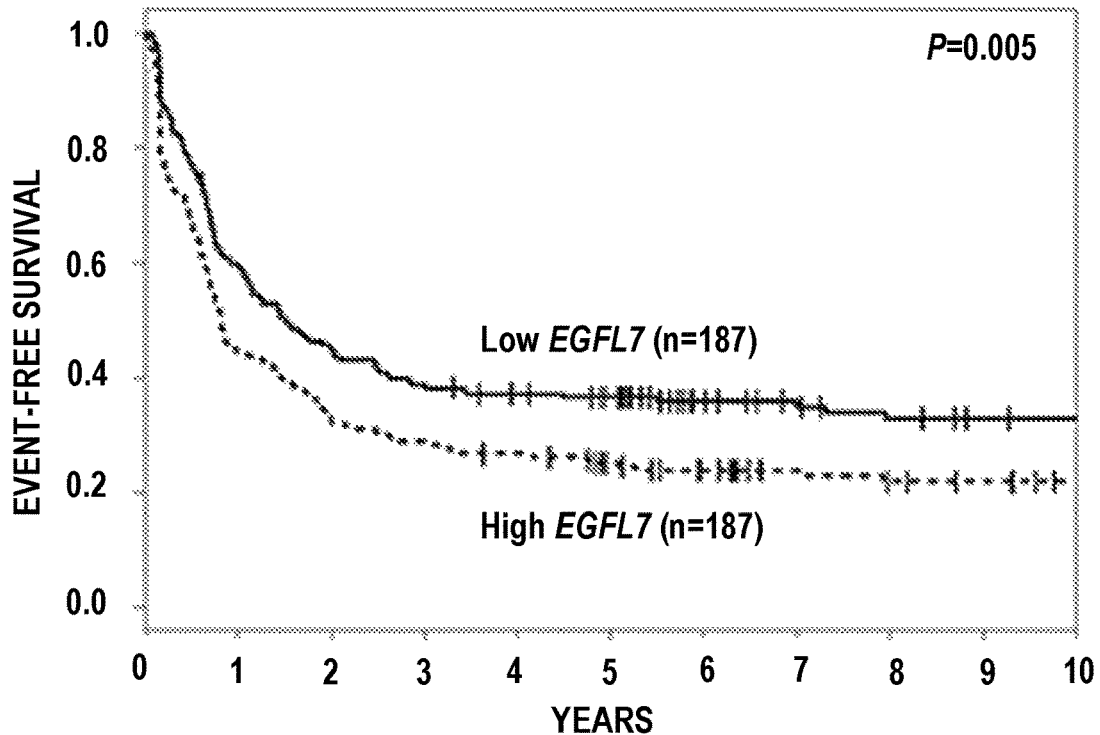
Figure 1E:
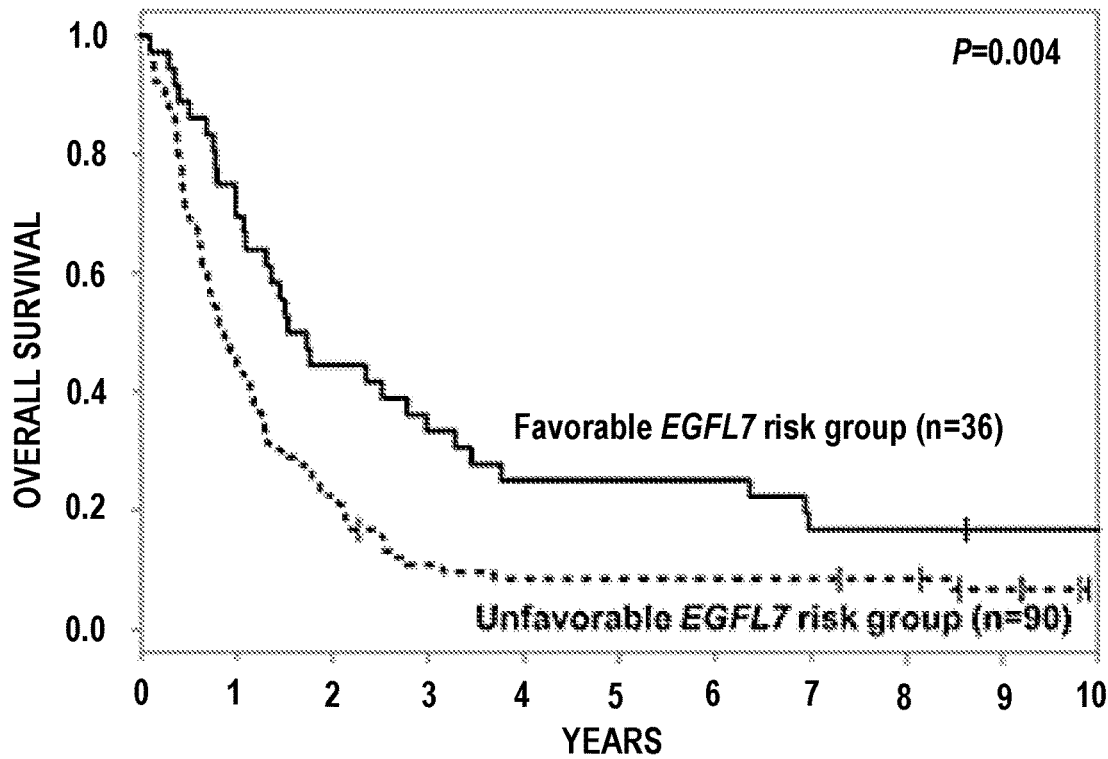
Figure 1F:
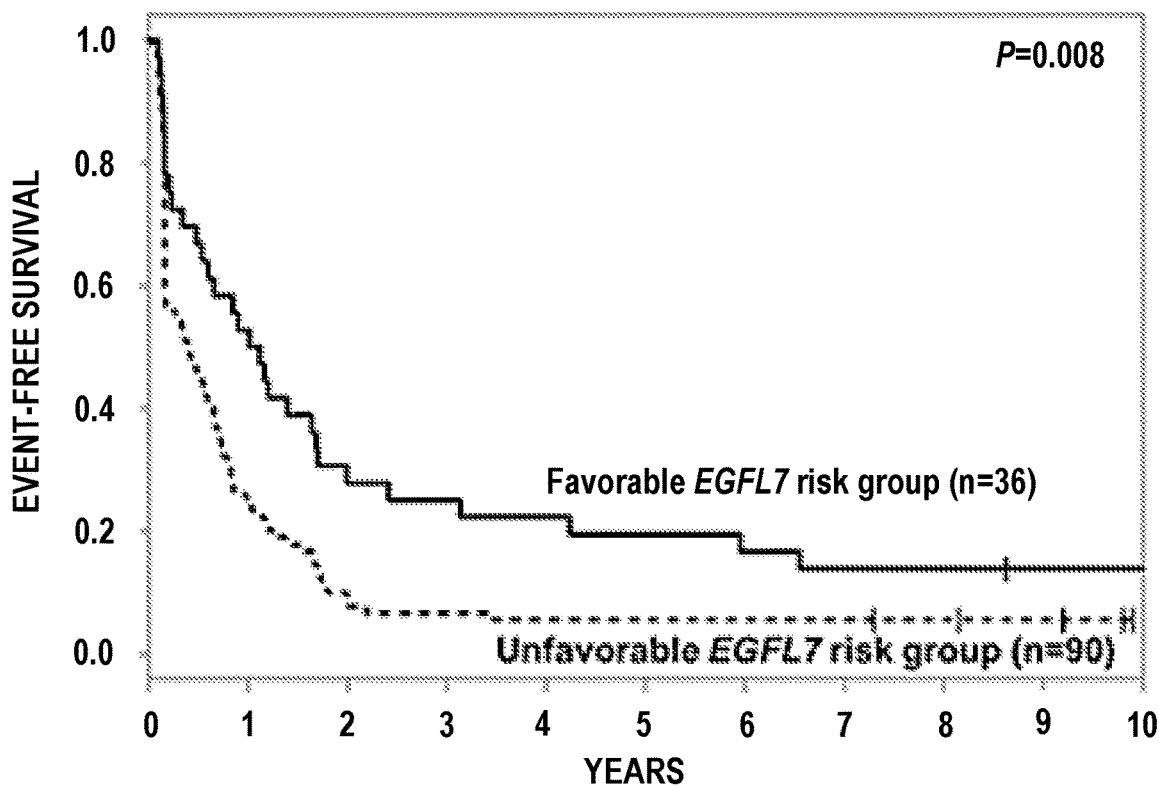
Figure 6C:
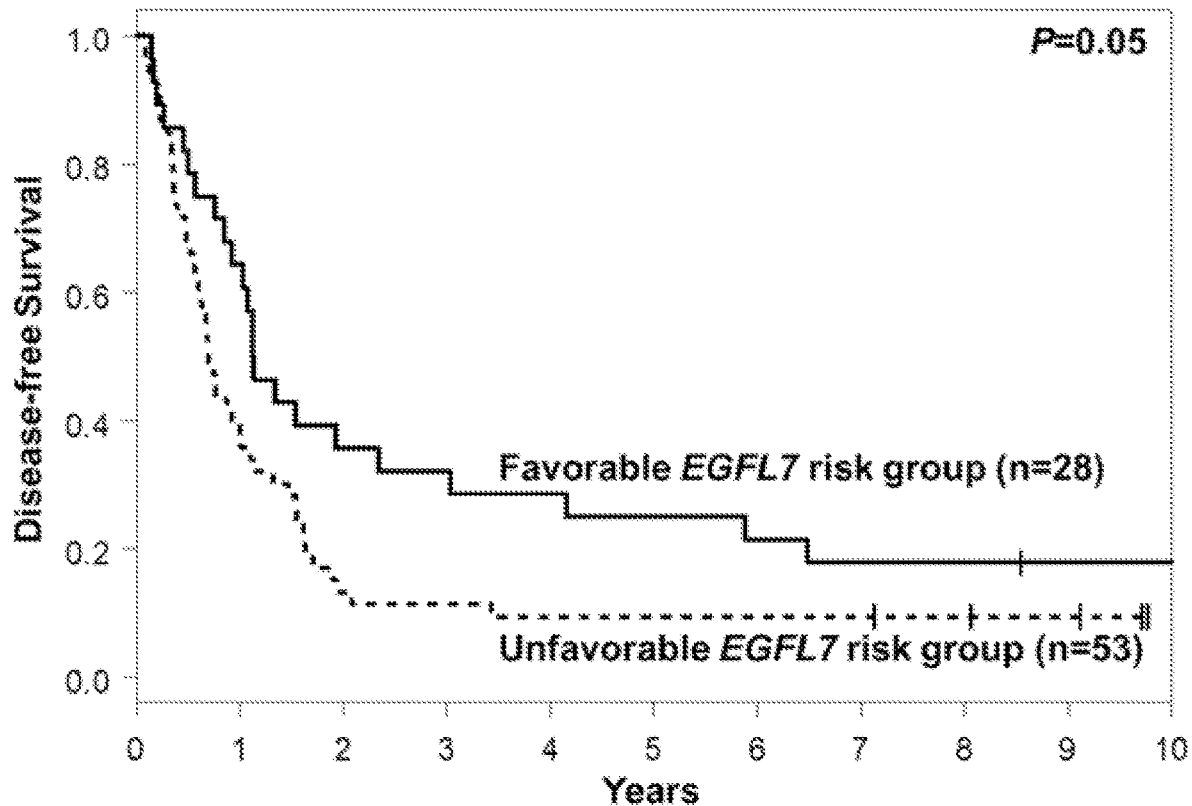

The combination of high EGFL7 promoter methylation with low EGFL7 expression identified a subset of older CN-AML patients with better outcome (n=36, hereafter referred to as EGFL7 favorable risk group) when compared with the remaining patients of the cohort (n=90, EGFL7 unfavorable risk group). Patients in the EGFL7 favorable risk group showed a trend for higher CR rates (78% vs. 59%, P=0.06) and had longer DFS (P=0.05; FIG. 6C). Five years after diagnosis, 25% of these patients remained alive and leukemia-free, in contrast to only 9% of patients in the EGFL7 unfavorable risk group. Patients in the EGFL7 favorable risk group also had longer OS (P=0.004, 5-year rates, 25% vs. 4%) and EFS (P=0.008, 5-year rates, 19% vs. 6%) than those in the EGFL7 unfavorable risk group (FIG. 1C, Table 6).

In multivariable analyses of older CN-AML patients, EGFL7 favorable risk group was shown to be an independent marker of longer DFS (P=0.03), after adjusting for extramedullary involvement (P=0.02), and of longer OS (P<0.001), after adjusting for miR-155 expression status (P<0.001) and platelet counts (P<0.001; Table 1). Because of the relatively small number of patients in the EGFL7 favorable risk group, a final model could not be constructed for EFS. However, three separate three-variable models were generated, in which the association of favorable EGFL7 status with longer EFS remained significant after adjusting for other co-variates (P=0.002, P<0.001 and P<0.001, Table 7). With regard to CR, EGFL7 risk group status did not remain significant in multivariable analysis.

EGFL7 Expression in AML

Figure 2A:
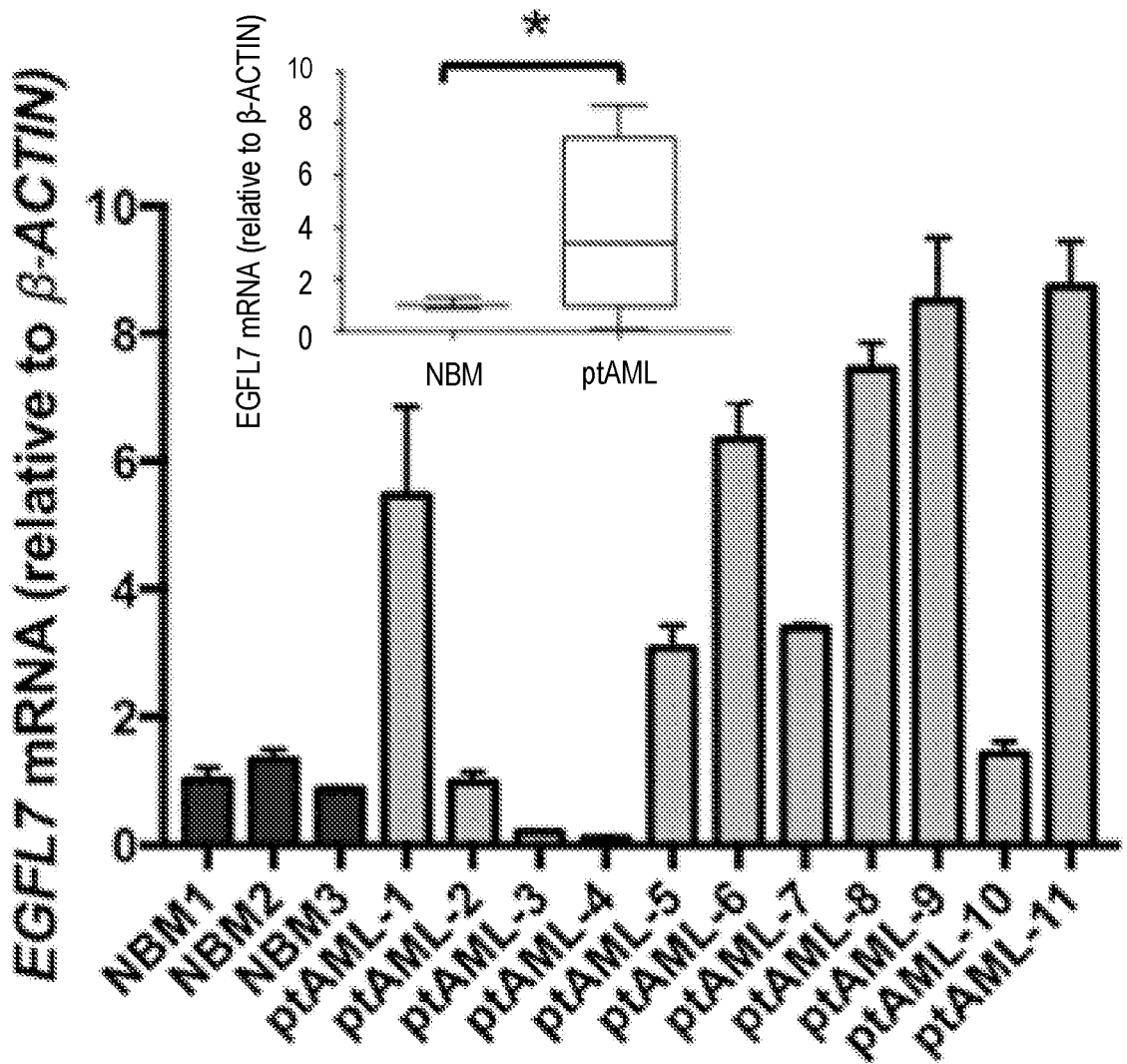
FIG. 2A-2E. EGFL7 is upregulated in human and mouse acute myeloid leukemia (AML) cells.
Figure 2B:
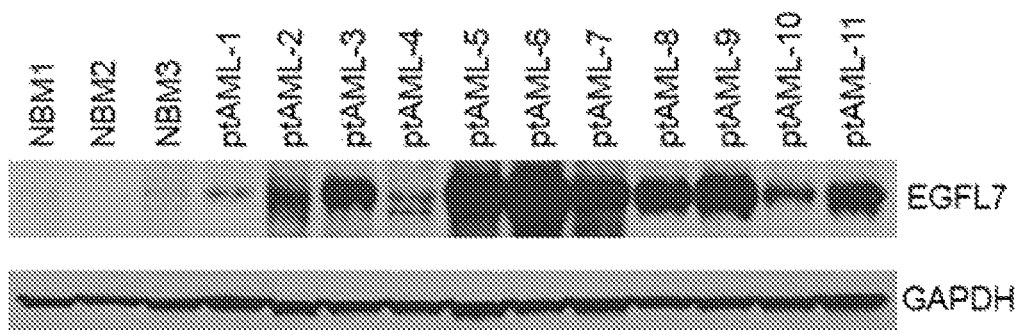
Figure 2C:
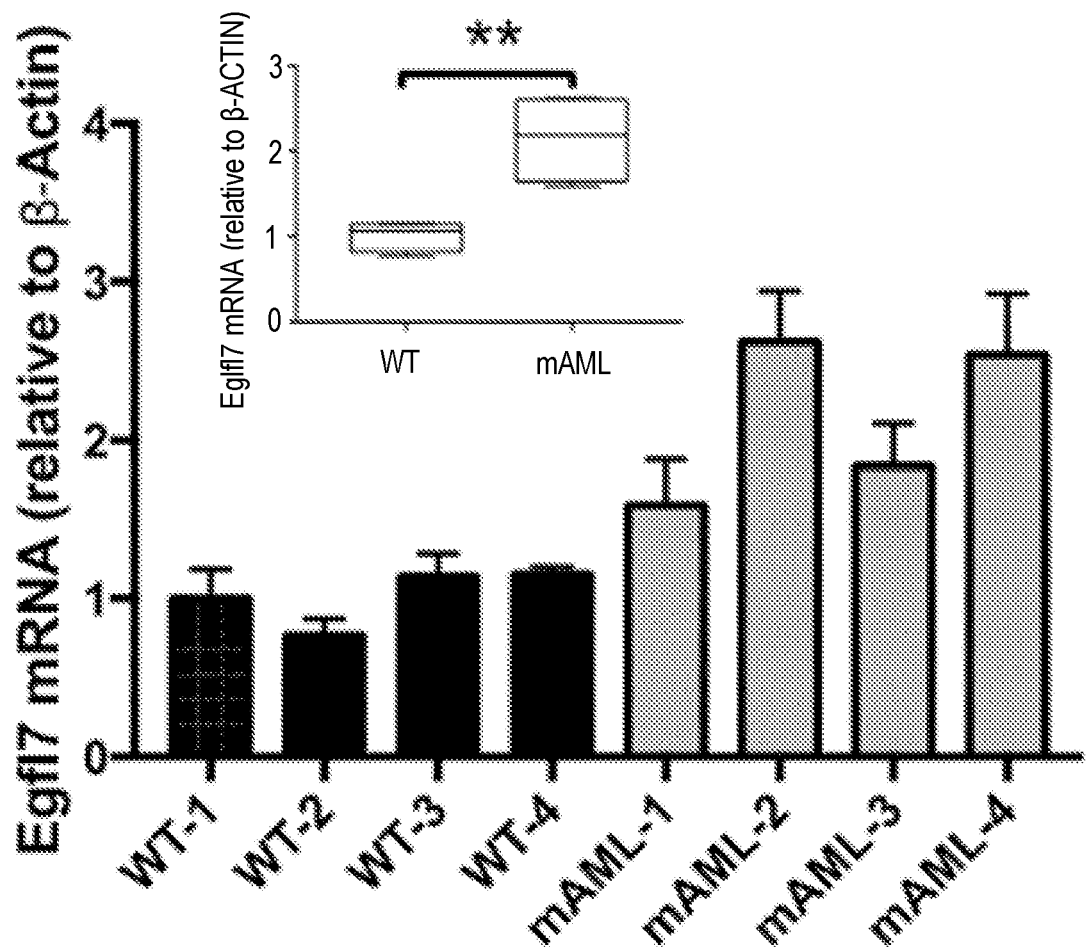
Figure 2D:
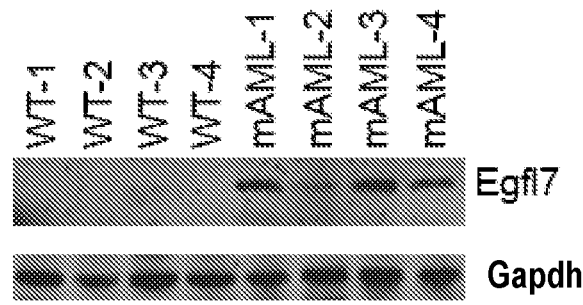
Figure 2E:
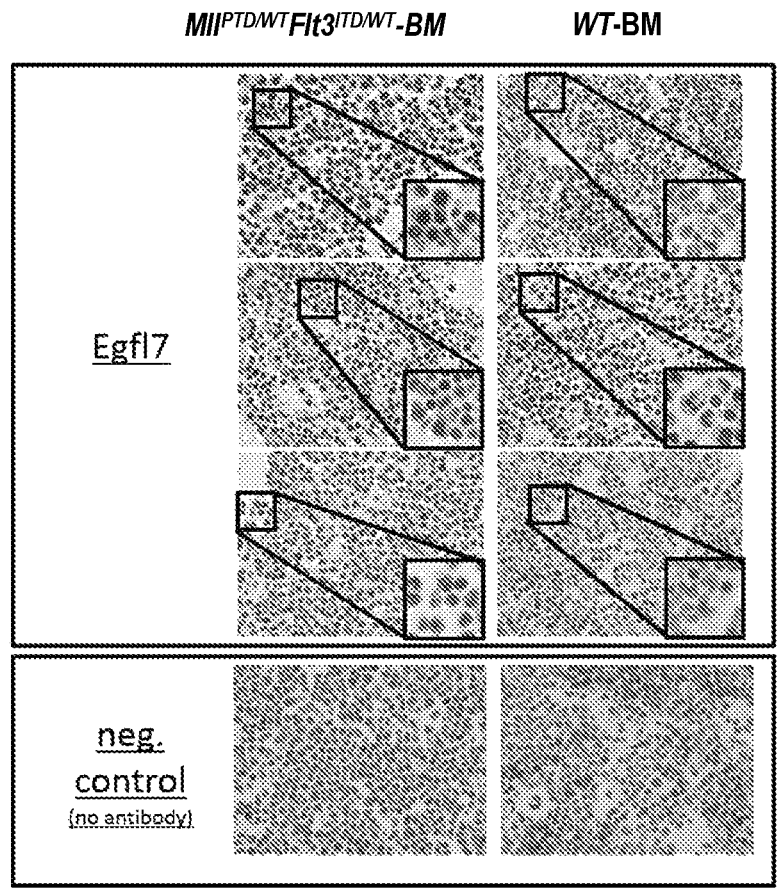

To further validate the RNA-seq and microarray data, EGFL7 mRNA and protein were measured in patient AML blasts and NBM-MNCs using real-time PCR (RT-PCR) and western blotting, respectively. As shown in FIGS. 2A and 2B, higher levels of EGFL7 mRNA and protein were observed in AML blasts from the majority of patients analyzed compared with NBM-MNCs. The Egfl7 expression in the $Mll^{PTD/WT}Flt3^{ITD/WT}$ mouse model of CN-AML (12) was also investigated and compared it with Egfl7 expression in wild-type (WT) murine controls. Significant increases in the Egfl7 mRNA and Egfl7 protein in the BM of $Mll^{PTD/WT}Flt3^{ITD/WT}$ leukemic blasts compared with WT NBM-MNCs (FIGS. 2C and 2D) were found. To further evaluate the expression of Egfl7 protein in AML, immunohistochemistry was performed for Egfl7 in the $Mll^{PTD/WT}Flt3^{ITD/WT}$ AML compared with WT murine BM. Substantial increases in Egfl7 were found in samples of $Mll^{PTD/WT}Flt3^{ITD/WT}$ leukemic BM compared with normal controls (FIG. 2E).

EGFL7 Expression and Secretion by AML Blasts

Figure 3A:
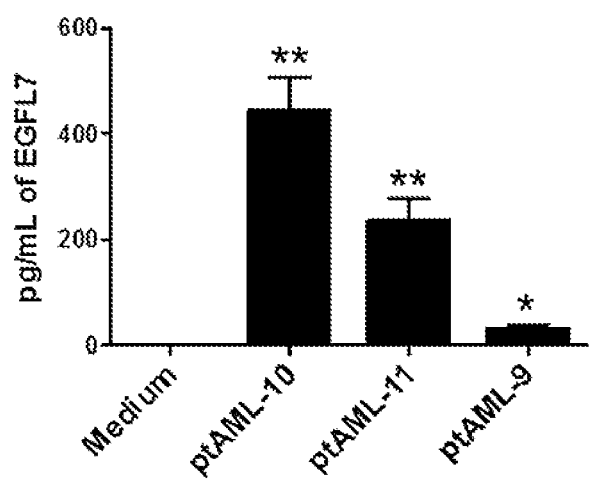
FIG. 3A-3D. EGFL7 is a secreted protein and increased in the serum of some acute myeloid (AML) patients.
Figure 3B:
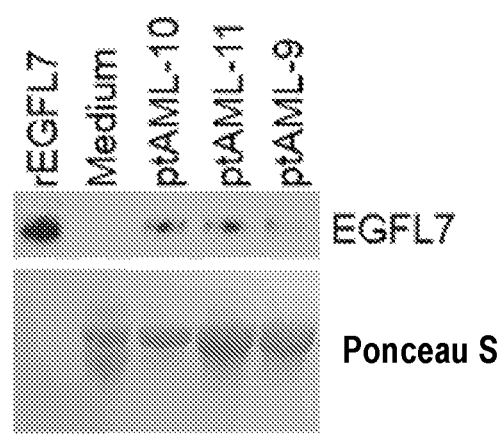
Figure 3C:
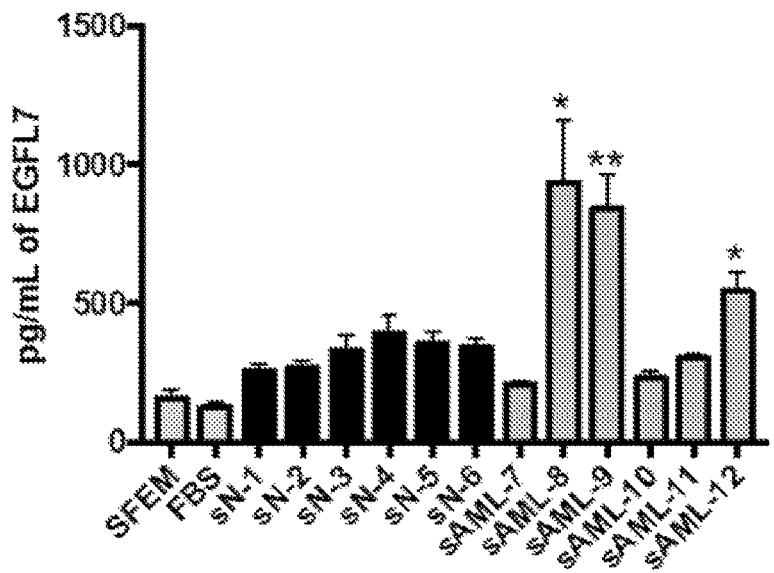
Figure 3D:
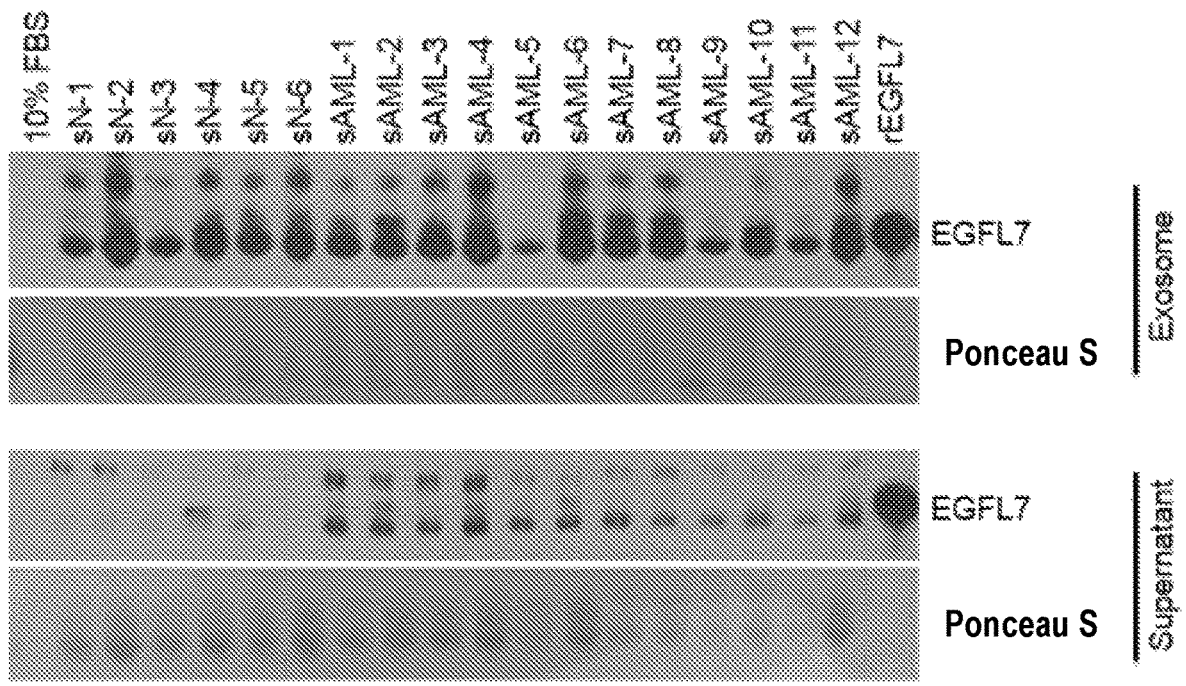

EGFL7 is normally expressed and secreted by endothelial cells to promote angiogenesis. It was therefore sought to determine if AML blasts also acquired the ability to synthesize and secrete EGFL7 protein. Blasts from three patients with AML were cultured for 24 hours in media with 10% fetal bovine serum (FBS) and cytokines. EGFL7 levels were measured in the media using an ELISA assay. As shown in FIG. 3A, significantly increased levels of EGFL7 protein were found in the media from the AML blasts compared with media from wells without blasts. These results were confirmed using western blotting (FIG. 3B). Next, EGFL7 protein was measured in the serum from healthy donors (n=6) and AML patients (n=6) using an ELISA assay. Significant increases in the level of EGFL7 were found in three of the six samples from the AML patients compared with normal controls (FIG. 3C). In an effort to validate these results using whole serum and western blotting, it was found that the serum was highly saturated with protein and interfered with resolution of the blot. After separating the serum into the exosome-containing and supernatant fractions, variable, high levels of EGFL7 were found in the exosomes in both normal and AML serum; however, there was substantially more 'free' non-exosomal EGFL7 in the supernatant fraction in the AML patients than in normal controls (FIG. 3D).

EGFL7 Stimulation Leads to Enhanced AML Blast Cell Growth

Figure 4A:
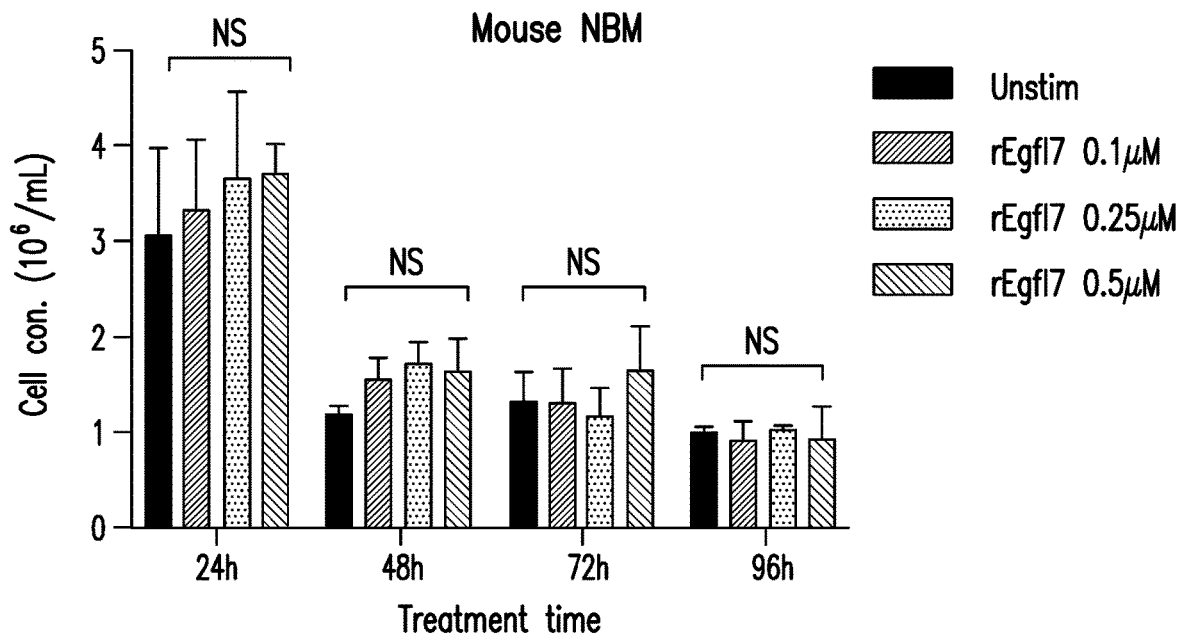
FIG. 4A-4E. EGFL7 stimulates the proliferation of human and mouse acute myeloid leukemia (AML cells). Bone marrow cells from wild-type (WT) mice (FIG. 4A), and $Mll^{PTD/WT}Flt3^{ITD/WT}$ mice (FIG. 4B), were treated without (Unstim) or with 0.1, 0.25, or 0.5 μM recombinant mouse Egfl7 (rEgfl7) in IMDM medium+2% bovine serum albumin (BSA) for 24, 48, 72 and 96 hours. At the indicated time points, the number of viable cells was determined by trypan blue dye exclusion assay. Each condition was repeated in triplicate. NS indicates not significant, * indicates P<0.05,  indicates P<0.01.
Figure 4B:
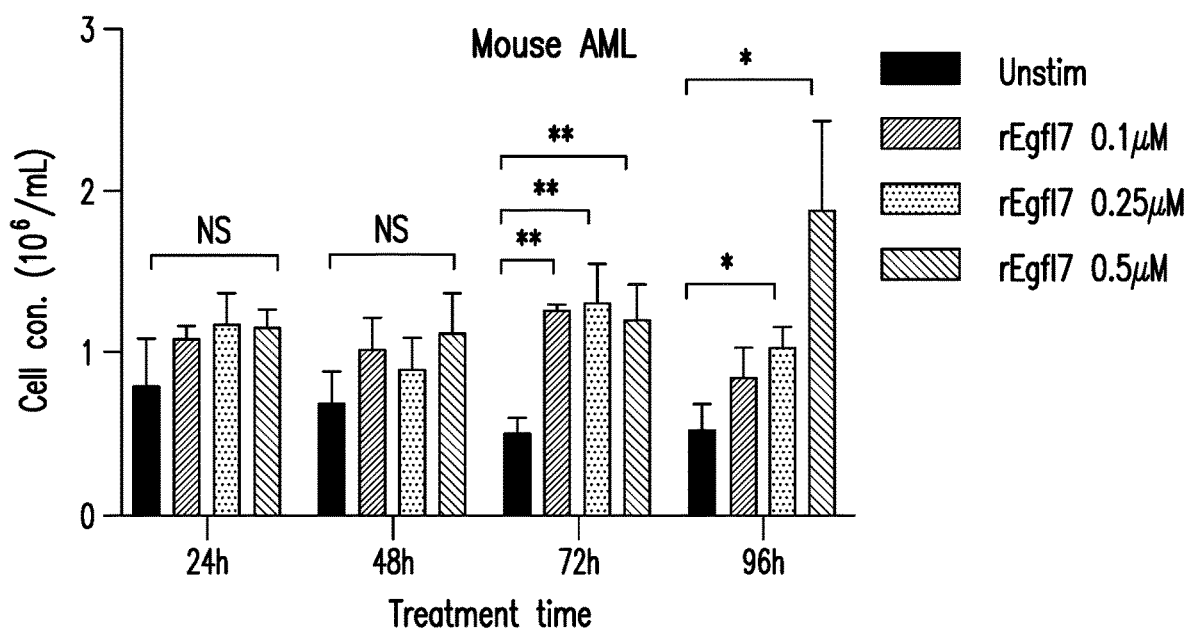
Figure 4C:
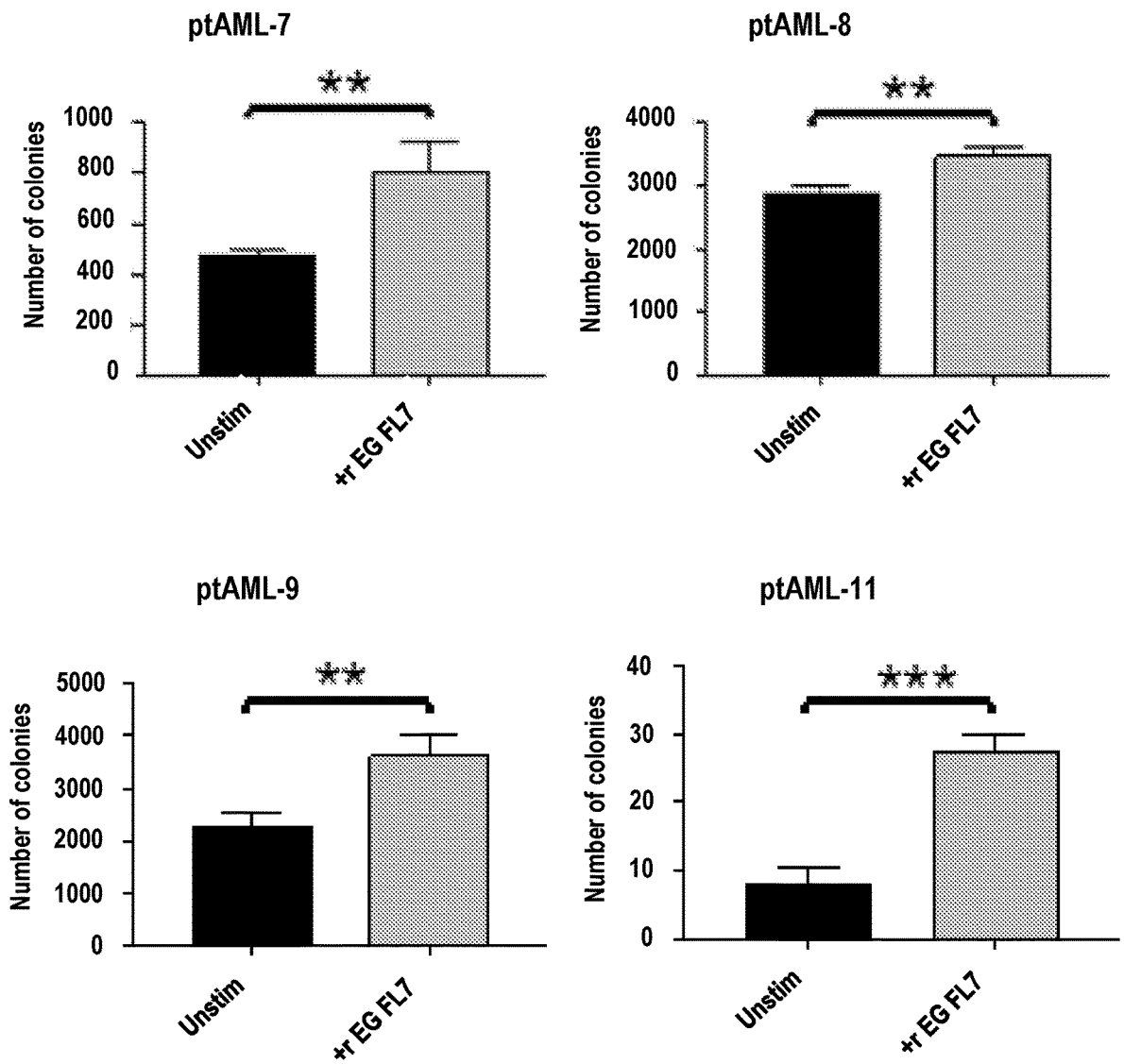
Figure 4D:
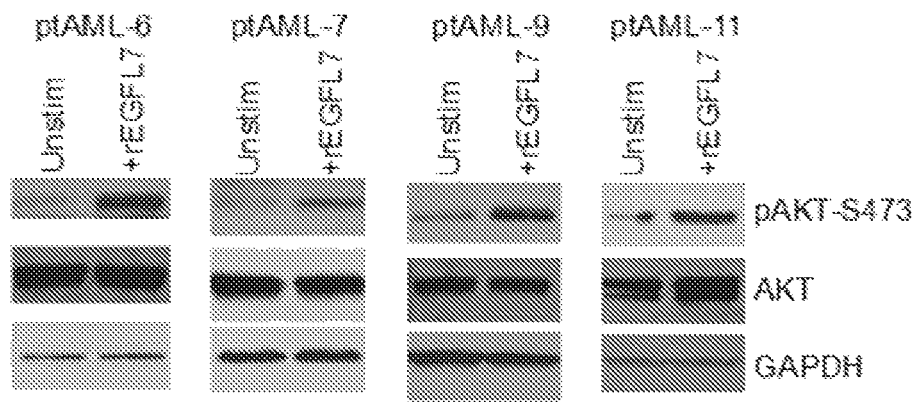
Figure 4E:
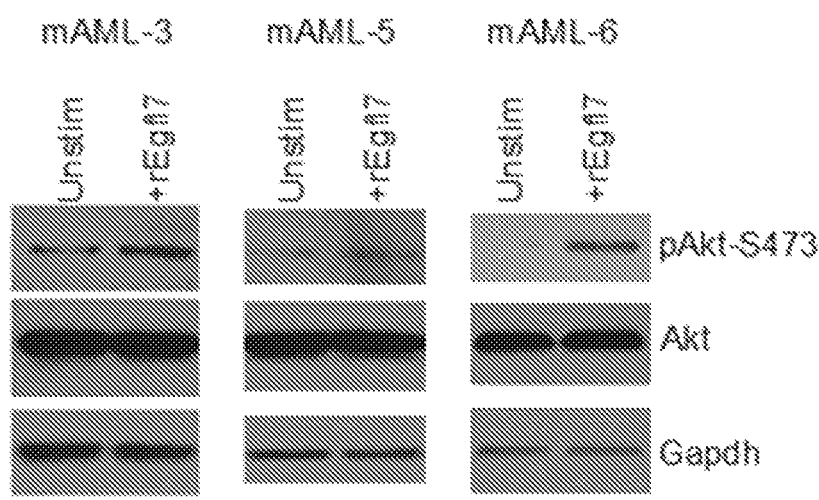
Figure 7A:
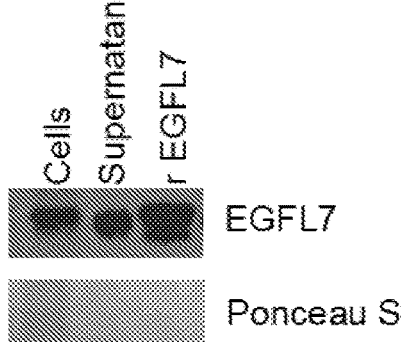
FIG. 7A-7D. Recombinant EGFL7 treatment increases proliferation of the Kasumi-1 AML cell line.
Figure 7B:
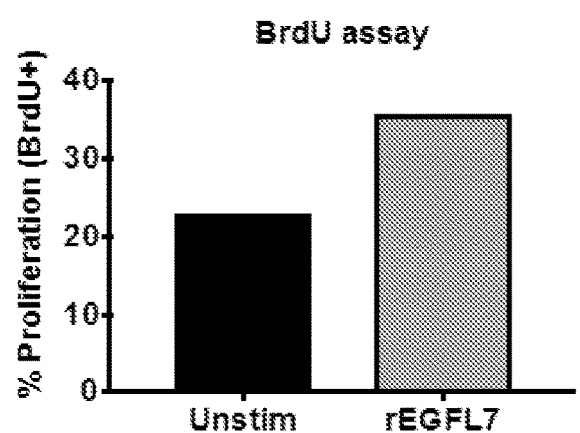
Figure 7C:
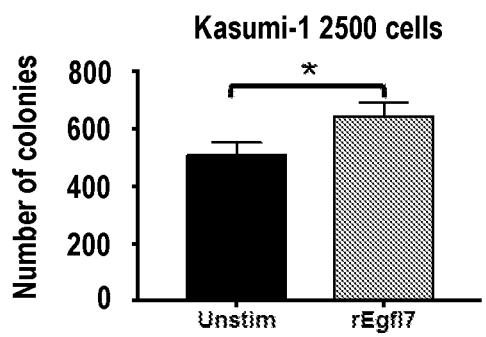
Figure 7D:
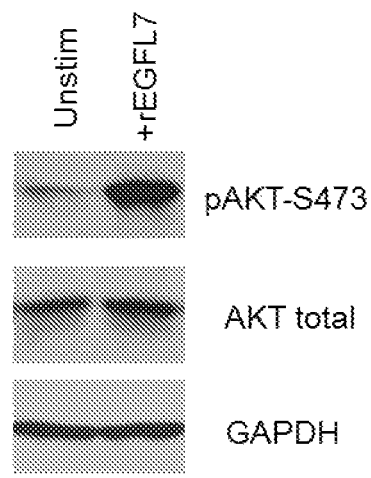

To compare the effect of Egfl7 protein on normal murine BM MNCs with its effect on murine AML blasts, blasts were cultured in minimal media [SFEM+2% Bovine Serum Albumin (BSA)] and then stimulated them with recombinant Egfl7 (rEgfl7). Although the normal mouse BM did not expand at any time point (FIG. 4A), significant expansion of the murine AML blasts cells was found at 72 and 96 hours post-stimulation with rEgfl7 (FIG. 4B). The stimulatory effect of EGFL7 on growth of patient human AML blasts using colony forming unit (CFU) assays was further validated. An increase in the number of CFUs was found when rEGFL7 was added to the methylcellulose (FIG. 4C). In addition, rEGFL7 treatment of the Kasumi-1 AML cell line, which expresses high levels of EGFL7 (15) (FIG. 7A) led to an increase in fraction of proliferating cells, as measured by BrdU incorporation (FIG. 7B) and in the number of colonies formed in CFU assays (FIG. 7C). In agreement with the increased cell growth in response to EGFL7, consistent increases were found in phosphorylated AKT (pAKT) in human (FIG. 4D) and mouse (FIG. 4E) AML cells, as well as Kasumi-1 cells (FIG. 7D). These findings are consistent with other studies demonstrating increased levels of pAKT in response to EGFL7 stimulation (13,14).

EGFL7 Silencing Reduces AML Blast Cell Growth

Figure 8A:
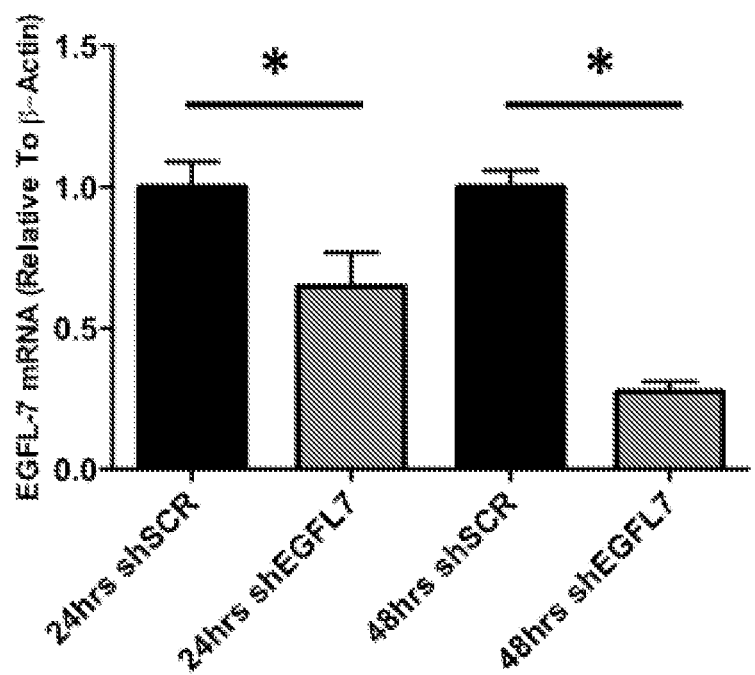
(FIG. 8A) EGFL7 knock-down, as evaluated by real-time PCR 24 and 48 hours after sorting of cells. * indicates P<0.05.
Figure 8B:
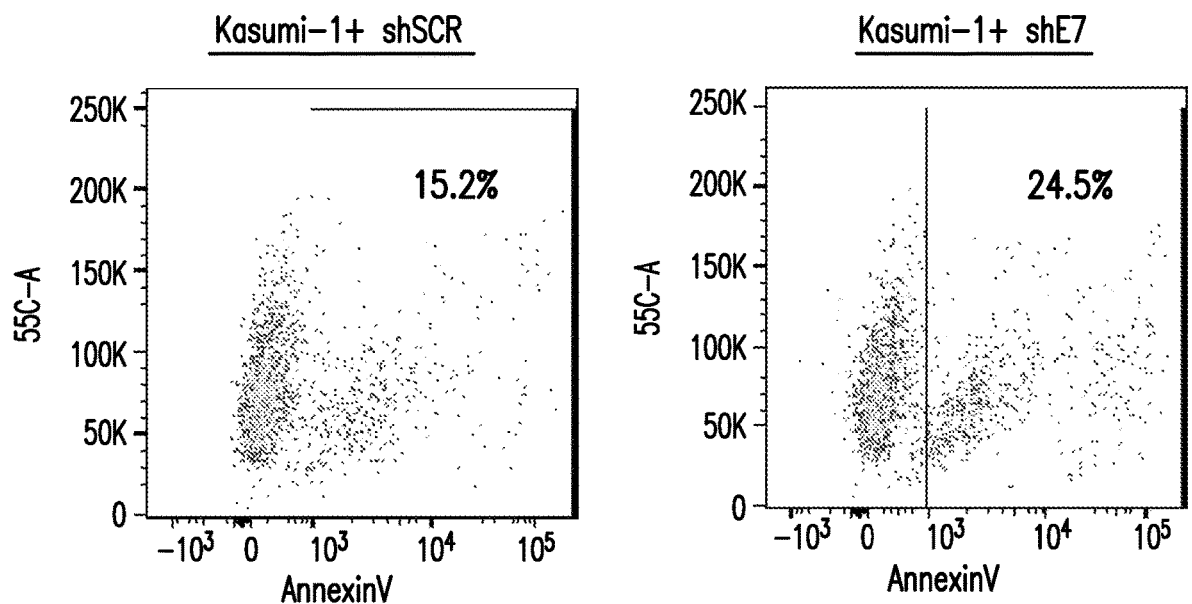
(FIG. 8B, FIG. 8C) Apoptosis was assessed by FACS using AnnexinV staining, 96 h after the sorting of cells.
Figure 8C:
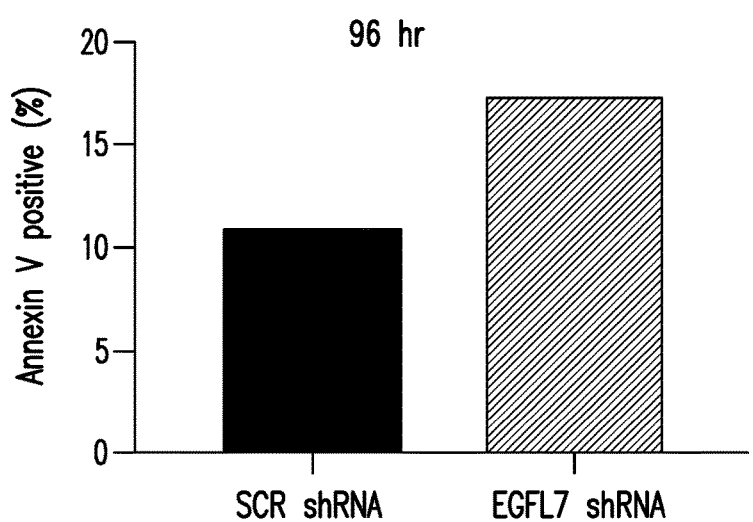

Next it was sought to determine whether knock-down of EGFL7 had a growth inhibitory effect on AML blasts. Apoptosis/proliferation of transduced patient AML cells with lentivirus was not assessed due to the low viability of these cells after lentiviral transduction even in the non-targeting scramble (shSCR) controls. Therefore, the Kasumi-1 cell line was transduced with either EGFL7-silencing (shEGFL7) or shSCR lentiviral vectors. EGFL7 knock-down in these cells was confirmed by RT-PCR (FIG. 8A). It was found that cells transduced with shEGFL7 had increases in apoptosis compared to shSCR controls (FIGS. 8B and 8C).

Figure 5:
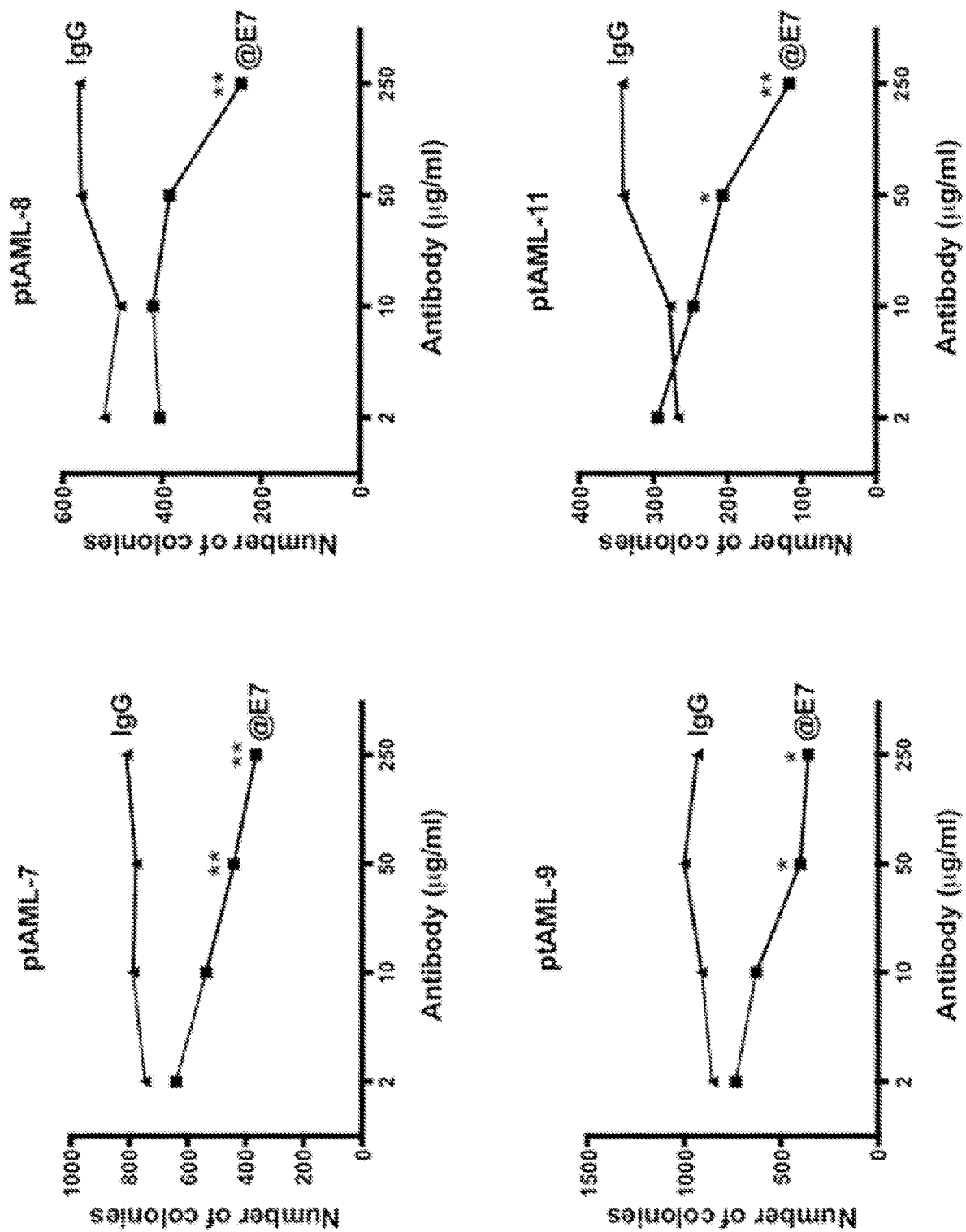
FIG. 5. Anti-EGFL7 antibody inhibits the growth of human AML blasts. 0.4 million human AML blasts from four different patients were treated with 2, 10, 50, or 250 μg/ml of anti-EGFL7 antibody (@E7) or normal human IgG in SFEM medium containing 10% FBS and cytokines for 2 h. 20,000 cells were mixed with methylcellulose medium and plated onto 2 cm dishes for 10 days. The number of colonies with more than 50 cells was counted under a light microscope. Each experiment was conducted in triplicates. The average number of colonies is shown. * indicates P<0.05, ** indicates P<0.01.

To further evaluate the effect and therapeutic potential of EGFL7-blockade on AML blasts, experiments were performed with an antibody that binds to the EGFL7 protein and inhibits its downstream effects. Treatment of human AML blasts with increasing concentrations of the anti-EGFL7 blocking antibody, led to significant decreases in cell growth, as assessed by the numbers of formed colonies in CFU assays, compared to normal IgG control treated blasts (FIG. 5).

Figure 9:
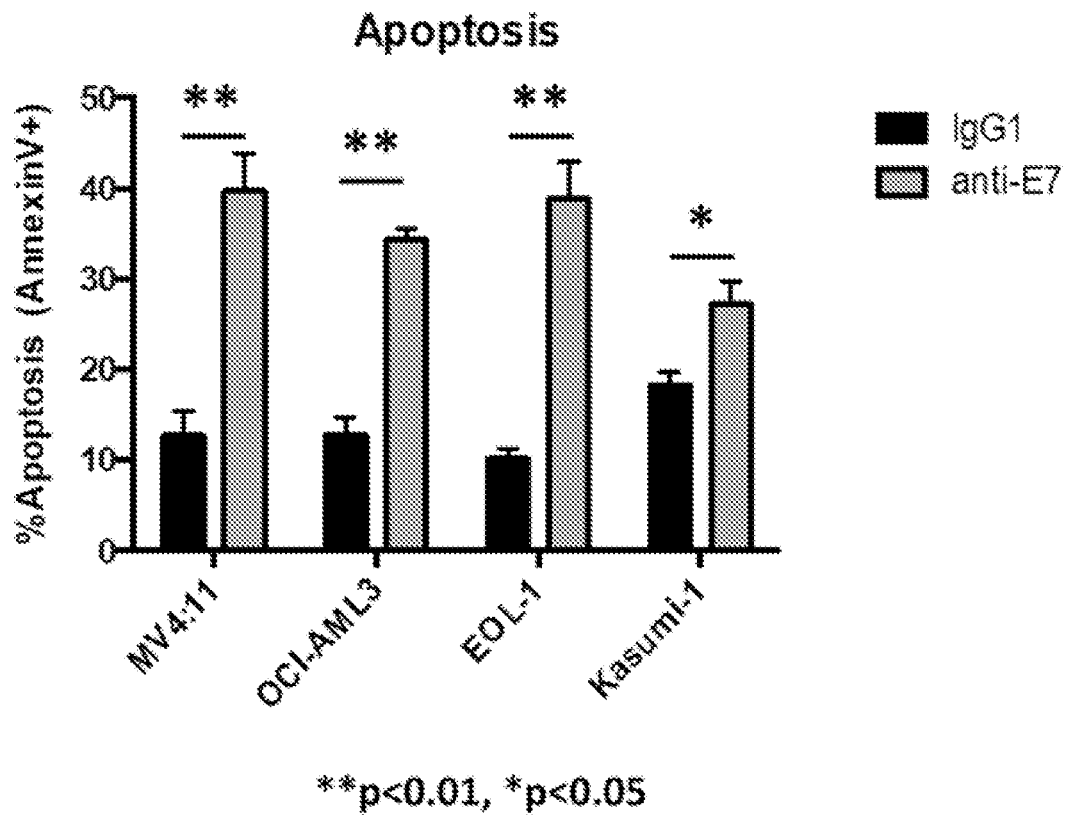
FIG. 9. Increased apoptosis in AML cell lines treated with anti-EGFL7. Forty-eight hours after IgG control vs. @E7 antibody treatment (50 µg/ml) of AML cell lines apoptosis was evaluated by AnnexinV/7AAD staining. * indicates P<0.05, ** indicates P<0.01.
Figure 10:
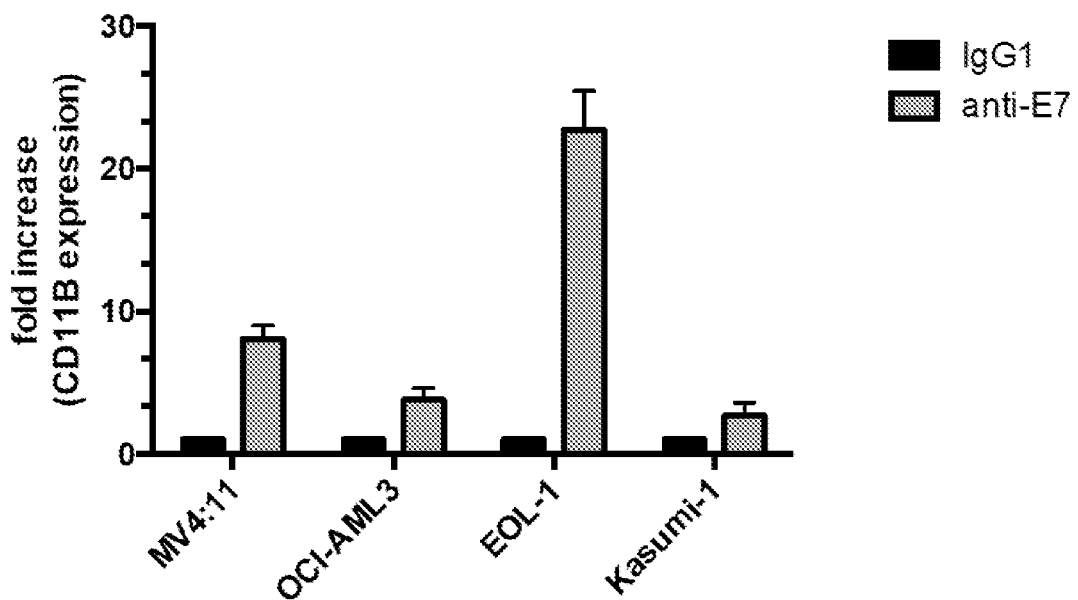
FIG. 10. Induced differentiation in AML cell lines treated with anti-EGFL7. Differentiation analysis was evaluated by CD11b expression. CD11b is depicted as the ratio of the CD11b expression value in the @E7 treated samples to CD11b expression value of the IgG-treated controls. * indicates P<0.05, ** indicates P<0.01.

As shown in FIG. 9, anti-EGFL7 antibody treatment increased apoptosis is different AML cell lines. Finally, as seen in FIG. 10, increased differentiation of these cell lines was also seen upon treatment with anti-EGFL7 antibody.

Discussion

EGFL7 is a secreted protein with a well characterized role in the physiology of angiogenesis and the pathology of certain solid tumors (6-9). The significance of miR-126 has previously been reported (2,4,5), which is located in intron 7 of the EGFL7 gene, in AML but an independent role of EGFL7 in this disease has not to date been described. Herein, a set of younger adults and a set of older patients with CN-AML were analyzed in order to evaluate the prognostic and biologic significance of EGFL7 expression. It was found that high EGFL7 expression associates with worse outcome in both of the studied cohorts. It was also found that in the older patients, the combination of high EGFL7 promoter methylation and low EGFL7 expression identified a subset of patients with favorable prognosis, independently of other prognostic co-variates.

While it seems reasonable that the expression levels of miR-126 and EGFL7 are regulated by the same mechanisms, including methylation, as they stem from the same transcript mechanistic studies indicate that these genes have different effector functions. EGFL7 is a protein that is secreted by the AML blasts and is capable of directly inducing enhanced cell growth. Treatment of patient AML samples as well as cell-lines with recombinant EGFL7 protein led to markedly increased levels of pAKT, a key regulator of cell proliferation. Concordantly, EGFL7 treatment increased the proliferating fraction as well as the number of colonies formed by AML cells. In contrast to this, no effects on cell proliferation were observed when miR-126 expression was modulated in AML bulk blasts. Instead, miR-126 was found to be essential for LSC homeostasis (2). Whether EGFL7 also has a role in LSCs, dependent or independent from miR-126, has not yet been determined.

Understanding the individual as well as combinatorial roles of EGFL7 and miR-126 in leukemogenesis could contribute significantly to more efficient therapeutic approaches in patients with aberrant activation of the EGFL7 locus. This data shows that EGFL7 represents a novel therapeutic target in AML. It was found that lentiviral knock-down of EGFL7 resulted in increased apoptosis of AML cells. It was also shown that human BM cells from healthy donors express relatively low levels of EGFL7. Thus blocking antibodies, capable of inhibiting EGFL7 activity specifically on AML blasts can have a therapeutic effect on patients with increased EGFL7 expression, while preserving normal BM populations. In patients with concomitant aberrant overexpression of miR-126, EGFL7-blockade could be combined with therapeutic interventions to down-regulate miR-126, in order to additionally target the LSC compartment. The feasibility of therapeutic manipulation of miR-126 with nanoparticle-conjugated oligonucleotides (NP-antagomiR-126) in a pre-clinical model was previously shown (2). In this sense, combining EGFL7-inhibition with NP-antagomiR-126 therapies can improve the treatment of AML patients, as blocking the growth promoting functions of EGFL7 on bulk blasts would be combined with the targeting of the therapy resistant LSCs by the NP-antagomiR-126.

In conclusion, these results demonstrate the clinical and biological relevance of EGFL7 expression in AML. It was found that expression levels of EGFL7 are prognostic in CN-AML patients, and that patient AML blasts are able to secrete EGFL7 protein and promote in an autocrine fashion the leukemic cell growth.

Methods

Patient set.

For survival analyses, pretreatment BM or blood samples were obtained from 572 adult patients (374 younger patients aged 17-59 years and 198 older patients aged 60-83 years) with de novo cytogenetically normal acute myeloid leukemia (CN-AML), who received intensive cytarabine/anthracycline-based first-line therapy on Cancer and Leukemia Group B (CALGB)/Alliance for Clinical Trials in Oncology (Alliance) trials, and were alive 30 days after initiation of treatment. Per protocol, no patient received allogeneic stem cell transplantation in first CR. All patients provided written informed consent, and all study protocols were in accordance with the Declaration of Helsinki and approved by institutional review boards at each center.

Cytogenetic and molecular analyses.

Cytogenetic analyses were performed in CALGB/Alliance-approved institutional laboratories and results confirmed by central karyotype review (16). The diagnosis of a normal karyotype was based on ≥20 metaphase cells analyzed in BM specimens subjected to short-term (24- or 48-hour) unstimulated cultures.

In the group of younger (n=374) and a subset of older CN-AML patients (n=154), targeted amplicon sequencing using the Miseq platform (Illumina) was applied to analyze DNA samples for the presence of gene mutations that are established prognosticators in CN-AML [i.e., mutations in the ASXL1, DNMT3A (R882 and non-R882), IDH1, IDH2 (R140 and R172), NPM1, RUNX1, TET2 or WT1 genes, and FLT3-tyrosine kinase domain (FLT3-TKD) mutations], as described previously (17,18). A variant allele frequency of ≥10% was used as the cut point to distinguish between mutated versus wild-type alleles of these genes. The presence of mutations in the CEBPA gene and FLT3-internal tandem duplications (FLT3-ITD) were evaluated using Sanger sequencing (19) and fragment analysis (20), as described previously. For the remaining older CN-AML patients (n=44), mutations in all the aforementioned genes were evaluated with Sanger sequencing or fragment analysis, as described previously (19-28). Since only double CEBPA mutations are favorable prognostic markers in CN-AML (29,30), this genotype was considered as mutated, and grouped patients with single-mutated or wild-type CEBPA together.

AML cell lines and patient AML blasts.

Kasumi-1 cells were purchased from American Type Culture Collection (ATCC, Manassas, Va.). Blasts from AML patients were maintained in SFEM (StemCell Technologies, Vancouver, BC) medium supplemented with 10% FBS, and 1× StemSpan CC100 cytokine cocktail (StemCell Technologies) unless otherwise noted. AML blasts used in the experiments were obtained from apheresis blood samples collected from patients treated at The Ohio State University (OSU) and stored in the OSU Leukemia Tissue Bank. Informed consent to use the tissue for investigational studies was obtained from each patient according to OSU institutional guidelines.

RNA Extraction, RNA Expression Quantification.

RNA, cDNA, and real time PCR were performed using previously published methods (1). All primers/probes were purchased from Applied Biosystems (Foster City, Calif.).

Western blot analysis.

Equal numbers of bulk blast cells from AML patients and normal human BM MNCs (AllCells, Alameda, Calif.), or murine WT BM cells and $Mll^{PTD/WT}Flt3^{ITD/WT}$ leukemic cells were lysed in 100 μl of Pierce RIPA buffer (Cat. #8990, Thermo Scientific, Foster City, Calif.) supplemented with protease and phosphatase inhibitors (Roche, Basel, Switzerland) on ice for 20 min. Protein lysates were separated by polyacrylamide gel electrophoresis (SDS-PAGE) and transferred to polyvinylidene fluoride membranes. Membranes were incubated with antibodies for EGFL7 (LS-C153302 and LS-C40134, LifeSpan BioSciences, Seattle, Wash.), goat anti-EGFL7 (sc-34116), rabbit anti-GAPDH antibodies (Santa Cruz Biotechnology, Santa Cruz, Calif.), pAKT-Ser473 and AKT antibodies (Cell Signaling Technology, Boston, Mass.). Proteins were visualized with HRP-conjugated sheep anti-mouse, goat anti-rat, donkey anti-rabbit, and donkey anti-goat secondary antibodies (GE Healthcare, Little Chalfont, United Kingdom) and detected using ECL Select Western Blotting Detection Reagent (GE Healthcare).

Immunohistochemistry.

Formalin-fixed humeri were washed with distilled water and placed in decalcifying EDTA pH 7.2-7.6 (Cat #s2516, Poly Scientific R&D Corporation, Bay Shore, N.Y.). Samples were placed on a rotating mixer at 37° C. until bones were soft and pliable (approximately 7 days). Decalcifying EDTA was changed every 48 hours until decalcification was complete. Bones were then rinsed with 1×PBS three times for 5 minutes each, distilled water three times for 5 minutes each, 50% ethanol for 5 minutes, 70% ethanol for 5 minutes, and then stored in 70% ethanol. Bones were embedded in paraffin blocks and sectioned on to glass slides. Egfl7 immunohistochemistry was performed with goat polyclonal anti-mouse Egfl7 (R-12) antibody (Cat #sc-34416, Santa Cruz Biotechnology, Santa Cruz, Calif.) at 1:50 dilution using the avidin-biotin complex method. Tissue embedding, sectioning, and immunohistochemistry were performed by The OSU Comparative Pathology and Mouse Phenotyping Core.

Enzyme-linked immunosorbent assay (ELISA).

Serum of AML patients or normal donors (OSU Leukemia Tissue Bank and Discovery Life Sciences) was diluted in PBS in a 1:100 ratio. One-hundred microliters of EGF7 protein standards (provided by the manufacturer) or diluted samples were added to a 96-well pre-coated plate into replicate wells, and the assay was performed according to the manufacturer's protocol (Cloud-Clone Corp, Houston, Tex.). Standard curves were generated from the kit standards and used to extrapolate EGFL7 concentrations in blood plasma/serum.

CFU assay.

For the colony formation assay, blasts of AML patients (20,000 cells) were mixed with Methocult HM4434 (StemCell Technologies) in the absence or presence of 0.25 µM recombinant human EGFL7 and plated on to 2 cm dishes for 10 days. Colonies with more than 50 cells were counted using a light microscope. Each condition was repeated in triplicate, n=3 independent experiments.

Statistical methods.

For laboratory in vitro experiments, 2-tailed student's t tests were performed using GraphPad Prism version 5.0a (Graphpad Software, San Diego, Calif.). P values <0.05 were considered significant.

REFERENCES

1. Short N J, Ravandi F (2016) Acute myeloid leukemia: Past, present, and prospects for the future. *Clin Lymphoma Myeloma Leuk* 16(Suppl):S25-S29.
2. Dorrance A M, et al. (2015) Targeting leukemia stem cells in vivo with antagomiR-126 nanoparticles in acute myeloid leukemia. *Leukemia* 29(11):2143-2153.
3. Nikolic I, Plate K-H, Schmidt M H H (2010) EGFL7 meets miRNA-126: An angiogenesis alliance. *J Angiogenes Res* 2(1):9.
4. de Leeuw D C, et al. (2014) Attenuation of microRNA-126 expression that drives CD34$^+$38$^-$ stem/progenitor cells in acute myeloid leukemia leads to tumor eradication. *Cancer Res* 74(7):2094-2105.
5. Lechman E R, et al. (2016) miR-126 regulates distinct self-renewal outcomes in normal and malignant hematopoietic stem cells. *Cancer Cell* 29(4):602-606.
6. Nichol D, Stuhlmann H (2012) EGFL7: A unique angiogenic signaling factor in vascular development and disease. *Blood* 119(6):1345-1352.
7. Oh J, et al. (2014) High expression of epidermal growth factor-like domain 7 is correlated with poor differentiation and poor prognosis in patients with epithelial ovarian cancer. *J Gynecol Oncol* 25(4):334-341.
8. Bambino K, Lacko L A, Hajjar K A, Stuhlmann H (2014) Epidermal growth factor-like domain 7 is a marker of the endothelial lineage and active angiogenesis. *Genesis* 52(7): 657-670.
9. Fan C, et al. (2013) The expression of Egfl7 in human normal tissues and epithelial tumors. *Int J Blot Markers* 28(1):71-83.
10. Döhner H, et al. (2017) Diagnosis and management of AML in adults: 2017 ELN recommendations from an international expert panel. *Blood* 129(4):424-447.
11. Yan P, et al. (2012) Genome-wide methylation profiling in decitabine-treated patients with acute myeloid leukemia. *Blood* 120(12):2466-2474.
12. Zorko N A, et al. (2012) Mll partial tandem duplication and Flt3 internal tandem duplication in a double knock-in mouse recapitulates features of counterpart human acute myeloid leukemias. *Blood* 120(5):1130-1136.
13. Takeuchi K, et al. (2014) EGF-like-domain-7 is required for VEGF-induced Akt/ERK activation and vascular tube formation in an ex vivo angiogenesis assay. *PLoS One* 9(3):e91849.
14. Nikolić I, et al. (2013) EGFL7 ligates integrin to enhance vessel formation. *Blood* 121(15):3041-3050.
15. Li Z, et al. (2008) Distinct microRNA expression profiles in acute myeloid leukemia with common translocations. *Proc Natl Acad Sci USA* 105(40):15535-15540.
16. Mrozek K, et al. (2008) Central review of cytogenetics is necessary for cooperative group correlative and clinical studies of adult acute leukemia: The Cancer and Leukemia Group B experience. *Int J Oncol* 33(2):239-244.
17. Garzon R, et al. (2014) Expression and prognostic impact of lncRNAs in acute myeloid leukemia. *Proc Natl Acad Sci USA* 111(52):18679-18684.
18. Kroll K W, et al. (2016) MuCor: Mutation aggregation and correlation. *Bioinformatics* 32(10):1557-1558.
19. Marcucci G, et al. (2008) Prognostic significance of, and gene and microRNA expression signatures associated with, CEBPA mutations in cytogenetically normal acute myeloid leukemia with high-risk molecular features: A Cancer and Leukemia Group B study. *J Clin Oncol* 26(30:5078-5087.
20. Whitman S P, et al. (2001) Absence of the wild-type allele predicts poor prognosis in adult de novo acute myeloid leukemia with normal cytogenetics and the internal tandem duplication of FLT3: A Cancer and Leukemia Group B study. *Cancer Res* 61(19):7233-7239.
21. Metzeler K H, et al. (2011) ASXL1 mutations identify a high-risk subgroup of older patients with primary cytogenetically normal AML within the ELN Favorable genetic category. *Blood* 118(26):6920-6929.
22. Marcucci G, et al. (2012) Age-related prognostic impact of different types of DNMT3A mutations in adults with primary cytogenetically normal acute myeloid leukemia. *J Clin Oncol* 30(7):742-750.
23. Marcucci G, et al. (2010) IDH1 and IDH2 gene mutations identify novel molecular subsets within de novo cytogenetically normal acute myeloid leukemia: A Cancer and Leukemia Group B study. *J Clin Oncol* 28(14):2348-2355.
24. Whitman S P, et al. (2008) FLT3 D835/I836 mutations are associated with poor disease-free survival and a distinct gene-expression signature among younger adults with de novo cytogenetically normal acute myeloid leukemia lacking FLT3 internal tandem duplications. *Blood* 111(3):1552-1559.

25. Becker H, et al. (2010) Favorable prognostic impact of NPM1 mutations in older patients with cytogenetically normal de novo acute myeloid leukemia and associated gene- and microRNA-expression signatures: A Cancer and Leukemia Group B study. *J Clin Oncol* 28 (4): 96-604.
26. Mendler J H, et al. (2012) RUNX1 mutations are associated with poor outcome in younger and older patients with cytogenetically normal acute myeloid leukemia and with distinct gene and microRNA expression signatures. *J Clin Oncol* 30(25):3109-3118.
27. Metzeler K H, et al. (2011) TET2 mutations improve the new European LeukemiaNet risk classification of acute myeloid leukemia: A Cancer and Leukemia Group B study. *J Clin Oncol* 29(10): 1373-1381.
28. Paschka P, et al. (2008) Wilms' tumor 1 gene mutations independently predict poor outcome in adults with cytogenetically normal acute myeloid leukemia: A Cancer and Leukemia Group B study. *J Clin Oncol* 26(28):4595-4602.
29. Wouters B J, et al. (2009) Double CEBPA mutations, but not single CEBPA mutations, define a subgroup of acute myeloid leukemia with a distinctive gene expression profile that is uniquely associated with a favorable outcome. *Blood* 113(13):3088-3091.
30. Dufour A, et al. (2010) Acute myeloid leukemia with biallelic CEBPA gene mutations and normal karyotype represents a distinct genetic entity associated with a favorable clinical outcome. *J Clin Oncol* 28(4):570-577.

TABLE 1

Multivariable analyses of outcome according to the EGFL7 risk group in 126 older (aged ≥60 years) patients with de novo cytogenetically normal acute myeloid leukemia

| Variables in Final Models | Disease-free survival HR (95% CI) | P | Overall survival HR (95% CI) | P |
|---|---|---|---|---|
| EGFL7 risk group, favorable vs. unfavorable | 0.57 (0.34-0.95) | 0.03 | 0.45 (0.29-0.71) | <0.001 |
| Extramedullary involvement, present vs. absent | 1.99 (1.13-3.51) | 0.02 | — | — |
| miR-155, high vs. low* | — | — | 2.47 (1.65-3.70) | <0.001 |
| Platelets, continuous | — | — | 1.22 (1.09-1.36) | <0.001 |

HR, hazard ratio; CI, confidence interval; vs., versus.
NOTE:
Hazard ratios greater than (or less than) 1.0 indicate higher (or lower) risk for relapse or death (disease-free survival) or for death (overall survival) for the higher value of the continuous variables and the first category listed for the categorical variables.
*The median expression value was used as the cut point.

TABLE 2

Comparison of clinical and molecular characteristics by EGFL7-expresser status of younger (aged <60 years) adult patients with de novo cytogenetically normal acute myeloid leukemia

| Characteristic | Low EGFL7* (n = 187) | High EGFL7* (n = 187) | P |
|---|---|---|---|
| Age (years) | | | 0.09 |
| Median | 47 | 44 | |
| Range | 19-59 | 17-59 | |
| Sex, n (%) | | | 0.12 |
| Male | 88 (47) | 104 (56) | |
| Female | 99 (53) | 83 (44) | |
| Race, n (%) | | | 0.21 |
| White | 170 (93) | 163 (89) | |
| Non-white | 13 (7) | 21 (11) | |
| Hemoglobin (g/dL) | | | 0.89 |
| Median | 9.3 | 9.2 | |
| Range | 4.6-25.1 | 4.2-14.4 | |
| Platelet count (×10$^9$/L) | | | 0.002 |
| Median | 67 | 50 | |
| Range | 8-433 | 8-445 | |
| WBC count (×10$^9$/L) | | | 0.001 |
| Median | 35.6 | 24.3 | |
| Range | 0.6-308.8 | 0.8-475.0 | |
| Blood blasts, % | | | <0.001 |
| Median | 53 | 66 | |
| Range | 0-97 | 0-97 | |
| Bone marrow blasts, % | | | 0.35 |
| Median | 69 | 65 | |
| Range | 10-96 | 19-95 | |
| Extramedullary involvement, n (%) | | | 0.02 |
| Present | 65 (35) | 43 (24) | |
| Absent | 119 (65) | 139 (76) | |
| ASXL1, n (%) | | | 0.78 |
| Mutated | 6 (3) | 7 (4) | |
| Wild-type | 174 (97) | 167 (96) | |
| CEBPA, n (%) | | | <0.001 |
| Double Mutated | 5 (3) | 50 (28) | |
| Wild-type | 173 (97) | 129 (72) | |
| DNMT3A, n (%) | | | 0.004 |
| Mutated | 85 (47) | 56 (31) | |
| R882 Mutated | 61 | 45 | |
| Non-R882 Mutated | 24 | 11 | |
| Wild-type | 97 (53) | 122 (69) | |
| FLT3-ITD, n (%) | | | 0.20 |
| Present | 66 (36) | 78 (43) | |
| Absent | 118 (64) | 105 (57) | |
| FLT3-TKD, n (%) | | | 0.03 |
| Present | 26 (14) | 12 (7) | |
| Absent | 155 (86) | 165 (93) | |
| IDH1, n (%) | | | 0.85 |
| Mutated | 14 (8) | 15 (8) | |
| Wild-type | 168 (92) | 163 (92) | |
| IDH2, n (%) | | | 0.01 |
| Mutated | 25 (14) | 10 (6) | |
| Wild-type | 157 (86) | 168 (94) | |
| NPM1, n (%) | | | <0.001 |
| Mutated | 130 (74) | 76 (43) | |
| Wild-type | 45 (26) | 99 (57) | |
| RUNX1, n (%) | | | 0.17 |
| Mutated | 7 (4) | 13 (7) | |
| Wild-type | 175 (96) | 165 (93) | |
| TET2, n (%) | | | 0.86 |
| Mutated | 20 (11) | 18 (10) | |
| Wild-type | 162 (89) | 160 (90) | |
| WT1, n (%) | | | 0.02 |
| Mutated | 13 (7) | 27 (15) | |
| Wild-type | 169 (93) | 151 (85) | |
| ELN Genetic Group*, n (%) | | | 0.04 |
| Favorable | 110 (62) | 90 (52) | |
| Intermediate | 48 (27) | 47 (27) | |
| Adverse | 19 (11) | 35 (20) | |
| BAALC, n (%)[†] | | | <0.001 |
| High | 38 (24) | 135 (73) | |
| Low | 122 (76) | 49 (27) | |
| ERG, n (%)[†] | | | <0.001 |
| High | 47 (25) | 139 (74) | |
| Low | 138 (75) | 48 (26) | |
| MN1, n (%)[†] | | | <0.001 |
| High | 53 (30) | 127 (69) | |
| Low | 121 (70) | 58 (31) | |
| miR-181a, n (%)[†] | | | <0.001 |
| High | 53 (38) | 97 (61) | |
| Low | 87 (62) | 62 (39) | |
| miR-3151, n (%) | | | <0.001 |
| Expressed | 5 (4) | 46 (29) | |
| Not expressed | 135 (96) | 113 (71) | |

TABLE 2-continued

Comparison of clinical and molecular characteristics by EGFL7-expresser status of younger (aged <60 years) adult patients with de novo cytogenetically normal acute myeloid leukemia

| Characteristic | Low EGFL7* (n = 187) | High EGFL7* (n = 187) | P |
|---|---|---|---|
| miR-155, n (%)† | | | 0.008 |
| High | 59 (42) | 92 (58) | |
| Low | 81 (58) | 67 (42) | | n, number; WBC, white blood cell; FLT3-ITD, internal tandem duplication of the FLT3 gene; FLT3-TKD, tyrosine kinase domain mutation in the FLT3 gene, ELN; European LeukemiaNet.
*Within patients with cytogenetically normal acute myeloid leukemia (CN-AML), the ELN Favorable Risk Category comprises patients with double-mutated CEBPA and patients with mutated NPM1 without FLT3-ITD or with FLT3-ITD$^{low}$. The ELN Intermediate Risk Category includes patients with either wild-type NPM1 without FLT3-ITD, wild-type NPM1 and FLT3-ITD$^{low}$ or mutated NPM1 and FLT3-ITD$^{high}$. The ELN Adverse Risk Category comprises patients with NPM1 with FLT3-ITD$^{high}$, and/or mutated RUNX1 (if it does not co-occur with a Favorable AML subtype) and/or mutated ASXL1 (if it does not co-occur with a Favorable AML subtype) and/or mutated TP53. FLT3-ITD$^{low}$ is defined by a FLT3-ITD/FLT3 wild-type allelic ratio of less than 0.5 and FLT3-ITD$^{high}$ is defined as by a FLT3-ITD/FLT3 wild-type allelic ratio of equal to or more than 0.5.
†The median expression value was used as the cut point.

TABLE 3

Treatment outcomes according to EGFL7 expression in 374 younger (aged <60 years) adult patients with de novo cytogenetically normal acute myeloid leukemia

| End point | Low EGFL7* (n = 187) | High EGFL7* (n = 187) | P† |
|---|---|---|---|
| Complete response, n (%) | 165 (88) | 146 (78) | 0.01 |
| Disease-free survival | | | 0.09 |
| Median, years | 1.9 | 1.5 | |
| % disease-free at 5 years (95% CI) | 41 (34-49) | 31 (24-39) | |
| Overall survival‡ | | | 0.002 |
| Median, years | 4.5 | 2.1 | |
| % alive at 5 years (95% CI) | 49 (41-56) | 34 (27-41) | |
| Event-free survival§ | | | 0.005 |
| Median, years | 1.5 | 0.8 | |
| % event-free at 5 years (95% CI) | 37 (30-43) | 25 (19-31) | | n, number; CI, confidence interval.
*Median cut was used to dichotomize the variable.
†P-values for categorical variables are from Fisher's exact test, P-values for the time to event variables are from the log-rank test.
‡The median follow-up for those alive is 8.2 years, range: 0.6-18.1 years (n = 143).
§The median follow-up for those who have not had an event is 7.6 years, range: 0.6-18.1 years (n = 106).

TABLE 4

Comparison of clinical and molecular characteristics by EGFL7-expresser status of older (aged ≥60 years) patients with de novo cytogenetically normal acute myeloid leukemia

| Characteristic | Low EGFL7* (n = 99) | High EGFL7* (n = 99) | P |
|---|---|---|---|
| Age (years) | | | 0.21 |
| Median | 68 | 70 | |
| Range | 60-83 | 60-81 | |
| Sex, n (%) | | | 0.09 |
| Male | 45 (45) | 58 (59) | |
| Female | 54 (55) | 41 (41) | |
| Race, n (%) | | | 0.81 |
| White | 89 (90) | 90 (92) | |
| Non-white | 10 (10) | 8 (8) | |
| Hemoglobin (g/dL) | | | 0.70 |
| Median | 9.4 | 9.4 | |
| Range | 5.4-15.0 | 6.0-13.1 | |
| Platelet count (×10$^9$/L) | | | 0.26 |
| Median | 79 | 60 | |
| Range | 4-271 | 11-850 | |
| WBC count (×10$^9$/L) | | | 0.14 |
| Median | 28.4 | 21.1 | |
| Range | 1.0-450.0 | 1.0-434.1 | |
| Blood blasts, % | | | 0.22 |
| Median | 37 | 57 | |
| Range | 0-97 | 0-99 | |
| Bone marrow blasts, % | | | 0.85 |
| Median | 68 | 66 | |
| Range | 4-97 | 17-96 | |
| Extramedullary involvement, n (%) | | | 0.87 |
| Present | 24 (25) | 22 (23) | |
| Absent | 73 (75) | 74 (77) | |
| ASXL1, n (%) | | | 0.68 |
| Mutated | 12 (12) | 15 (15) | |
| Wild-type | 86 (88) | 84 (85) | |
| CEBPA, n (%) | | | 0.01 |
| Double Mutated | 0 (0) | 7 (7) | |
| Wild-type | 99 (100) | 92 (93) | |
| DNMT3A, n (%) | | | 0.45 |
| Mutated | 28 (29) | 34 (34) | |
| R882 Mutated | 17 | 19 | |
| Non-R882 Mutated | 11 | 15 | |
| Wild-type | 68 (71) | 65 (66) | |
| FLT3-ITD, n (%) | | | <0.001 |
| Present | 20 (20) | 43 (43) | |
| Absent | 79 (80) | 56 (57) | |
| FLT3-TKD, n (%) | | | 0.67 |
| Present | 11 (11) | 14 (14) | |
| Absent | 87 (89) | 85 (86) | |
| IDH1, n (%) | | | 0.29 |
| Mutated | 16 (16) | 10 (10) | |
| Wild-type | 83 (84) | 89 (90) | |
| IDH2, n (%) | | | 1.00 |
| Mutated | 22 (22) | 21 (21) | |
| Wild-type | 77 (78) | 78 (79) | |
| NPM1, n (%) | | | <0.001 |
| Mutated | 72 (73) | 43 (43) | |
| Wild-type | 27 (27) | 56 (57) | |
| RUNX1, n (%) | | | <0.001 |
| Mutated | 7 (7) | 26 (26) | |
| Wild-type | 89 (93) | 73 (74) | |
| TET2, n (%) | | | 0.001 |
| Mutated | 35 (36) | 15 (15) | |
| Wild-type | 63 (64) | 84 (85) | |
| WT1, n (%) | | | 1.00 |
| Mutated | 4 (4) | 4 (4) | |
| Wild-type | 95 (96) | 95 (96) | |
| ELN Genetic Group*, n (%) | | | <0.001 |
| Favorable | 64 (65) | 28 (28) | |
| Intermediate | 20 (20) | 37 (37) | |
| Adverse | 14 (14) | 34 (34) | |
| BAALC†, n (%) | | | <0.001 |
| High | 29 (29) | 69 (70) | |
| Low | 70 (71) | 30 (30) | |
| ERG†, n (%) | | | <0.001 |
| High | 25 (25) | 74 (75) | |
| Low | 74 (75) | 25 (25) | |
| MN1†, n (%) | | | <0.001 |
| High | 24 (37) | 48 (70) | |
| Low | 41 (63) | 21 (30) | |
| miR-181a†, n (%) | | | 0.02 |
| High | 35 (42) | 53 (60) | |
| Low | 48 (58) | 35 (40) | |

TABLE 4-continued

Comparison of clinical and molecular characteristics by EGFL7-expresser status of older (aged ≥60 years) patients with de novo cytogenetically normal acute myeloid leukemia

| Characteristic | Low EGFL7* (n = 99) | High EGFL7* (n = 99) | P |
|---|---|---|---|
| miR-3151*, n (%) | | | 0.15 |
| High | 31 (40) | 40 (53) | |
| Low | 46 (60) | 36 (47) | |
| miR-155†, n (%) | | | 0.05 |
| High | 34 (40) | 49 (55) | |
| Low | 52 (60) | 40 (45) | | n, number; WBC, white blood cell; FLT3-ITD, internal tandem duplication of the FLT3 gene; FLT3-TKD, tyrosine kinase domain mutation in the FLT3 gene, ELN; European LeukemiaNet.
*In patients with cytogenetically normal acute myeloid leukemia (CN-AML), the ELN Favorable Risk Category comprises patients with double-mutated CEBPA and patients with mutated NPM1 without FLT3-ITD or with FLT3-ITD$^{low}$. The ELN Intermediate Risk Category includes patients with either wild-type NPM1 without FLT3-ITD, wild-type NPM1 and FLT3-ITD$^{low}$ or mutated NPM1 and FLT3-ITD$^{high}$. The ELN Adverse Risk Category comprises patients with wild-type NPM1 with FLT3-ITD$^{high}$, and/or mutated RUNX1 (if it does not co-occur with a Favorable AML subtype) and/or mutated ASXL1 (if it does not co-occur with a Favorable AML subtype) and/or mutated TP53. FLT3-ITD$^{low}$ is defined by a FLT3-ITD/FLT3 wild-type allelic ratio of less than 0.5 and FLT3-ITD$^{high}$ is defined as by a FLT3-ITD/FLT3 wild-type allelic ratio of equal to or more than 0.5.
†The median expression value was used as the cut point.

TABLE 5

Treatment outcomes according to EGFL7 expression in 198 older (aged ≥60 years) patients with de novo cytogenetically normal acute myeloid leukemia

| End point | Low EGFL7 (n = 99) | High EGFL7 (n = 99) | P† |
|---|---|---|---|
| Complete response, n (%) | 75 (76) | 57 (58) | 0.01 |
| Disease-free survival | | | 0.09 |
| Median, years | 1.0 | 0.6 | |
| % disease-free at 5 years (95% CI) | 13 (7-22) | 11 (4-20) | |
| Overall survival‡ | | | 0.003 |
| Median, years | 1.4 | 0.8 | |
| % alive at 5 years (95% CI) | 19 (12-27) | 9 (4-15) | |
| Event-free survival§ | | | 0.005 |
| Median, years | 0.8 | 0.4 | |
| % event-free at 5 years (95% CI) | 10 (5-17) | 6 (2-12) | | n, number; CI, confidence interval.
*From Affymetrix microarray platform HG-U133 Plus 2.0. Median cut was used to dichotomize the variable.
†P-values for categorical variables are from Fisher's exact test, P-values for time to event variables are from the log-rank test.
‡The median follow-up for those alive is 9.2 years, range: 2.3-13.9 years (n = 15).
§The median follow-up for those who have not had an event is 9.2 years, range: 7.3-13.9 years (n = 10).

TABLE 6

Treatment outcomes according to EGFL7 risk group in 126 older (aged ≥60 years) patients with de novo cytogenetically normal acute myeloid leukemia

| End point | Unfavorable EGFL7 risk group* (n = 90) | Favorable EGFL7 risk group* (n = 36) | P† |
|---|---|---|---|
| Complete response, n (%) | 53 (59) | 28 (78) | 0.06 |
| Disease-free survival | | | 0.05 |
| Median, years | 0.7 | 1.1 | |
| % disease-free at 5 years (95% CI) | 9 (3-19) | 25 (11-42) | |
| Overall survival‡ | | | 0.004 |
| Median, years | 0.9 | 1.6 | |
| % alive at 5 years (95% CI) | 8 (4-15) | 25 (12-40) | |
| Event-free survival§ | | | 0.008 |
| Median, years | 0.4 | 1.1 | |
| % event-free at 5 years (95% CI) | 6 (2-12) | 19 (9-34) | | n, number; CI, confidence interval.
*Favorable risk group consists of patients with low EGFL7 AFFY expression and high EGFL7 methylation; Unfavorable risk group consists of patients with high EGFL7 AFFY expression and/or low EGFL7 methylation.
AFFY data is from the Affymetrix microarray platform HG-U133 Plus 2.0.
†P-values for categorical variables are from Fisher's exact test, P-values for time to event variables are from the log-rank test.
‡The median follow-up for those alive is 9.2 years, range: 2.3-13.9 years (n = 15).
§The median follow-up for those who have not had an event is 9.2 years, range: 7.3-13.9 years (n = 10)

TABLE 7

Multivariable analyses of event-free survival in older (aged ≥ 60 years) patients with de novo cytogenetically normal acute myeloid leukemia

| Variables considered | Event-free survival | | | | | |
|---|---|---|---|---|---|---|
| | HR (95% CI) | P | HR (95% CI) | P | HR (95% CI) | P |
| EGFL7 risk group, favorable vs. unfavorable | 0.48 (0.31-0.77) | 0.002 | 0.44 (0.28-0.70) | <0.001 | 0.46 (0.29, 0.72) | <.001 |
| White Blood Cell count, continuous | 1.22 (1.05-1.40) | 0.007 | 1.20 (1.04-1.39) | 0.01 | 1.17 (1.01, 1.36) | 0.04 |
| miR-155, high vs. low* | 1.68 (1.14-2.47) | 0.008 | — | — | — | — |
| Platelets, continuous | — | — | 1.16 (1.04-1.28) | 0.006 | — | — |
| Extramedullary Involvement, present vs. absent | — | — | — | — | 1.63 (1.05, 2.53) | 0.03 |

HR, hazard ratio;
CI, confidence interval;
vs., versus.
NOTE:
Hazard ratios greater than (or less than) 1.0 indicate higher (or lower) for failure to achieve complete remission, relapse or death (event-free survival) for the higher value of the continuous variables and the first category listed for the categorical variables.
*The median expression value was used as the cut point.

Example 2. Methods and Treatment Protocols

Treatment protocols.

All patients included in our study were treated on Cancer and Leukemia Group B (CALGB)/Alliance for Clinical Trials in Oncology (Alliance) first-line protocols for patients with acute myeloid leukemia (AML), and received cytarabine/daunorubicin-based induction therapy (1). Per protocol, all patients were to receive at least one induction cycle. For patients with residual leukemia present in a bone marrow (BM) biopsy after one induction cycle, a second cycle of induction was administered. None of the protocols included allogeneic stem cell transplantation (SCT) in first complete remission (CR). Patients enrolled on the treatment protocols also provided written informed consent to participate in the companion protocols CALGB 20202 (molecular studies in AML), CALGB 8461 (prospective cytogenetic companion), and CALGB 9665 (leukemia tissue bank), which involved collection of pretreatment BM aspirates and blood samples.

Younger (<60 years) adult patients were enrolled on the following treatment protocols: CALGB 19808, CALGB 10503, CALGB 9621, CALGB 10603, CALGB 9222, CALGB 8525, CALGB 9022, CALGB 8721, CALGB 8821 and CALGB 9120. Patients enrolled on to CALGB 19808 (n=113) were randomly assigned to receive induction chemotherapy with cytarabine/daunorubicin, and etoposide with or without PSC-833 (valspodar), a multidrug resistance protein inhibitor (1). Upon attainment of CR, patients were assigned to intensification with high-dose cytarabine and etoposide for stem-cell mobilization followed by myeloablative treatment with busulfan and etoposide supported by autologous peripheral blood SCT. Patients included in CALGB 10503 (n=112) received cytarabine/daunorubicin-based induction chemotherapy and those who achieved CR further received a two-step consolidation with chemo-mobilization and autologous SCT if eligible, or high-dose cytarabine-based consolidation if not. Maintenance with decitabine began as soon as possible after recovery from consolidation (2). Patients enrolled on to CALGB 9621 (n=60) were treated similarly to those on CALGB 19808, as previously reported (3). Patients in CALGB 10603 (n=40) were stratified by FLT3 mutation subtype [FLT3-TKD vs. FLT3-ITD-high allelic ratio (>0.70) vs. low allelic ratio (0.05-0.70)], and were randomized to receive cytarabine/daunorubicin-based induction chemotherapy and high-dose cytarabine consolidation in combination with either the multi-kinase inhibitor midostaurin or placebo. One-year midostaurin or placebo maintenance was administered after the last cycle of consolidation therapy (4). Patients enrolled in CALGB 9222 (n=27) received cytarabine/daunorubicin-based induction chemotherapy, and those who achieved CR received either three cycles of high-dose cytarabine or three cycles of a so-called non cross-resistant regimen (the first cycle of this regimen was high-dose cytarabine, the second was cyclophosphamide plus etoposide, and the third was mitoxantrone plus diaziquone) (5). Patients enrolled on to CALGB 8525 (n=17) who achieved CR after cytarabine/daunorubicin-based induction chemotherapy were randomly assigned to consolidation with different doses of cytarabine followed by maintenance treatment (6). Patients who participated in CALGB 9022 (n=2) and achieved CR after cytarabine/daunorubicin-based induction chemotherapy received one course of high-dose cytarabine consolidation, followed by one course of cyclophosphamide and etoposide, followed by one course of mitoxantrone and diaziquone (7).

Older patients (≥60 years) were enrolled on CALGB/Alliance protocols 9720, 10201, 8525, 8923 or 9420. Patients on CALGB 9720 (n=95) (8) and 9420 (n=5) (9) received induction chemotherapy consisting of cytarabine in combination with daunorubicin and etoposide, with (CALGB 9420) or with/without (CALGB 9720) the multidrug resistance protein modulator PSC-833. The PSC-833 arm of CALGB 9720 was closed after random assignment of 120 patients because of excessive early deaths, and enrollment continued on the chemotherapy-only control arm. Patients on CALGB 9720 after a single consolidation dose, were randomly assigned to low-dose recombinant interleukin-2 maintenance therapy or none (10). Interleukin-2 maintenance was not associated with differences in patient outcome. Patients on CALGB 10201 (n=65) received induction chemotherapy consisting of cytarabine and daunorubicin, with or without the BCL2 antisense oblimersen sodium. Preliminary results showed no impact of the antisense therapy on outcome (11). Patients on CALGB 8525 (n=18) were treated with induction chemotherapy consisting of cytarabine in combination with daunorubicin and were randomly assigned to consolidation with different doses of cytarabine followed by maintenance treatment (12). Patients on CALGB 8923 (n=15) received induction chemotherapy consisting of cytarabine and daunorubicin and were randomly assigned to receive post-remission therapy with cytarabine alone or in combination with mitoxantrone (13).

Transcriptome analysis.

In the cohort of younger adults with CN-AML (n=374) transcriptome analysis was performed with total RNA sequencing. In brief, extracted total RNA was assessed for quality on an Agilent 2100 Bioanalyzer (BioA) using the RNA 6000 Nanochip and for quantity on a Qubit 2.0 Fluorometer (Agilent Technologies, Santa Clara, Calif.) using the RNA HS Assay Kit. Samples with a RNA Integrity Number (RIN) greater than four, with no visible sign of genomic DNA (gDNA) contamination and a concentration of >40 ng/µL were used for total RNA library generation. RNA-seq libraries were prepared using the Illumina TruSeq Stranded Total RNA Sample Prep Kit with RiboZero Gold (#RS1222201) according to the manufacturer's instructions. Sequencing was performed with the Illumina HiSeq 2500 system using the HiSeq version 3 sequencing reagents to an approximate cluster density of 800,000/mm$^2$. Image analysis, base calling, error estimation, and quality thresholds were performed using the HiSeq Controller Software (version 2.2.38) and the Real Time Analyzer (RTA) software (version 1.18.64).

For microRNA (miR) profiling a subset of patients with RNA samples of sufficient quality (n=300) was analyzed with small RNA sequencing (smRNA-seq). SmRNA-seq libraries were generated using the NEBNext Multiplex Small RNA Library Prep Set (Cat #: E7300L; New England Biolabs, Inc., Ipswich, Mass.). Library generation steps were performed as described by the manufacturer. The input RNA criteria for smRNA-seq were: a Qubit RNA concentration of >50 ng/µL and a BioA RNA RIN value >7. Generation of barcodes and enrichment of fragments with 3- and 5-adaptors for smRNA libraries were accomplished by 12 cycles of PCR amplification. Prior to pooling smRNA-seq libraries for enriching smRNA species, libraries generated from each sample were assessed for relative amount of smRNA fragments migrating between 140 to 160 bp using the Agilent Bioanalyzer HS DNA assay. Size selection/enrichment for smRNAs was accomplished using the Sage Science Pippin Prep (Beverly, Mass.) with 3% pre-cast agarose gel. The profile of the resultant size-selected libraries was ascertained using the Agilent Bioanalyzer HS DNA assay. Each pool of the smRNA-seq libraries was sequenced with other samples with compatible barcodes on an Illumina HiSeq 2500 V3 single-read 50 bp lane to achieve 5-8 million passed filter reads/sample.

Cutadapt and FastQC were used to apply quality control and adapter trimming to FastQC files. The Spliced Transcripts Alignment to a Reference (STAR) software (14) was used to align the short reads to the human genome (GENECODE ver22) (15) and the HTSeq script (16) to quantify and annotate long non-coding RNAs (lncRNAs). Raw data were transformed into reads per million (RPM) prior to statistical analysis. To minimize noise, mRNAs were evaluated in each sample only when at least nine reads were present in a total of 40 million reads.

In the cohort of older CN-AML patients (n=198) RNA samples studied were analyzed for genome-wide gene expression using Affymetrix U133 plus 2.0 GeneChips (Affymetrix, Santa Clara, Calif.). Double-stranded cDNA was prepared (Invitrogen, Carlsbad, Calif.) from total RNA using T7-Oligo(dT) primer (Affymetrix). In vitro transcription was performed with the BioArray HighYield RNA Transcript Labeling Kit (T7) (Enzo Life Science, Farmingdale, N.Y.). Fragmented, biotinylated RNA samples were hybridized to the U133 plus 2.0 GeneChip for 16 hours at 45° C.

For the gene expression analysis, summary measures of the expression levels were computed for each probe set using the robust multichip average method, which incorporates quantile normalization of arrays. Expression values were logged (base 2) before analysis. A filtering step was performed to remove probe sets that did not display significant variation in expression across arrays. In this procedure, a $\chi^2$ test was used to test whether the observed variance in expression of a probe set was significantly larger than the median observed variance in expression for all probe sets using $\alpha=0.01$ as the significance level.

MiR-profiling in the cohort of older CN-AML patients was performed with the OSU-CCC custom microarrays and analyzed as previously reported (17).

Definition of clinical endpoints.

Clinical endpoints were defined according to generally accepted criteria (18). CR required a BM aspirate with cellularity >20% with maturation of all cell lines, ≤5% blasts and undetectable Auer rods; in peripheral blood, an absolute neutrophil count of $\geq 1.5\times10^9$/L, platelet count of $>100\times10^9$/L, and leukemic blasts absent; and no evidence of extramedullary leukemia, all of which had to persist for ≥4 weeks. Relapse was defined by the presence of ≥5% BM blasts, or circulating leukemic blasts, or the development of extramedullary leukemia. Disease-free survival (DFS) was measured from the date of CR until the date of relapse or death (from any cause); patients alive and in continuous first CR were censored at last follow-up. Overall survival (OS) was measured from the date of study entry until the date of death (from any cause); patients alive at last follow-up were censored. Event-free survival (EFS) was measured from the date of study entry until the date of failure to achieve CR, relapse or death. Patients alive and in CR at last follow-up were censored.

Statistical analyses for survival end-points.

Baseline demographic, clinical, and molecular features were compared between patients with low and high EFGL7 expression using the Wilcoxon rank sum and Fisher's exact tests for continuous and categorical variables, respectively (19). The estimated probabilities of DFS, OS and EFS were calculated using the Kaplan-Meier method, and the log-rank test evaluated differences between survival distributions (20). Cox proportional hazard models were used to calculate hazard ratios (HR) for DFS, OS and EFS (21). For the time-to-event endpoints, the proportional hazards assumption was checked for each variable individually. All statistical analyses were performed by the Alliance Statistics and Data Center on a database locked on Apr. 4, 2016 using SAS 9.4 and TIBCO Spotfire S+8.2.

Multivariable proportional hazards models were constructed for DFS and OS using a limited forward elimination procedure. Because of relatively small number of patients in the EGFL7 favorable risk group, a final model could not be constructed for EFS. However, three separate three-variable models could be generated. Variables considered for model inclusion were: lncRNA score status (favorable vs. unfavorable), age (as a continuous variable, in 10-year increments), sex (male vs. female), race (white vs. non-white), white blood cell count (as a continuous variable, in 50-unit increments), hemoglobin (as a continuous variable, in 1-unit increments), platelet count (as a continuous variable, in 50-unit increments), extramedullary involvement (present vs. absent), ASXL1 mutations (mutated vs. wild-type), CEBPA mutations (double-mutated vs. single-mutated or wild-type), DNMT3A mutations (mutated vs. wild-type), FLT3-ITD (present vs. absent), FLT3-TKD (present vs. absent), IDH1 mutations (mutated vs. wild-type), IDH2 mutations (mutated vs. wild-type), NPM1 mutations (mutated vs. wild-type), TET2 mutations (mutated vs. wild-type), RUNX1 mutations (mutated vs. wild-type), WT1 mutations (mutated vs. wild-type), ERG expression levels (high vs. low), BAALC expression levels (high vs. low), MN1 expression levels (high vs. low), miR-181a expression levels (high vs. low), miR-3151 (expressed vs. not expressed), and miR-155 expression levels (high vs. low). For ERG, BAALC, M N1, miR-181a and miR-155, the median expression value was used as the cut point to divide patients into high and low expressers. Variables significant at $\alpha=0.20$ from the univariable analyses were considered for multivariable analyses. For the time-to-event endpoints, the proportional hazards assumption was checked for each variable individually.

REFERENCES

1. Kolitz J E, et al. (2010) P-glycoprotein inhibition using valspodar (PSC-833) does not improve outcomes for patients younger than age 60 years with newly diagnosed acute myeloid leukemia: Cancer and Leukemia Group B study 19808. *Blood* 116(9): 1413-1421.
2. Blum W, et al. (2017) Maintenance therapy with decitabine in younger adults with acute myeloid leukemia in first remission: A phase 2 Cancer and Leukemia Group B study (CALGB 10503). *Leukemia* 31(1):34-39.
3. Kolitz J E, et al. (2004) Dose escalation studies of cytarabine, daunorubicin, and etoposide with and without multidrug resistance modulation with PSC-833 in untreated adults with acute myeloid leukemia younger than 60 years: Final induction results of Cancer and Leukemia Group B study 9621. *J Clin Oncol* 22(21): 4290-4301.
4. Stone R, et al. (2015) The multi-kinase inhibitor midostaurin (M) prolongs survival compared with placebo (P) in combination with daunorubicin (D)/cytarabine (C) induction (ind), high-dose C consolidation (consol), and as maintenance (maint) therapy in newly diagnosed acute myeloid leukemia (AML) patients (pts) age 18-60 with FLT3 mutations (muts): An international prospective randomized (rand) P-controlled double-blind trial (CALGB 10603/RATIFY [Alliance]). *Blood* 126(23) (abstract 6).
5. Moore J O, et al. (2005) Sequential multiagent chemotherapy is not superior to high-dose cytarabine alone as postremission intensification therapy for acute myeloid leukemia in adults under 60 years of age: Cancer and Leukemia Group B study 9222. *Blood* 105(9):3420-3427.
6. Mayer R J, et al. (1994) Intensive postremission chemotherapy in adults with acute myeloid leukemia. *N Engl J Med* 331(14): 896-903.
7. Moore J O, et al. (1997) Granulocyte-colony stimulating factor (filgrastim) accelerates granulocyte recovery after intensive postremission chemotherapy for acute myeloid leukemia with aziridinyl benzoquinone and mitoxantrone: Cancer and Leukemia Group B study 9022. *Blood* 89(3): 780-788.
8. Baer M R, et al. (2002) Phase 3 study of the multidrug resistance modulator PSC-833 in previously untreated patients 60 years of age and older with acute myeloid leukemia: Cancer and Leukemia Group B study 9720. *Blood* 100(4): 1224-1232.
9. Lee E J, et al. (1999) Parallel phase I studies of daunorubicin given with cytarabine and etoposide with or without the multidrug resistance modulator PSC-833 in previously untreated patients 60 years of age or older with acute myeloid leukemia: Results of Cancer and Leukemia Group B study 9420. *J Clin Oncol* 17(9):2831-2839.
10. Baer M R, et al. (2008) Low-dose Interleukin-2 immunotherapy does not improve outcome of patients age 60 years and older with acute myeloid leukemia in first complete remission: Cancer and Leukemia Group B study 9720. *J Clin Oncol* 26(30):4934-4939.
11. Marcucci G, et al. (2007) A phase III randomized trial of intensive induction and consolidation chemotherapy±oblimersen, a pro-apoptotic Bcl-2 antisense oligonucleotide in untreated acute myeloid leukemia patients >60 years old. *J Clin Oncol* 25 (abstract 7012).
13. Stone R, et al. (2001) Postremission therapy in older patients with de novo acute myeloid leukemia: A randomized trial comparing mitoxantrone and intermediate-dose cytarabine with standard-dose cytarabine. *Blood* 98(3): 548-553.
14. Dobin A, et al. (2012) STAR: ultrafast universal RNA-seq aligner. *Bioinformatics* 29(1):15-21.
15. Harrow J, et al: (2012) GENCODE: the reference human genome annotation for The ENCODE Project. *Genome Res* 22(9):1760-1774.
16. Anders S, et al. (2015) HTSeq-a Python framework to work with high-throughput sequencing data. *Bioinformatics* 31(2): 166-169.
17. Marcucci G, et al. (2008) MicroRNA expression in cytogenetically normal acute myeloid leukemia. *N Engl J Med* 358 (18): 1919-1928.
18. Cheson B D, et al. (1990) Report of the National Cancer Institute-sponsored workshop on definitions of diagnosis and response in acute myeloid leukemia. *J Clin Oncol* 8(5): 813-819.
19. Vittinghoff E, et al (2005) Basic statistical methods. *Regression Methods in Biostatistics: Linear, Logistic, Survival and Repeated Measures Models* (Springer, New York), pp 26-67.
20. Kaplan E L, Meier P (1958) Nonparametric estimation from incomplete observations. *J Am Stat Assoc* 282(53): 457-481
21. Vittinghoff E, et al (2005) Logistic regression. *Regression Methods in Biostatistics: Linear, Logistic, Survival and Repeated Measures Models* (Springer, New York), pp 139-202.

Example 3. Expansion of Human Hematopoietic Stem and Progenitor (HSPC) Cells Using Epidermal Growth Factor Like 7 (EGFL7) Protein In this example, it was found that EGFL7 alone was able to expand human and mouse HSPCs in vitro. Specifically, EGFL7 expanded human Cord. Blood CD34+ cells and mouse ckit+ cells (the source of cells in the bone marrow (BM) for HSPCs). These cells expanded without the loss of stem cell potential. This is unique because no one has found this to have an effect on blood cells. Furthermore, the expansion of HSPCs in vitro after periods of time in culture, often causes loss of stem cell potential. However, expansion with EGFL7 was not accompanied by a loss of stem cell potential. This can provide an invaluable tool in order to expand cord blood CD34+ in vitro and allow for the use of this source for patients suffering from hematologic disorders where stem cell transplantation is required and no good bone marrow (BM) donors have been found.

EGFL7 is the host gene to miR-126. EGFL7 is a roughly ~30 KDa secreted protein. The EGEL7 promoter contains 2 ETS and a GATA-2 binding domain. The protein also possesses an EGF/DSL domain which binds to NOTCH, and an EGF/Ca2+ domain which binds calcium. In addition, the protein contains an EMI domain, which is common to many extracellular matrix proteins.

Figure 11:
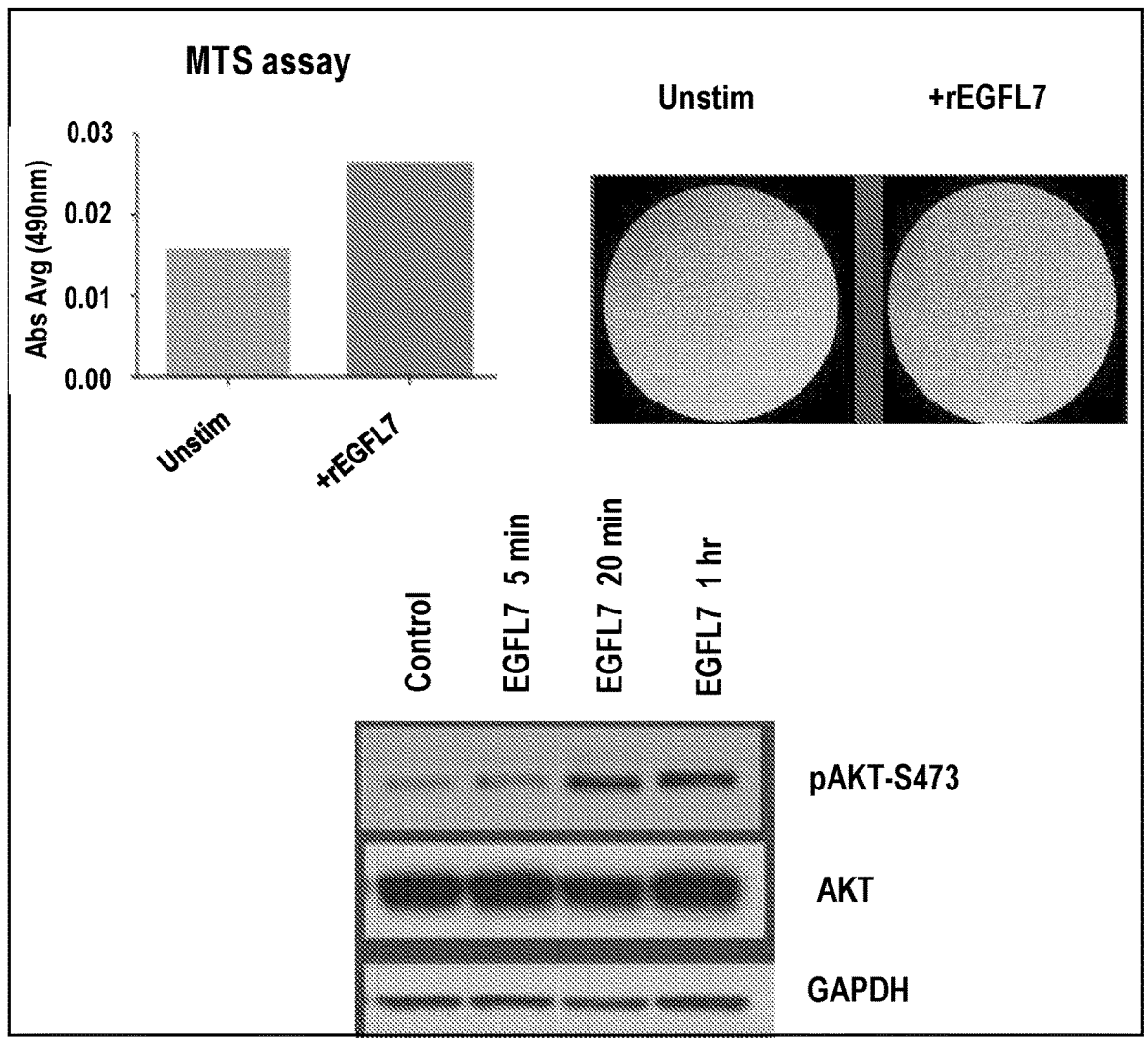
FIG. 11. Recombinant EGFL7 stimulation leads to expansion of human hematopoietic stem and progenitor cells (HSPCs) and AKT phosphorylation. Top Left: $0.3 \times 10^6$ CD34+ cord blood (CB) cells were treated with 0.25 µM recombinant human EGFL7 protein in SFEM 2% BSA for 24 h, cell proliferation was assessed by MTS assay. Top Right: Representative images showing the expansion of cells. Lower: $1 \times 10^6$ CD34+CB cells were treated with 0.25 µM recombinant human EGFL7 in SFEM 2% BSA for 5 min, 20, and 1 h. Total protein was extracted for immunoblotting of phosphor-AKT, total AKT and GAPDH (lower panel).

In this example, since little is known about the expression and function of EGFL7 in normal hematopoiesis, the role of EGFL7 was examined in normal hematopoiesis. As shown in FIG. 11, stimulation with recombinant EGFL7 led to expansion of hematopoietic stem and progenitor cells (HSPCs). This is seen by MTS assay, colony formation, and by an increase in AKT phosphorylation.

Figure 12:
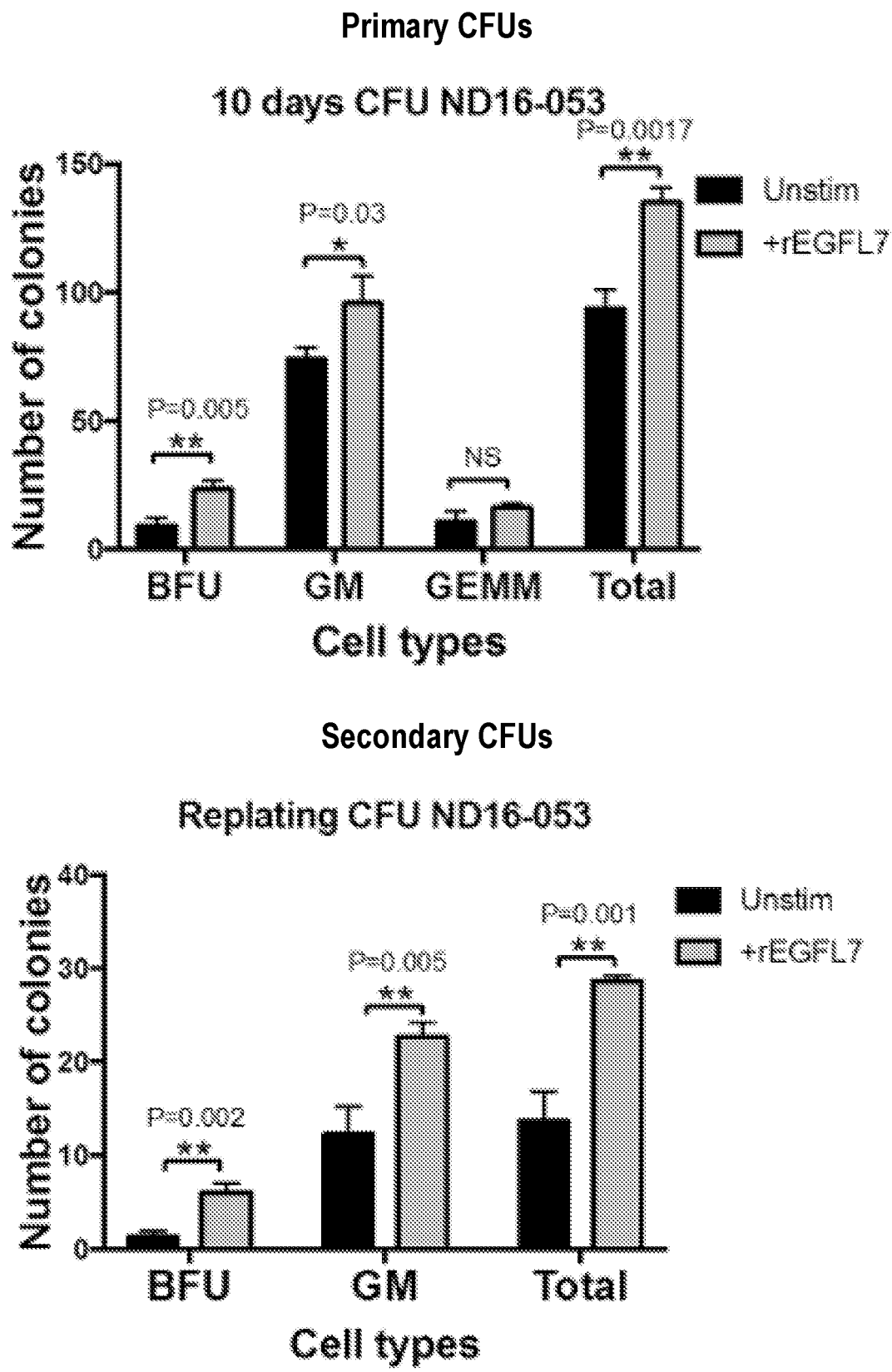
FIG. 12. Recombinant EGFL7 stimulation leads to expansion of primary CFUs and secondary CFUs in human hematopoietic stem and progenitor cells (HSPCs). Left: 500 CD34+CB cells were mixed with methylcellulose medium in the absence or presence of 0.25 µM recombinant human EGFL7 protein and plated onto 2 cm dishes for 10 days. The number of colonies with more than 50 cells was counted under a light microscope. Right: Cells from the first round of CFU assays were harvested, rinsed with SFEM, and pooled. 5000 cells were then mixed with methylcellulose medium in the absence or presence of 0.25 µM recombinant human EGFL7 and plated onto 2 cm dishes for 10 days. The number of colonies with more than 50 cells was counted under a light microscope. Each condition was repeated in triplicate in three independent experiments. *p<0.05, **p<0.01, vs unstimulated control.
Figure 13:
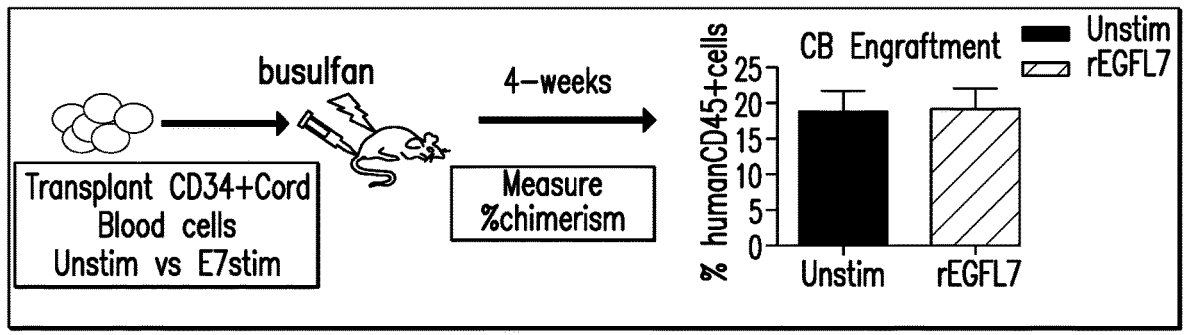
FIG. 13. Recombinant EGFL7 stimulation leads to expansion of human hematopoietic stem and progenitor cells (HSPCs) without losing stem cell potential. CD34+CB cells were cultured in SFEM+10% FBS+100 ng/mL SCF for 48 hours in the presence or absence of 0.25 mM recombinant human EGFL7 protein. $5.0 \times 10^5$ cells of rEGFL7 treated, or control cells, were then transplanted into Busulfan treated NSG mice. Percent chimerism was determined using human anti-CD45-PE and mouse anti-CD45.1-APC antibodies and flow cytometry.

To assess the effect of EGFL7 on normal HSPCs, cord blood (CB) CD34+ cells were cultured in methylcellulose supplemented with rEGFL7 or vehicle control. After 10 days of culture, colonies were scored. It was found that HSPCs cultured with rEGFL7 had increases in both primary and secondary CFUs suggesting a role for EGFL7 in HSPC proliferation and self-renewal (FIG. 12). As shown in FIG. 12, stimulation with recombinant EGFL7 led to an increase burst-forming unit (BFU), granulocyte/macrophage (GM), and granulocyte/erythroid/macrophage/megakaryocyte (GEMM) colony forming units (CFU). Importantly, stimulation with recombinant EGFL7 led to expansion of human hematopoietic stem and progenitor cells (HSPCs) without losing stem cell potential (FIG. 13).

To determine if EGFL7 overexpression leads to alterations in the ability of functionally competent HSCs to engraft lethally-irradiated recipients, competitive repopulation unit (CRU) assays are performed. Briefly, WT (C57Bl/6J-CD45.2+) mouse LSK cells are transduced with Egfl7-eGFP or EV-eGFP control retrovirus. GFP+ cells are isolated using FACS. To determine the differences between Egfl7-eGFP-LSK or EV-eGFP LSK cells in reconstituting the hematopoietic system, limiting dilutions are used of 0 (PBS only), $5.0 \times 10^4$, $1.0 \times 10^5$, $2.5 \times 10^5$, and $5.0 \times 10^5$ GFP+ sorted transduced LSKs transplanted with $2.5 \times 10^5$ BoyJ-WBM cells into lethally irradiated BoyJ recipients. Mice are monitored for 4, 8, 12, and 16 weeks post-transplantation and donor-derived reconstitution is measured through FACS analysis to determine percent chimerism (CD45.2+vs CD45.1+). Results are analyzed using L-Calc software and the stem cell frequency determined by Poisson distribution and the method of maximum likelihood, >5.0% CD45.2+ cells in the PB are considered positive for engraftment. After 16-weeks post-BMT, BM is harvested and $2 \times 10^5$ (GFP+) cells are used in secondary BMT to determine the effect of Egfl7 overexpression on LT-HSCs.

To further validate the role of EGFL7 in HSPC self-renewal, human and mouse HSPCs are cultured in complete methylcellulose media supplemented with and without rEGFL7 (250 nM) protein. After 10-14 days in culture, colony morphology is scored. Colony re-plating assays (up to 3 additional times) are then be performed to determine the effect of EGFL7 on self-renewal capacity using our previous methods[28]. Expt.1D. To examine the consequences of increased EGFL7 on cell proliferation, quiescence, and apoptosis, the following assays are performed; a) BRDU incorporation assays to assess proliferation of EGFL7-eGFP and EV-eGFP transduced human and mouse HSPCs at 24, 48, and 96 hours after GFP+ cell isolation using FACS analysis; b) Membrane labeling experiments to assess the effect of EGFL7 on cellular quiescence using cell Proliferation Dye eFluor® 670 (CPC e670) (ebiosciences) followed by culture for 96 hours. At the end of the culture period, CPC e670 levels are analyzed by flow cytometry. ModFit software is used to fit the data and to determine the percentage of cells in each generation thereby generating a proliferation index; c) Cell cycle analysis using Ki67 and 4,6 diamidino-2-phenylindole (DAPI) staining by FACS; d) Apoptosis (AnnexinV+/7AAD, Casp3 cleavage assay) using human and mouse HSPCs transduced with EGFL7-eGFP or EV-eGFP retrovirus and GFP+ sorted, at 24, 48, 72, and 96-hours.

To determine if Egfl7 overexpression impacts specific lineages within the hematopoietic compartment, full immunophenotypic analysis is performed on mice transplanted with $2 \times 10^5$ EGFL7-eGFP or EV-eGFP transduced WT (CD45.2+) LSK cells co-transplanted with $2.5 \times 10^5$ WBM (CD45.1+) into lethally irradiated mice are evaluated at 4, 8, 12, and 16 weeks post-BMT, using our previously published methods[26]. Full immuno-phenotypic analysis assesses differences in: HSC, MPP1, MPP2, MPP3, and MPP4, CMP, GMP, MEP, T-cells, B-Cells, erythroid, macrophages, and granulocytes which represents the spectrum of more undifferentiated to mature hematopoietic cells.

To determine the direct effects of EGFL7 on hematopoietic subpopulations, immunophenotypically defined HSPCs (HSC, MPP1-4, CMP, GMP, and MEP populations) are isolated using flow sorting, and are stimulated directly with (250 nM) of rEgfl7. Proliferation (Ki-67 and DAPI), quiescence (Ki-67 and DAPI, and CPC e670 membrane labeling), and apoptosis (AnnexinV+/7AAD) are then measured.

Example 4. EGFL7 Antibodies Provide Effective Anti-Leukemic Activity

The prognosis of AML is poor. The long-term overall survival (OS) is only 30-40% in younger (<60 years) and <10% in older (≥60 years) adult AML patients. This highlights the urgent need for novel therapeutic approaches for adult AML patients.

Non-random chromosomal abnormalities (e.g., deletions, translocations) are identified in 50-55% of all AML patients. In contrast, about 45-50% of all AML cases are cytogenetically normal (CN-AML). However, CN-AML represents a highly heterogeneous group in terms of biology and outcome. Recurrent mutations in CN-AML are critical for leukemogenesis. However, in addition to mutations, aberrant gene expression plays a key role in the initiation and maintenance of AML.

EGFL7 is a ~30 KDa secreted protein that plays an important physiological role in angiogenesis. Aberrant expression of EGFL7 has been shown to be involved in carcinogenesis and disease progression of several solid tumors, including liver, breast and lung cancers. However, the role of EGFL7 in AML is unknown.

In the examples above, it was shown that among CN-AML cases, EGFL7 is highly expressed in a large cohort of patients and is associated with poor prognosis. In addition, AML blasts secrete EGFL7 protein. Functionally, EGFL7 protein increases blast cell growth and data demonstrates that EGFL7 impacts on leukemia stem cell (LSC) function by increasing LSC frequency and inducing quiescence. Mechanistically, it was found that EGFL7 binds multiple components of key signal transduction pathways important for leukemia, including NOTCH.

Herein, the inventors identified a novel role of EGFL7 in the leukemic microenvironment. It was found that: 1) BM stromal cells (BMSCs) derived from leukemic mice secreted higher levels of Egfl7 compared to WT BMSCs, and 2) that hypoxia induced further Egfl7 expression in BMSCs, suggesting that the leukemic microenvironment supports cell survival through secretion of Egfl7. Understanding the cross-talk between the microenvironment and leukemic blasts is critical to eradicate AML.

As disclosed herein, targeting primary AML blasts with an anti-EGFL7 antibody (Parsatuzumab) leads to decreases in blast cell growth and increases in NOTCH target gene expression. It was also shown that Parsatuzumab synergizes with the FLT3 inhibitor (Gilteritinib) in AML cell lines and patients. Remarkably, treatment of healthy wild type (WT) mice with the highest reportable dose of Parsatuzumab did not display any significant hematopoietic defects. This is also consistent with in vitro data showing no effect in CB CD34+ cells treated with Parsatuzumab. Furthermore, there have not been any significant hematopoietic side effects in patients with solid tumors treated in phase I/II studies of Parsatuzumab in combination with chemotherapy. Thus, the data indicate that Parsatuzumab exhibits anti-leukemic effects without affecting normal hematopoiesis.

The identification and targeting of signaling pathways that regulate LSC functions like EGFL7, are critical to eradicate AML, since this small population is responsible disease relapse and is resistant to chemotherapy.

The use of a monoclonal antibody against EGFL7 can be used with limited toxicity, leading to better-tolerated and more targeted treatments for CN-AML. Over the past few years there has been a paradigm shift from broad non-specific chemotherapy regimens to targeted therapies based on a more refined list of genetic/molecular markers.

This is the first study to investigate a role for the pro-angiogenic factor, EGFL7, in hematologic malignancies and in the cross-talk between the BM microenvironment and leukemic blasts.

The discovery that EGFL7 is capable of binding to a number of critical signaling molecules important for myeloid biology such as NOTCH, has not been reported in AML.

EGFL7 is a ~30 KDa secreted protein that plays an important physiological role in angiogenesis. Physiological EGFL7 expression and function has mainly been restricted to the endothelial cells in vascularized tissues such as brain, heart, lung and kidney where it regulates endothelial survival, migration, and differentiation. Aberrant expression of EGFL7 has been shown to be involved in carcinogenesis and disease progression of several solid tumors, including glioblastoma, liver, breast, lung, and pancreatic cancers. Overexpression of EGFL7 in solid tumors promotes neo-angiogenesis and sustains tumor growth. Blocking EGFL7 using Parsatuzumab in a genetically engineered mouse model of non-small cell lung cancer decreased tumor size and increased overall survival. However, the role of EGFL7 in AML was previously unknown.

As discussed in the examples above, the following observations were made: 1) Adults older (aged ≥60 years, n=198) or younger (<60 years, n=374)CN-AML patients with high EGFL7 expression were more likely to harbor FLT3-ITD, RUNX1 and double CEBPA mutations than patients with low EGFL7 expression; 2) High EGFL7 expression status associated with lower complete response (CR) rates and shorter OS in both older and younger CN-AML patients, independent form other variables; 3) EGFL7 mRNA and protein expression was higher in CN-AML blasts compared to normal BM, in both human and mouse primary AML samples. Significant increases in the level of serum EGFL7 were found in three of six AML patients tested compared with normal controls (n=6); and 4) Primary AML blasts cultured in vitro were able to secrete EGFL7 protein and culturing primary AML blasts with recombinant EGFL7 (rEGFL7) increased blast cell growth.

EGFL7 Interactome

In order to obtain insights about potential mechanisms by which EGLF7 stimulates AML blast growth, the inventors sought to identify potential EGFL7 interacting proteins. Since other members of the EGFL family of proteins are known to have numerous potential binding partners, an unbiased high-throughput approach was undertaken by performing an antibody interaction array. These arrays have ~400 antibodies hybridized to a membrane. First, protein lysates from AML blasts were incubated with rEGFL7 protein and spotted onto the antibody membranes. Then using an anti-EGFL7-HRP (FIG. 14A) or anti-GST-HRP control (FIG. 14B) antibody, the membranes were developed using standard chemiluminescence detection. Densitometry of the individual spots were determined using ImageJ for both the anti-EGFL7 and anti-GST-HRP control blots. Array data was first log 2 transformed and then normalized by subtracting the mean of the background. After that, a linear mixed model was used for analysis to compare the protein level between anti-EGFL7 Ab array and anti-GST Ab array. Using this strategy, it was found that NOTCH1 was bound significantly to EGFL7 in all three samples (P=1.11E-06).

EGFL7 Binds NOTCH2 and Inhibits its Subsequent Activation

NOTCH signaling is a highly conserved signaling pathway that regulates critical cell processes such as cell fate determination during embryonic development and adult tissue homeostasis. The NOTCH receptor is a single transmembrane protein composed of functional extracellular (EC), transmembrane (TM), and intracellular (IC) domains. There are four different types of NOTCH receptors in mammals, NOTCH 1-4. Signaling through NOTCH requires the activation of these receptors by canonical NOTCH ligands such as JAG1, JAG2, DELTA LIKE, resulting in intracellular cleavage of the NOTCH protein and translocation of the NOTCH-IC to the nucleus where it activates gene transcription. NOTCH signaling has been shown to be important for normal hematopoiesis and stem cell function. However, the precise mechanisms by which NOTCH regulates these cells are still not fully understood. In addition, the regulation of HSPCs by NOTCH signaling is not limited to intrinsic effects within the HSPCs themselves. It was reported that NOTCH signaling modulates HSPC functions by regulating the BM niche. Mutations in the NOTCH receptors causing NOTCH signaling hyperactivation is a major leukemogenic driver for a subset of T cell acute leukemias. However, NOTCH signaling has been shown to have an opposite role in AML. Several groups have shown that NOTCH signaling is silenced in AML and that re-expression leads to disease elimination; however, the mechanism underlying this NOTCH inactivation is unknown. It seems reasonable that decreased NOTCH activation could be the result of decreased levels of NOTCH ligands, insufficient levels of NOTCH receptor expression, or inadequate cleavage and/or translocation of NOTCH-IC to the nucleus to activate target gene transcription.

Figure 14:
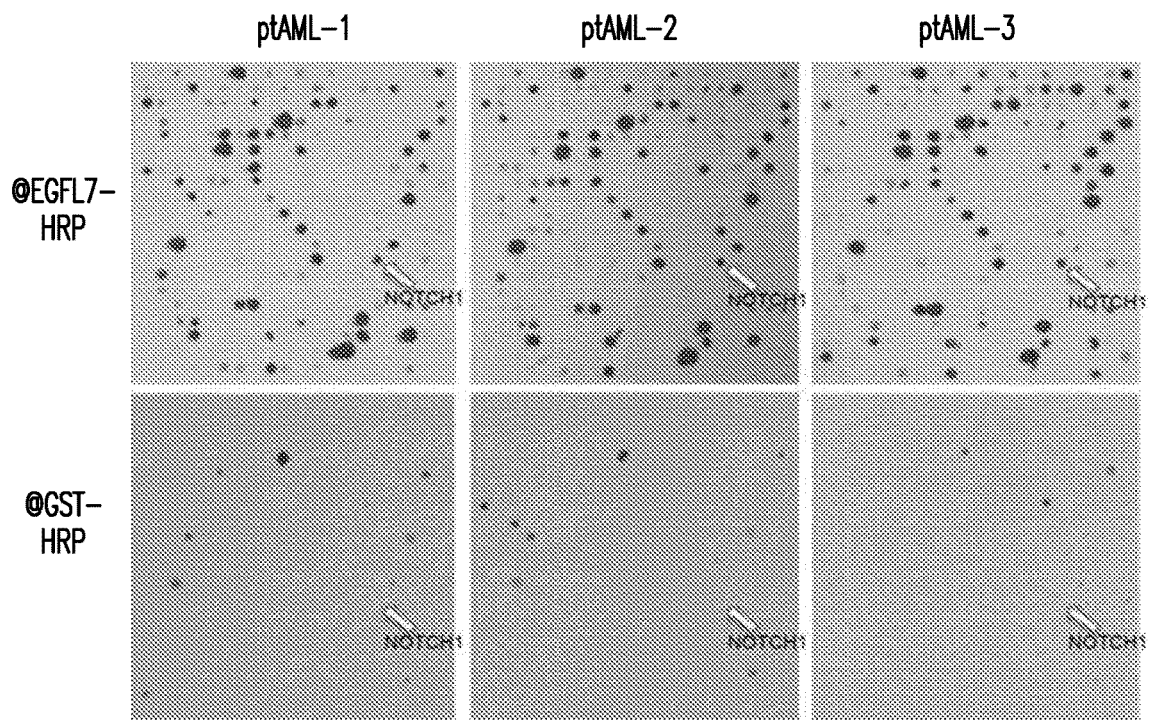
FIG. 14. EGFL7 binding partners. Cell lysate of $5 \times 10^6$ primary AML blasts from each of the indicated AML patient was incubated with an antibody array membrane containing antibodies against 400 signaling molecules. Membranes were then probed with A. anti-EGFL7-HRP (@EGFL7-HRP) or B. anti-GST-HRP (@GST-HRP) antibodies.
Figure 15A:
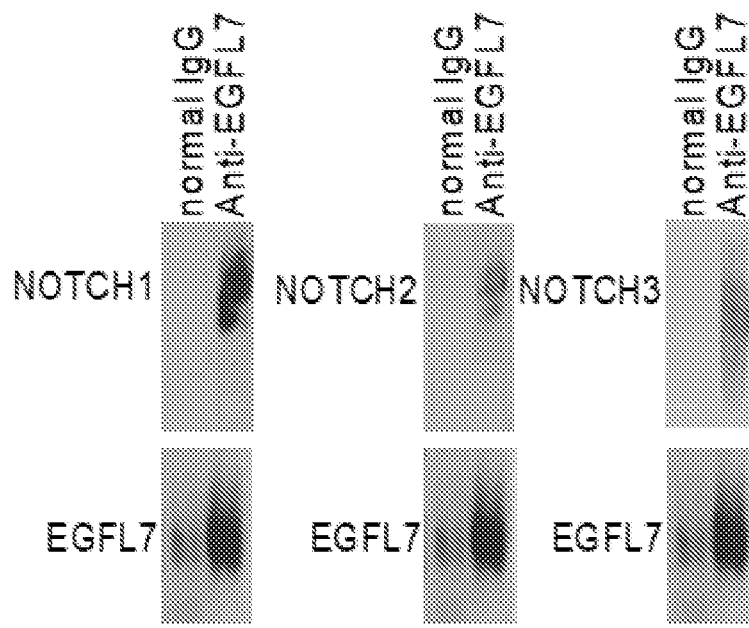
FIG. 15A-15D. EGFL7 binds and antagonizes NOTCH2 signaling.
Figure 15B:
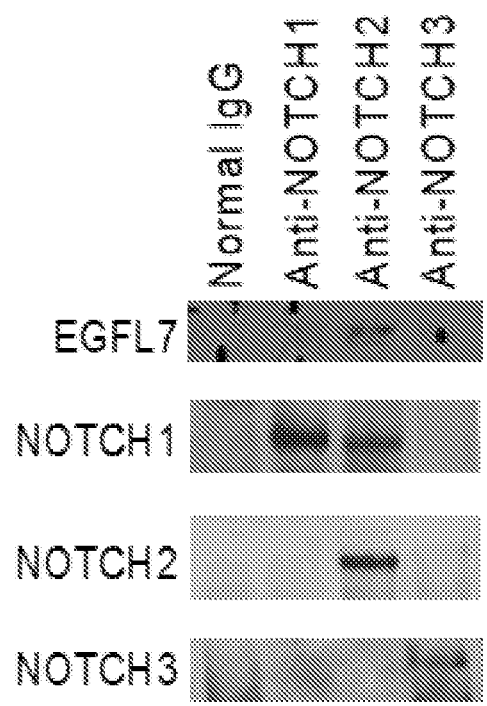
Figure 15C:
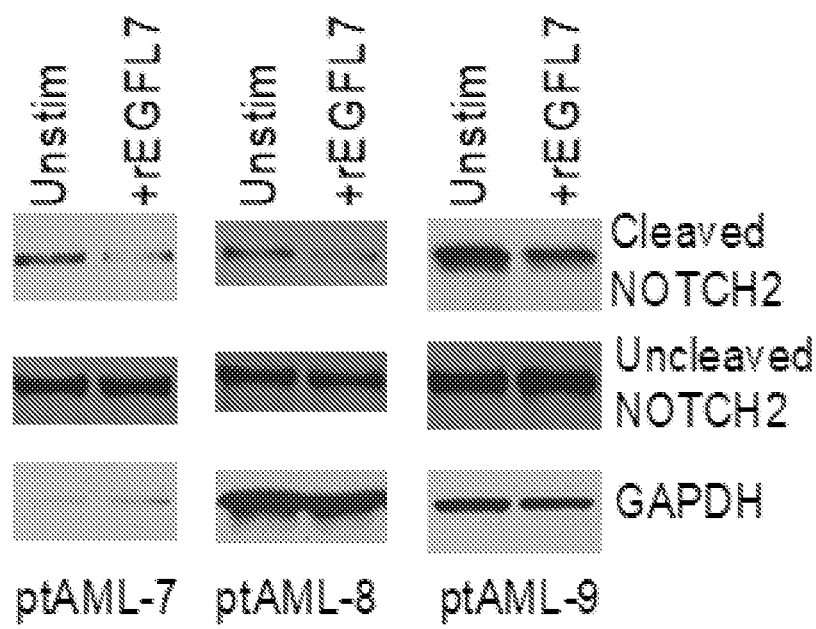
Figure 15D:
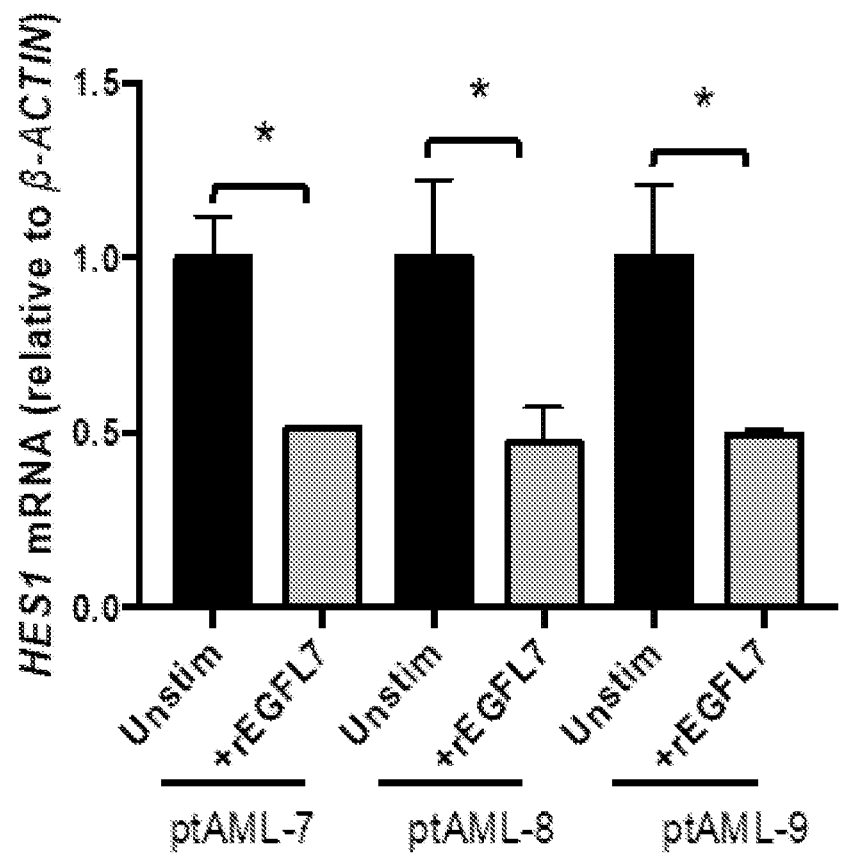

Using this screening approach, NOTCH1 protein was found to be a potential EGFL7 binding protein (FIG. 14). Knowing the important role of NOTCH in AML, the direct interaction between EGFL7 and NOTCH binding was tested. Using the Kasumi-1 cell line, which was found to have measurable levels of EGFL7 protein, co-immunoprecipitation (co-IP) assays were performed and found physical association of EGFL7 with all three NOTCH proteins (FIG. 15A-15B). To determine whether NOTCH2 binding of EGFL7 results in NOTCH pathway activation or inhibition, the levels of NOTCH2 intracellular cleavage (NOTCH2-IC) product that is produced in response to canonical NOTCH2 ligand binding and subsequent activation was examined. It was found at 4 hours post-stimulation with rEGFL7, reduced NOTCH2-IC levels in primary human AML samples with no differences in total NOTCH protein (FIG. 15C). This down regulation in NOTCH2 activity resulted in decreased levels of the NOTCH target gene, HES-1, at 24 hours in primary human AML cells (FIG. 15D). Overall, these data show that EGFL7 overexpression is another possible mechanism by which the NOTCH pathway remains inactive in AML.

Role of EGFL7 in the BM Microenvironment

Figure 16A:
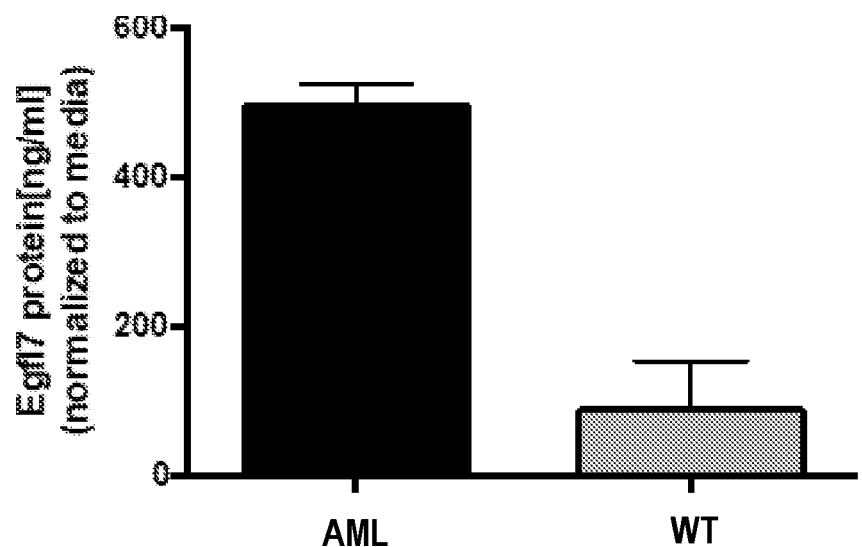
FIG. 16A-16C. EGFL7 in BMSCs.
Figure 16B:
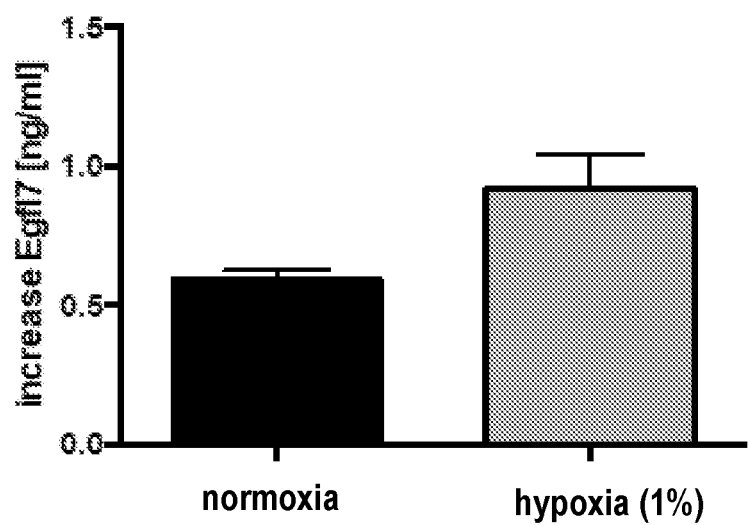
Figure 16C:
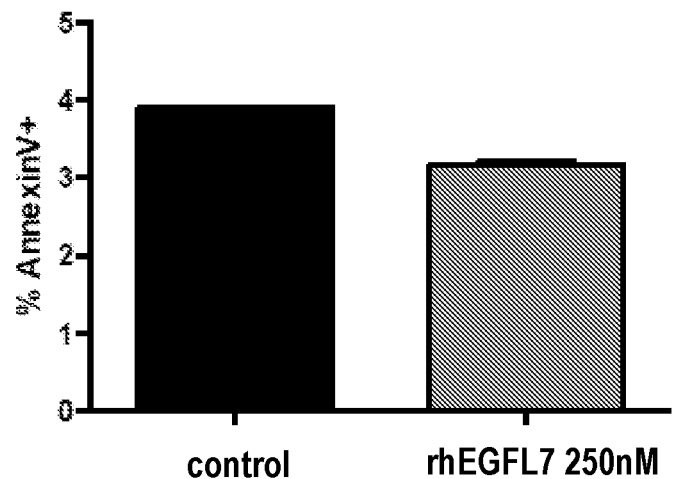

The bone marrow (BM) microenvironment is essential for normal hematopoiesis during the lifespan of an organism. Alterations in the BM microenvironment lead to BM dysfunction such as hematologic malignancies and bone marrow failure. Within the BM microenvironment HSPCs reside in special 'niches' alongside different cell types of bone marrow stromal cells (BMSCs) comprising: mesenchymal stem cells (MSC), MSC-derived osteoclasts, osteoblasts, CXCL12-abundant reticular (CAR) cells, endothelial cells, perivascular nonmyelinating Schwann cells, Nestin+ MSCs, and Leptin receptor-expressing cells. EGFL7 has been shown to be secreted by endothelial cells lining the luminal side of blood vessels and recently, Egfl7 has been shown to be expressed by osteoblasts and osteoclasts resulting in paracrine regulation of endothelial cells to promote angiogenesis in bone. To determine whether BMSCs secrete Egfl7 protein, BMSCs were harvested from WT and leukemic mice (Mll PTD; Flt3 ITD murine AML model described below) using previously established methods. ELISA was then performed to determine the levels of Egfl7 protein secretion in cell culture media from WT and leukemic (dKI) BMSCs. It was found that the leukemic BMSCs secrete significantly higher levels of Egfl7 compared to WT BMSCs (FIG. 16A). Since leukemic BM microenvironment is known to be highly hypoxic, it was determined whether hypoxia was responsible for the increased Egfl7 secretion by the leukemic BMSCs as a possible mechanism for cell survival in response to stress. BMSCs from WT mice were harvested and cultured in hypoxic conditions (1%O2) and compared to BMSCs cultured in normoxia (21%O2). Significant increases were found in Egfl7 secretion by the BMSCs exposed to hypoxia (FIG. 16B). Furthermore, it was found that rEGFL7 stimulation of BMSCs resulted in decreases in apoptosis measured by AnnexinV/PI staining (FIG. 16C). Altogether, these data indicate that EGFL7 is secreted by leukemic BMSCs and that hypoxia induces EGFL7 expression in BMSCs to enhance cell survival in response to environmental stress.

Role of EGFL7 in Leukemia Stem Cells (LSCs)

Figure 17A:
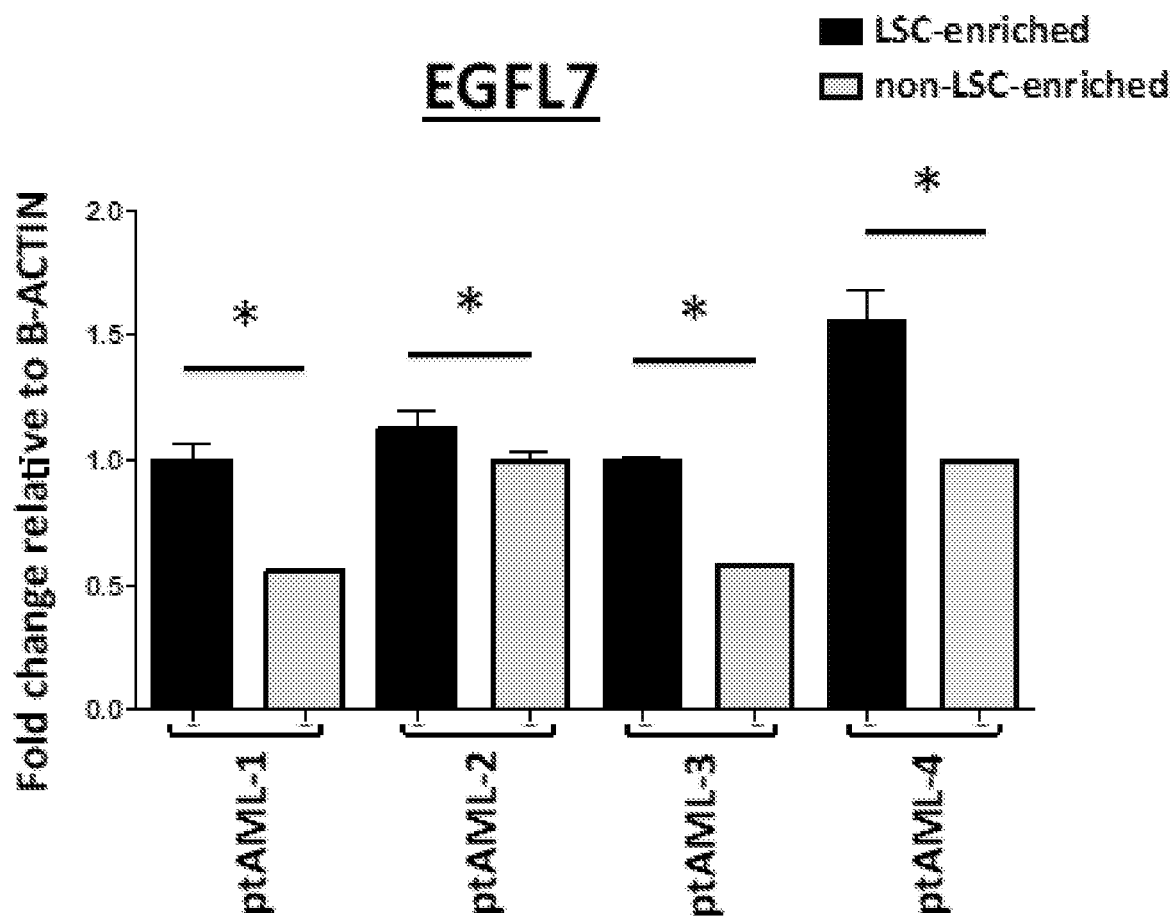
FIG. 17A-17C. EGFL7 in LSCs.
Figure 17B:
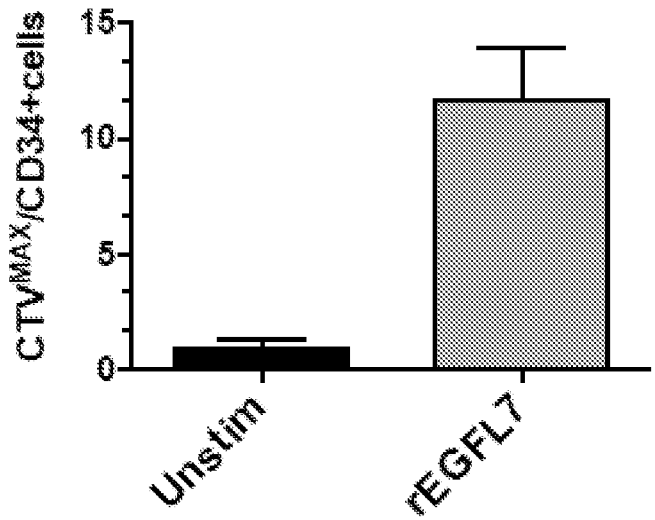
Figure 17C:
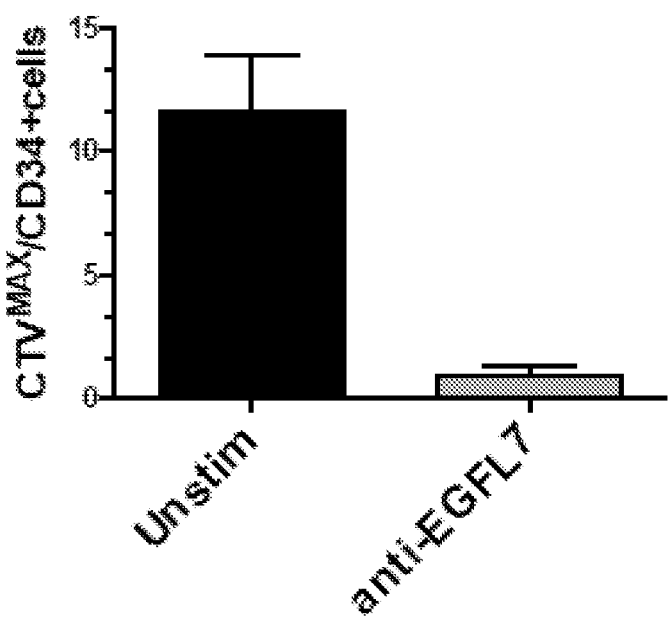

A morphologically homogenous and functionally static blast population present in the BM and blood of individual AML patients has now evolved into the current perspective of multiple dynamic and heterogeneous cell subpopulations which includes the bulk blast population and the relatively rare leukemia initiating cells (LICs) also referred to as LSCs. Thus, targeting both LSCs and bulk blasts is necessary for complete eradication of the disease. To determine whether EGFL7 has a role in LCS, the LSC-enriched population was first determined within each AML patient sample using long-term colony initiating cell (LTC-IC) assays. Then, using qRT-PCR, the levels of EGFL7 were measured in each subpopulation and found that EGFL7 was significantly increased in the LSC-enriched population of each patient (FIG. 17A). Next, to determine whether EGFL7 has a role in LSC function, CD34+ cells were isolated and stimulated them with rEGFL7 protein and performed LTC-IC assays. It was found that CD34+ AML cells cultured with rEGFL7 had an increase in the number of LSCs compared to negative controls (1 LSC in 41 cells of rEGFL7 stimulated cells; compared to 1 in 1500 cells in unstimulated controls). To determine whether EGFL7 regulates LSC functions such as cellular quiescence, membrane-labeling retention experiments were performed with cell-trace violet dye (CTV). Briefly, CD34+ primary AML patient cells were harvested, labeled with CTV, and treated with rEGFL7 protein or Parsatuzumab) using previously published methods to determine the number of quiescent cells after treatment. It was found that CD34+ AML cells treated with rEGFL7 resulted in an increase in the number of quiescent cells ($CTV^{MAX}$) compared to unstimulated controls (FIG. 17B) while cells treated with Parsatuzumab resulted in a decrease in the number of quiescent AML cells (FIG. 17C). Altogether, these data show a role for EGFL7 in LSC functions in AML.

Figure 18A:
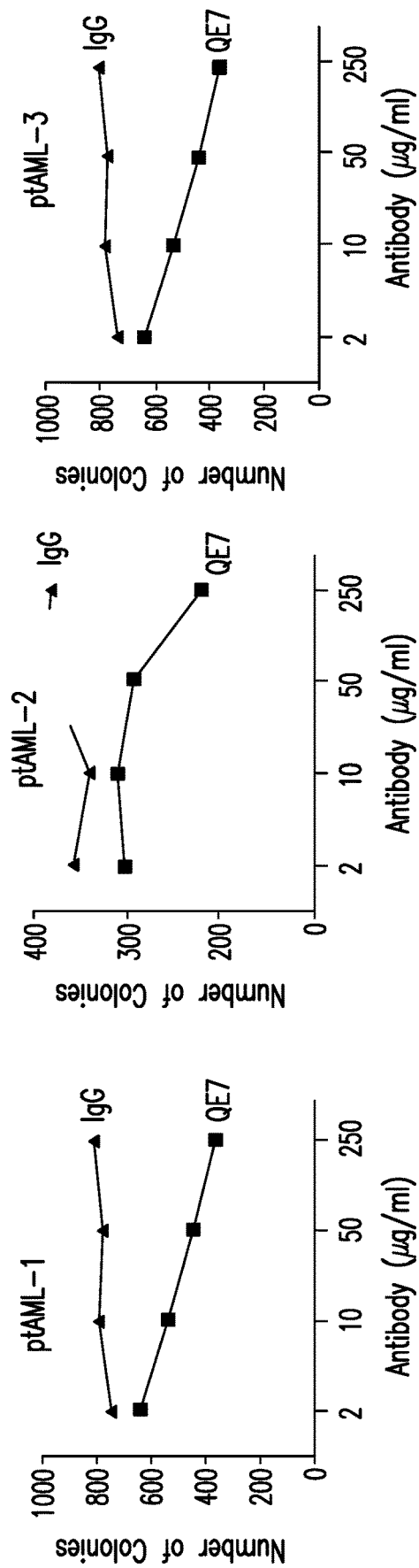
FIG. 18A-18B. Parsatuzumab decreases blast growth and activation of NOTCH downstream signaling.
Figure 18B:
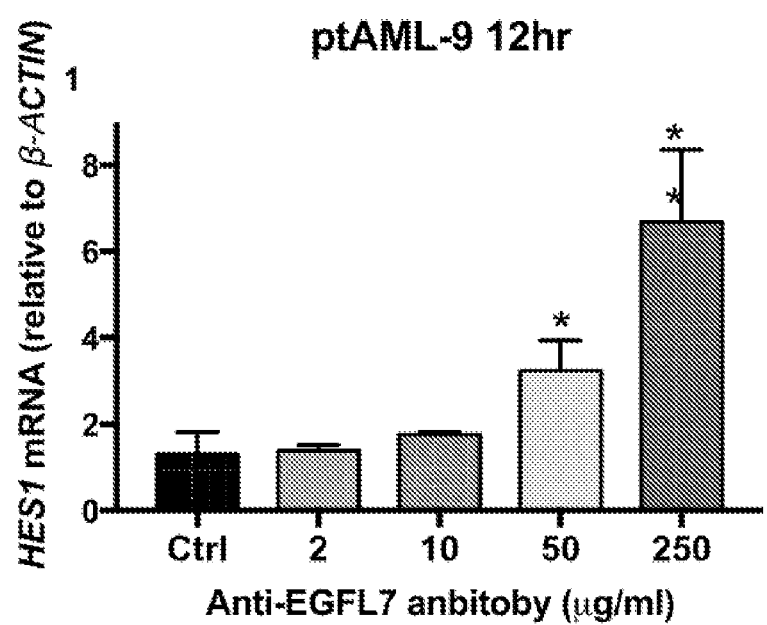

Targeting EGFL7 in Primary AML Blasts Using Parsatuzumab Results in Decreased Blast Growth and Activation of NOTCH Downstream Targets To determine whether inhibiting EGFL7 activity with a blocking antibody represents a potential new target for therapy in AML, primary AML patient samples were treated with Parsatuzumab. This antibody had been shown previously to prolong survival in solid tumor murine models by inhibiting angiogenesis. Primary AML blasts (n=4) were cultured in the presence of increasing concentrations of anti-EGFL7 or IGg1 control antibody for 4 hours and then plated for 10 days in methylcellulose. A dose dependent decrease in blast growth was found, represented by the number of CFUs in Parsatuzumab treated samples compared to IGg1 control (FIG. 18A). To determine whether inhibition of EGFL7 led to reactivation of NOTCH target genes, the expression of HES-1 mRNA was measured by real time RT-PCR and found significant increases in HES-1 expression at 4 and 24 hours after addition of Parsatuzumab compared to IGg1 controls (FIG. 18B).

Parsatuzumab Synergizes with the FLT3 Inhibitor Gilteritinib in AML Cell Lines

Figures 19A, 19B, 19C:
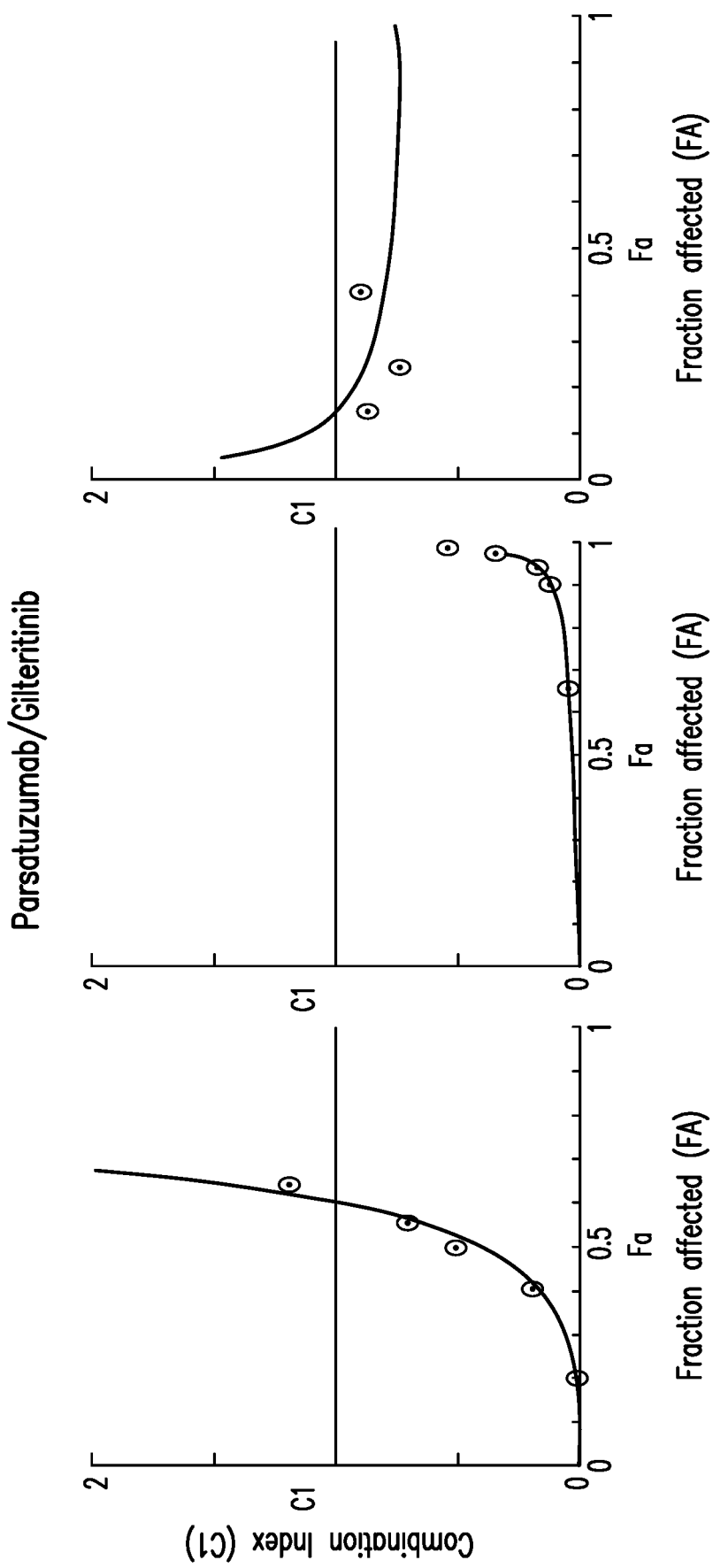
FIG. 19A-19C. Parsatuzumab synergizes with the FLT3 inhibitor Gilteritinib in AML cell lines MV4-11 (FIG. 19A), Molm13 (FIG. 19B), and primary patient sample (FIG. 19C), (values less than 1=synergy).

Because AML is a clinically and molecularly complex disease, it was investigated whether adding an effective drug, such as the powerful FLT3 inhibitor Gilteritinib to Parsatuzumab, enhances or improves its anti-leukemic effects in AML. The reason a FLT3 inhibitor was chosen is based on the fact that patients with FLT3-ITD mutations express high levels of EGFL7MRNA expression. Gilteritinib is a potent small molecule next generation FLT3/AXL inhibitor with activity against both FLT3-ITD and FLT3-D835 mutations. A recent phase I/II study of Gilteritinib in AML showed that the drug is tolerable, safe, and exhibits consistent, potent FLT3 inhibition. Patients with FLT3-ITD AML receiving doses ≥80 mg/d had an overall response rate of 52% and longer OS than historic controls. To assess whether the combination of Parsatuzumab and Gilteritinib enhanced cytotoxicity against leukemic cells, MV4-11 and MOLM-13 cell lines (Both FLT3-ITD+) were initially treated with Parsatuzumab and Gilteritinib at the IC-50 for both drugs and two-fold dilutions of their individual IC50 value, and apoptosis was measured using the Annexin/PI assay at 48 hours. As shown in FIG. 19A-19B, concomitant treatment of Parsatuzumab with Gilteritinib resulted in synergy (values less than 1=synergy) as determined by the Chou-Talalay method. Similar results were observed using a primary AML sample with FLT3-ITD mutation (FIG. 19C).

Toxicity of Parsatuzumab on Normal Hematopoiesis

Figure 20A:
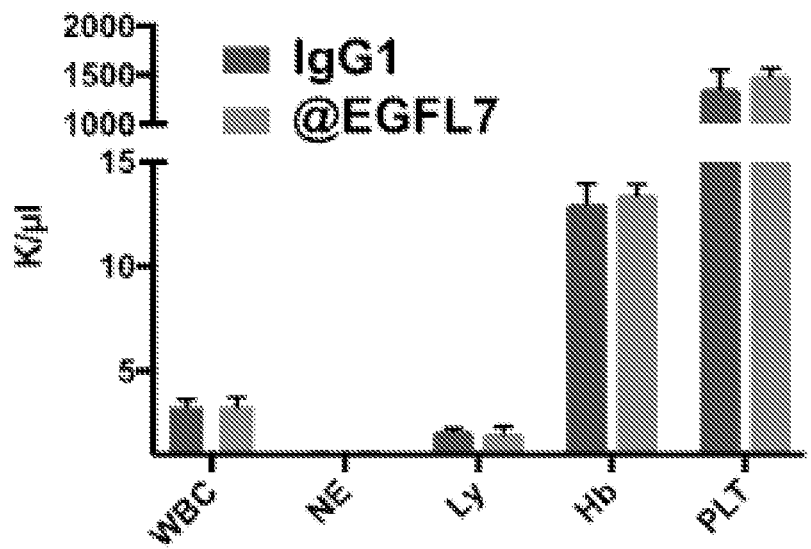
FIG. 20A-20B. WT mice were treated with 50 mpk twice weekly of Parsatuzumab (@EGFL7) or IgG1 control.
Figure 20B:
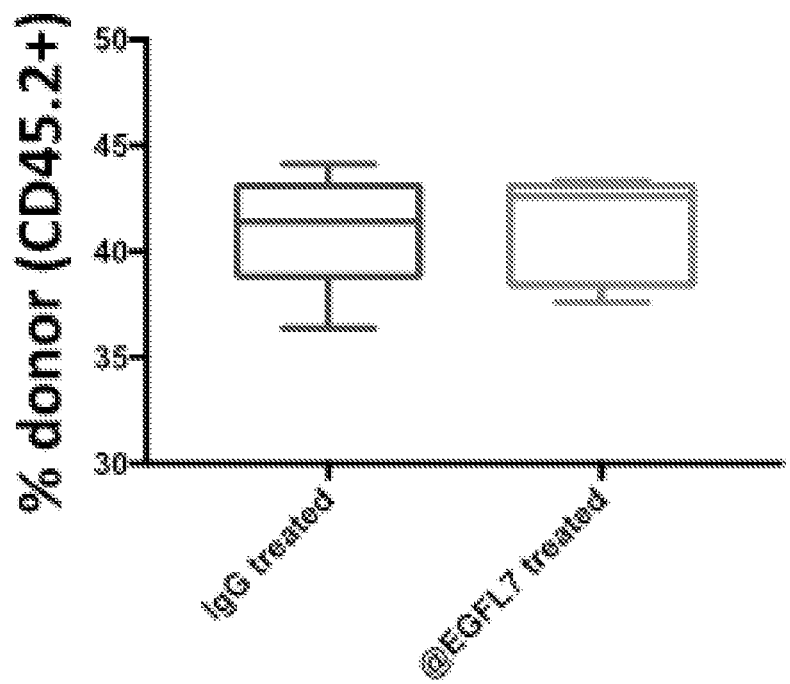

To assess the toxicity of Parsatuzumab on normal hematopoiesis, wild type (C57Bl/6J) mice were treated with Parsatuzumab (n=4) and IgG1 control (n=4) with the highest dose previously tested at 50 mpk twice a week for two weeks. Parsatuzumab targets both human and mouse EGFL7 protein. After two weeks of treatment, blood, spleen and BM were harvested and full phenotypic characterization was performed to assess toxicity. Full differential complete blood counts (CBCs) demonstrated no significant changes between the Parsatuzumab-treated and IgG1 controls (FIG. 20A). Full immunophenotypic examination of BM populations was also performed (data not shown due to space constraints). These analyses revealed no significant changes in any hematopoietic stem and/or progenitor populations. To functionally test the effect of Parsatuzumab on normal HSPCs, competitive repopulation BM transplantation (BMT) assays and CFU assays were performed. For competitive BMT, 2×10^6 WBM was harvested from Parsatuzumab and IgG1 treated mice (CD45.2) with 2×10^6 BoyJ (CD45.1) WBM and transplanted into lethally irradiated BoyJ recipients. Three weeks post-BMT recipient mice were bled and flow cytometry was performed to determine donor chimerism (CD45.1 vs CD45.2), it was found no significant differences in the mice transplanted with Parsatuzumab treated BM than mice transplanted with IgG1 control (FIG. 20B). BM from Parsatuzumab and IgG1 treated BM also showed no significant changes in the number of CFUs or types of colonies formed (due to space constraints data not shown). These results were validated in human HSPCs using cord blood (CB) CD34+ cells treated with Parsatuzumab and IgG1 control in vitro and consistent with the in vivo treated mouse date, found no significant changes in the numbers or types of colonies. These data indicate that Parsatuzumab treatment in vitro or in vivo does not affect normal HSPC and hematopoiesis.

EGFL7 Contribution to Initiation and/or Maintenance of AML

Figure 21A:
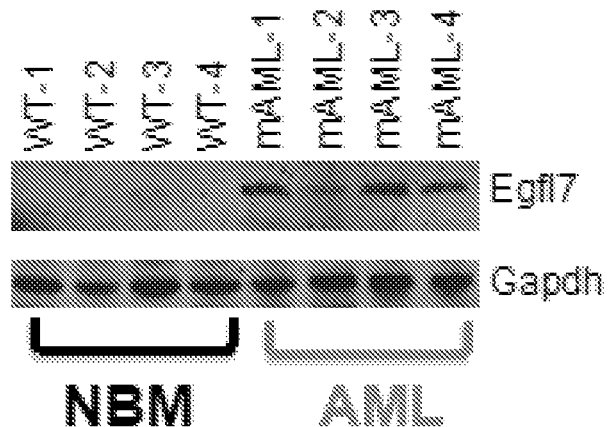
FIG. 21A-21B. EGFL7 is upregulated in our mouse AML model.
Figure 21B:
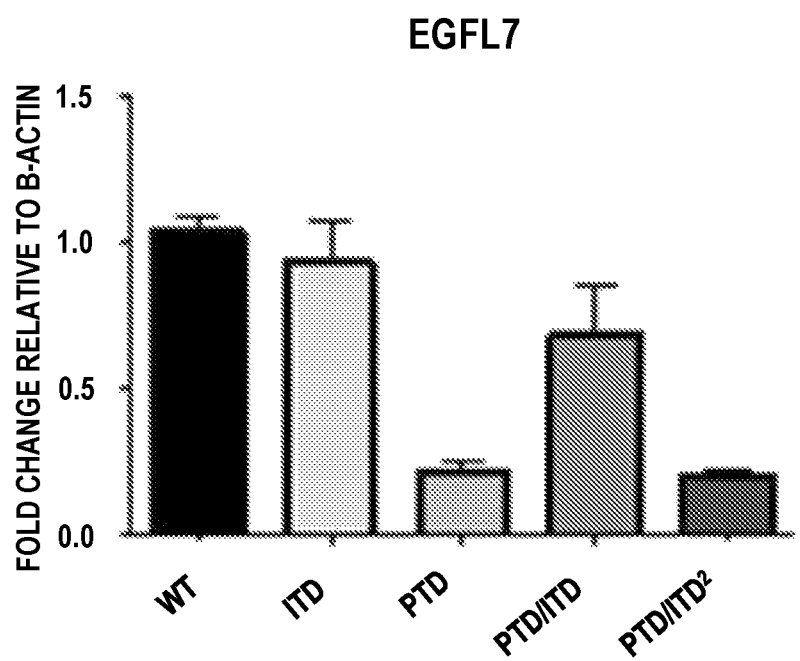

A germline double knock in Mll-PTD; Flt3-ITD primary murine model of AML was developed by crossing the $Mll^{PTD/WT}$ knock-in mice with mice that harbor either one copy ($Flt3^{ITD/WT}$) or two copies ($Flt3^{ITD/ITD}$) of the Flt3-ITD. One important difference observed between these two genotypes, was that the $Mll^{PTD/WT}$; $Flt3^{ITD/ITD}$ mice develop disease significantly earlier than $Mll^{PTD/WT}$; $Flt3^{ITD/WT}$ mice (19 vs. 49 weeks). However, both genotypes develop leukemia with ~100% penetrance and have increased Egfl7 in their leukemic blasts (FIG. 21A). Although Egfl7 expression is increased in primary leukemic blasts from the Mll-PTD; Flt3-ITD mice compared to WT controls, Egfl7 is not increased in pre-leukemic (3 months old) Mll-PTD; Flt3-ITD (PTD/ITD and PTD/ITD$^2$) BM or single mutant controls (ITD or PTD alone) compared to WT control (FIG. 21).

Summary

As disclosed herein, it was shown that among CN-AML cases, EGFL7 is highly expressed in a large cohort of patients and is associated with poor prognosis. Remarkably, EGFL7 is also highly expressed in the LSC-enriched subpopulations of AML patients. It was further demonstrated that AML blasts and leukemic BMSCs secrete EGFL7 protein and that hypoxia induces EGFL7 expression in BMSCs. Functionally, treatment of blasts or LSC from primary AML patients with rEGFL7 results in enhanced blast cell growth, increases LSC frequency and induces quiescence. Mechanistically, it was found that EGFL7 binds multiple components of key signal transduction pathways important for leukemia, including NOTCH. Altogether, these data show a role for EGFL7 in leukemogenesis by inducing blast proliferation, promoting LSC functions and regulating the BM microenvironment. It was demonstrated that targeting primary AML blasts with EGFL7 antibody (Parsatuzumab) leads to decreases in blast cell growth without affecting normal hematopoiesis. In addition, synergism was found between Parsatuzumab and Gilteritinib (a FLT3 inhibitor).

Example 5. EGFL7 Antagonizes NOTCH Signaling in AML

Epidermal growth factor-like domain 7 (EGFL7) is a secreted protein and has been shown to have a role in acute myeloid leukemia (AML) in the above examples. However, the mechanism by which EGFL7 functions in AML has not been explored. It was found herein that EGFL7 binds many different signaling proteins important for hematopoiesis and cancer including NOTCH1 and NOTCH2. Stimulation of blasts with recombinant EGFL7 (rEGFL7) protein resulted in decreases in NOTCH target genes and reduction in the levels of activated NOTCH intracellular domain (NICD). Conversely, blasts treated with an anti-EGFL7 blocking antibody (Parsatuzumab) resulted in reactivation of NOTCH signaling, and increases in cell differentiation and apoptosis. Competitive ligand binding assay using rEGFL7 and DLL4, a canonical NOTCH ligand, showed rEGFL7 inhibits DLL4 activation of NOTCH signaling. Conversely, Parsatuzumab in combination with DLL4 resulted in significant increases of NOTCH activation and apoptosis. Using a mouse xenograft model, in vivo treatment with Parsatuzumab results in prolonged survival. Overall, these data demonstrate that EGFL7 contributes to silencing NOTCH signaling in AML by antagonizing canonical NOTCH ligand binding. Reactivation of NOTCH signaling in vivo using an anti-EGFL7 blocking antibody results in prolonged survival, and supports EGFL7 antibodies as an important novel therapy for patients with AML.

Background

NOTCH signaling is an evolutionarily conserved pathway and plays an important role in regulating cell-fate determination during development and maintenance of adult tissue homeostasis[1,2]. The NOTCH receptor is a single transmembrane protein composed of a functional extracellular (EC), transmembrane (TM), and intracellular (IC) domains. There are four different types of NOTCH receptors in mammals, NOTCH1, 2, 3 and 4[3]. Signaling through NOTCH requires the activation of these receptors by binding canonical NOTCH ligands such as JAG1, JAG2, DELTA like 1 (DLL1), DLL3, and DLL4, resulting in intracellular cleavage of the NOTCH protein to the truncated form (NICD), which then translocates to the nucleus to activate gene transcription[2,4,5]. In addition to the canonical ligands, many non-canonical NOTCH ligands lacking the Delta, Serrate, and Lag2 (DSL) domain comprise a group of diverse proteins including integrins and glycosylphosphatidylinositol (GPI)-linked membrane as well as secreted proteins[2]. NOTCH signaling has been shown to be important for normal hematopoiesis and stem cell function[1,3,6-8]. Mutations in the NOTCH receptors causing NOTCH signaling hyperactivation is a major driver of leukemogenesis for a subset of T cell acute leukemia[1]. However, NOTCH signaling has been shown to have the opposite role in AML[9,10].

Several groups have shown that NOTCH signaling is silenced in AML and that re-activation of NOTCH signaling results in blast differentiation and disease elimination[10]. However, the mechanism underlying this NOTCH inactivation has not been determined[9-11].

Epidermal growth factor-like domain 7 (EGFL7) is a secreted protein and plays an important role in angiogenesis by regulating the growth, proliferation and migration of endothelial cells[12-14]. In solid tumors, it has been shown that EGFL7 is overexpressed and associates with a more aggressive disease phenotype[15]. As described in the examples above, EGFL7 is up-regulated in primary AML blasts and that high EGFL7 mRNA expression correlates with shorter event-free and overall survival of AML patients. Moreover, as described above, it was demonstrated that AML blasts were able to secrete EGFL7 protein and treatment of primary AML blasts with rEGFL7 in vitro leads to increases in leukemic blast cell growth. These data show an important clinical and biological role for EGFL7 in AML. However, the molecular mechanisms involving EGFL7-mediated leukemogenesis has not been thoroughly examined[13,17-19]. EGFL7 has been shown to bind NOTCH receptors and either activate or antagonize canonical NOTCH signaling[13,19,20]. Whether EGFL7 represses or activates NOTCH signaling in AML has not been determined.

Summary

The data herein show that EGFL7 is able to bind many different signaling proteins important for hematopoiesis and cancer including NOTCH. These findings were confirmed using co-immunoprecipitation assays and found that EGFL7 binds NOTCH receptors on primary AML blasts and cell lines. Stimulation of blasts with recombinant EGFL7 (rEGFL7) protein results in decreases of NOTCH target genes and reduction in the levels of activated NOTCH intracellular domain (NICD). Conversely, blasts treated with an anti-EGFL7 blocking antibody (Parsatuzumab) results in reactivation of NOTCH activity resulting in increases in expression of downstream target genes, NICD levels, and apoptosis. Primary blasts treated with a gamma-secretase inhibitor blocked Parsatuzumab induced NOTCH activation, substantiating the findings that NOTCH signaling is downstream of EGFL7 activity in AML. It was found that DLL1 and DLL4-mediated activation of NOTCH signaling can be inhibited by rEGFL7, while Parsatuzumab treatment resulted in enhanced activation of NOTCH by these ligands. Overall, these data support that NOTCH acts as a tumor suppressor in AML. EGFL7 silences NOTCH signaling by antagonizing canonical NOTCH ligand binding in AML. Furthermore, in vivo treatment of an AML xenograft mouse model with Parsatuzumab results in prolonged survival showing that blocking EGFL7, and subsequent NOTCH reactivation, represents a novel therapeutic approach for patients with AML.

Materials and Methods

Reagents and Cells

Recombinant human DLL4 (Fc chimera, ab108557) and natural human IgG Fc fragment proteins (ab90285) were obtained from Abcam (Cambridge, Mass., USA). Anti-human EGFL7 therapeutic antibody (Parsatuzumab) was obtained from Creative Biolabs (Shirley, N.Y., USA). Normal human immunoglobulin (Immune Globulin, 3036917) was purchased from Grifols (Research Triangle Park, N.C., USA). γ-secretase inhibitor (Avagacestat, BMS-708163) was obtained from Selleckchem (Houston, Tex., USA). OP9 and OP9-DLL1 mouse stromal cells were cultured in MEM alpha/GlutaMAX medium (Gibco) supplemented with 20% FBS.

Primary AML Blasts and AML Cell Lines

THP-1 and Kasumi-1 cells were purchased from American Type Culture Collection (ATCC, Manassas, Va., USA); EOL-1 cells were purchased from Deutsche Sammlung von Mikroorganismen and Zellkulturen (DSMZ, Braunschweig, Germany). AML cell lines were cultured in RPMI1640 (Gibco) supplemented with 10-20% FBS (Gibco). Blasts from AML patients were maintained in SFEM (StemCell Technologies, Vancouver, USA) medium supplemented with 10% FBS and 1× StemSpan CC100 cytokine cocktail (StemCell Technologies) unless otherwise noted. AML blasts used in the experiments were obtained from apheresis blood samples collected from patients treated at The Ohio State University (OSU) and stored in the OSU Leukemia Tissue Bank. Informed consent to use the tissue for investigational studies was obtained from each patient according to OSU institutional guidelines.

AML Xenograft Mouse Model

All studies using animals were carried out in accordance with the OSU institutional guidelines for animal care and under protocols approved by the OSU Institutional Animal Care and Use Committee. All mice used in the experiments were between 8 and 10 weeks of age. Female NOD-scid IL2Rg$^{null}$ (NSG) mice were transplanted with 10×10$^6$ EOL-1 cells. Two weeks post-transplant mice were treated with Parsatuzumab or IgG1 control (4 mice per group; dosage 50 mg/kg intraperitoneal), three times per week. Mice were monitored closely for clinical signs of leukemia such as weight loss and hind limb paralysis.

RNA Expression Analysis

Total RNA was extracted using Trizol reagent (Invitrogen, Carlsbad, Calif., USA). cDNA was synthesized using SuperScript III reagents (Invitrogen) according to the manufacturer's instruction. Quantitative Real-Time RT-PCR was performed using commercially available TaqMan Gene Expression Assay primers and the 7900HT Fast Real-Time PCR System (Applied Biosystems, Foster City, Calif., USA). The expression levels of target genes were normalized to β-ACTIN. Relative expression was calculated by using the comparative $2^{-\Delta\Delta ct}$ method.

Detection of EGFL7 Interacting Proteins by Antibody Array

Potential EGFL7 interacting proteins were probed with Signal Transduction Antibody Array containing antibodies against 400 proteins from Hypomatrix (Cat. HM3000, Worcester, Mass., USA) according to the manufacturer's protocol. In brief, cells (5-10×10$^6$) were lysed in 500 μl of Pierce Co-Immunoprecipitation lysis buffer supplemented with protease and phosphatase inhibitors (Roche). Cell lysis was performed on ice for 20 min and the cell lysate was sonicated for 5 sec three times. After centrifugation at 14,000 g 4° C. for 15 min, the cell lysate supernatant was diluted to 3 ml in lysis buffer containing 0.1% dry milk and 10 nM recombinant human EGFL7 protein from PeproTech (Rocky Hill, N.J., USA), added to the antibody array membrane previously blocked with 5% dry milk in TBST buffer for 2 h, and incubated at 4° C. for 2 h on a flat shaker with slow shaking. Following wash five times with TBST buffer, the membrane was incubated with HRP-conjugated anti-EGFL7 antibody from Bioss (Woburn, Mass., USA) at room temperature for 2 h and developed using ECL Select Western Blotting Detection Reagent (GE Healthcare).

Protein Co-Immunoprecipitation

Cells (1-5×10$^6$) were lysed in 400 μl of Pierce Co-Immunoprecipitation lysis buffer (Thermo Scientific) supplemented with protease and phosphatase inhibitors (Roche). Cell lysis was performed on ice for 20 min and the cell lysate was sonicated for 5 sec three times. After centrifugation with 14,000 g at 4° C. for 15 min, the cell lysate supernatant was transferred to new tubes immediately and added to 50% Protein G Plus/Protein A agarose beads (EMD Millipore, Tremecula, Calif., USA) with a ratio of 100 μl for a 1 ml sample solution. After incubation with rotation at 4° C. for 1 h, and the mixture was centrifuged at 14,000 g for 10 min at 4° C. The supernatant was transferred to new tubes, added with 2-20 μg antibody and incubated on rotating shaker at 4° C. overnight. After centrifugation, the supernatant was incubated with 50 μl protein A/G agarose at 4° C. with rotation for 2 h. The agarose beads were washed five times with ice-cold Pierce Co-Immunoprecipitation lysis buffer. Then 20 μl 2× loading buffer was added, boiled for 5 min and subjected to Western blotting. The corresponding normal antibodies were applied as negative control for CO-IP.

Western Blot Analysis

Cells were lysed in 100 μl of Pierce RIPA buffer (Cat. #8990, Thermo Scientific) supplemented with protease and phosphatase inhibitors (Roche) on ice for 20 min. After centrifuge at 14000 g for 15 min at 4° C., the supernatant was transferred into a new tube, mixed with 20 μl of 5× Laemmli sample buffer containing 5% β-mercaptoethanol and heated at 95° C. for 5 min. Equal volume of samples (10-30 μl) were separated in precast SDS gel (Bio-Rad) and transferred onto nitrocellulose membrane (Bio-Rad). Membrane was blocked by freshly prepared 5% dry milk made in TBST buffer (Bio-Rad) at room temperature for 1 h and then incubated overnight at 4° C. in a primary antibody. Following wash three times with TBST buffer, the membrane was incubated with secondary HRP-conjugated antibody at room temperature for 1 h. Immunoreactive bands were detected using ECL Select Western Blotting Detection Reagent (GE Healthcare). Mouse anti-EGFL7 (LS-C153302) and rat anti-EGFL7 (LS-C40134) antibodies were from LifeSpan BioSciences (Seattle, Wash., USA); goat anti-EGFL7 (sc-34116) and rabbit anti-GAPDH antibodies were purchased from Santa Cruz Biotechnology (Santa Cruz, Calif., USA); rabbit anti-NOTCH1, NOTCH2, NOTCH3, NICD, 13-TUBULIN and HES1 antibodies were obtained from Cell Signaling Technology (Boston, Mass., USA). HRP-conjugated sheep anti-mouse, goat anti-rat, donkey anti-rabbit, and donkey anti-goat secondary antibodies were bought from GE Healthcare.

Cell Proliferation, Apoptosis and Differentiation.

For the evaluation of apoptosis, cells were stained with Annexin V and 7-AAD as previously described[16, 21] For the evaluation of cell proliferation, AML cell lines were incubated with BrdU, fixed, permeabilized and stained with APC-conjugated anti-BrdU antibody, according to the instructions of the manufacturer (BD Biosciences) and as previously described[16, 21] The proliferating fraction of the cells (i.e., the BrdU positive cells) was evaluated with flow cytometry (LSRII, BD Biosciences). For cell differentiation analysis, cells were stained with an anti-CD11B antibody (BD Biosciences) and analyzed by flow cytometry.

Statistical Analysis

Two-tailed student's t tests were performed using GraphPad Prism version 7 (Graphpad Software, San Diego, Calif.) to analyze in vitro and in vivo experiments unless otherwise noted. P values <0.05 were considered significant. Overall survival for the mouse AML xeongraft model was calculated using the Kaplan-Meier method, and survival curves were compared by the log-rank test.

Results
EGFL7 Interacts with NOTCH Receptors in AML Cells

Figure 22:
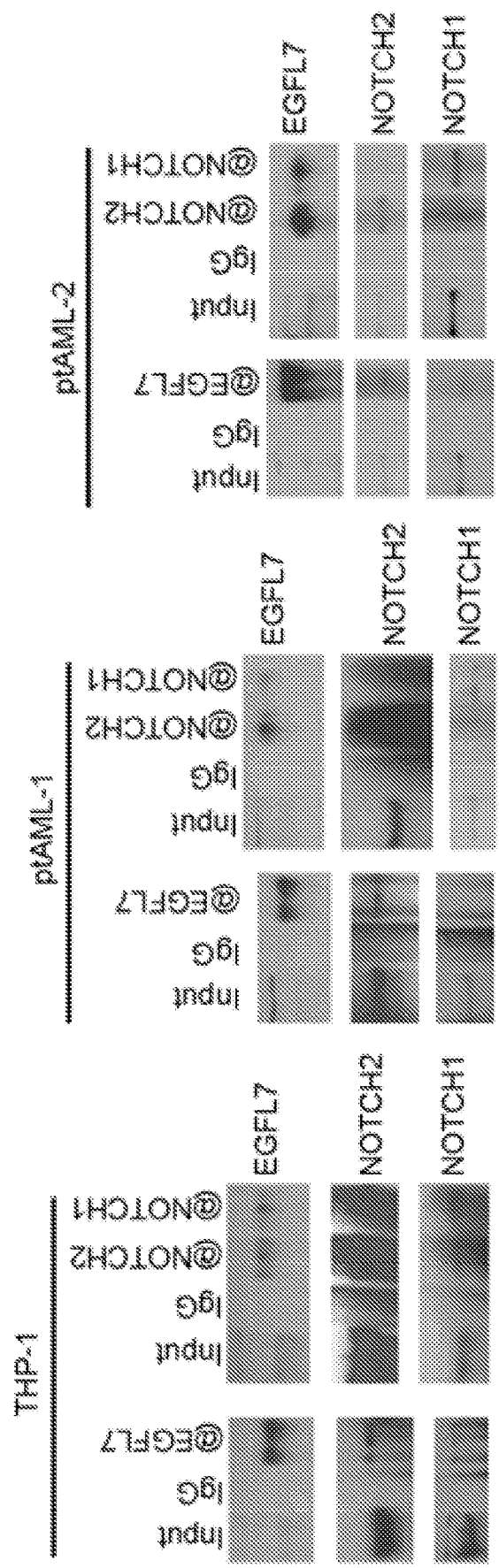
FIG. 22. EGFL7 protein interacts with NOTCH1 and NOTCH2 in human AML cells. Cell lysate of $10 \times 10^6$ THP-1 cells or $5 \times 10^6$ human AML patient blasts (n=2) were subjected to CO-IP with Protein G Plus/Protein A agarose beads. The elute was analyzed by immunoblotting of EGFL7, NOTCH1 and NOTCH2 with the corresponding antibodies.

In the examples above, it was demonstrated that EGFL7 is upregulated in primary AML blasts and that high EGFL7 mRNA expression correlates with poor outcome for AML patients. However, the mechanism by which EGFL7 contributes to leukemogenesis is unknown. In order to obtain insights about potential mechanisms by which EGLF7 stimulates AML blast growth, potential EGFL7 interacting proteins were identified. Since other members of the EGFL family of proteins are known to have numerous potential binding partners[13, 22-24] an unbiased high-throughput approach was undertaken by performing an antibody (Ab) interaction array. These arrays have ~400 antibodies hybridized to a membrane. Protein lysates from AML blasts were first incubated with rEGFL7 protein and then spotted onto the antibody membranes. Then using an anti-EGFL7-HRP or anti-GST-HRP control antibody (FIG. 14), the membranes were developed and densitometry of the individual spots were determined for both the anti-EGFL7 and anti-GST-HRP control blots. Array data were then log 2 transformed and normalized by subtracting the mean of the background. Subsequently, a linear mixed model was used for analysis to compare the protein level between anti-EGFL7 Ab array and anti-GST Ab array. Using this strategy, it was found that NOTCH1 was bound significantly to EGFL7 in all three samples (P=1.11E-06). Next, the screening results were validated by assessing direct binding between EGFL7 and NOTCH receptors in both AML cell line and patient blasts. Using the THP-1 cell line that expresses EGFL7 and NOTCH receptors but not concomitant NOTCH activation[10], co-immunoprecipitation (co-IP) assays were performed using an anti-EGFL7 antibody to pull down EGFL7 containing protein complexes. Western blotting was then performed to determine protein interactions using anti-NOTCH1, 2, 3 antibodies. It was found physical association of EGFL7 with the NOTCH 1 and 2 proteins. Conversely, in the pull-down using anti-NOTCH1 or NOTCH2 antibody, it was found that both NOTCH1 and NOTCH2 could be co-immunoprecipitated as part of a complex with EGFL7 (FIG. 22). These results were also confirmed in primary AML patient samples (FIG. 22). Altogether, these data demonstrate the direct interaction of EGFL7 with NOTCH receptors on primary AML blasts.

EGFL7 Suppresses NOTCH Signaling in AML Cells

Figure 23A:
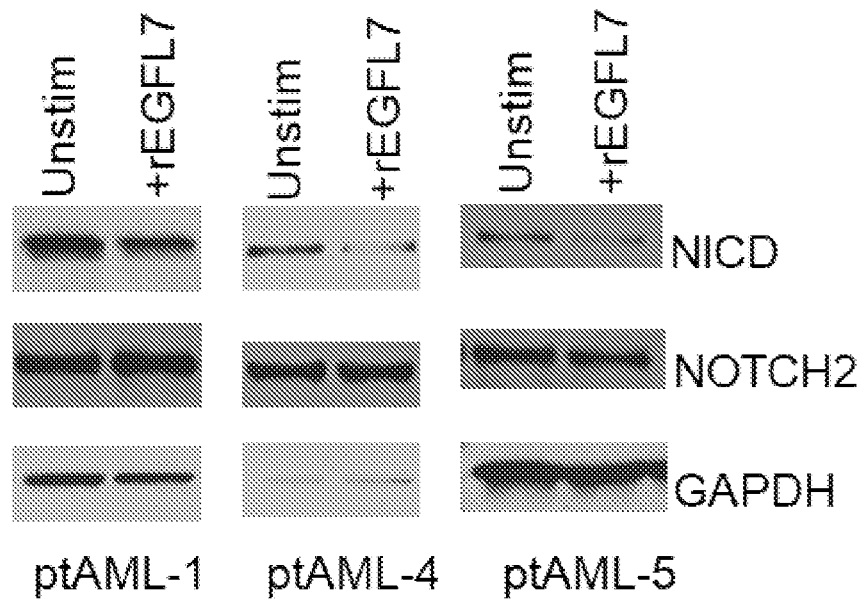
FIG. 23A-23E. EGFL7 suppresses NOTCH signaling in human AML patient blasts.
Figure 23B:
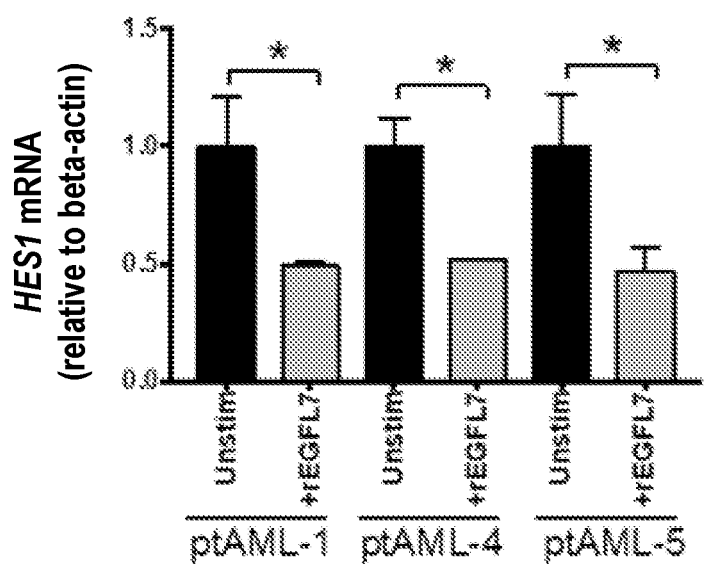
Figure 23C:
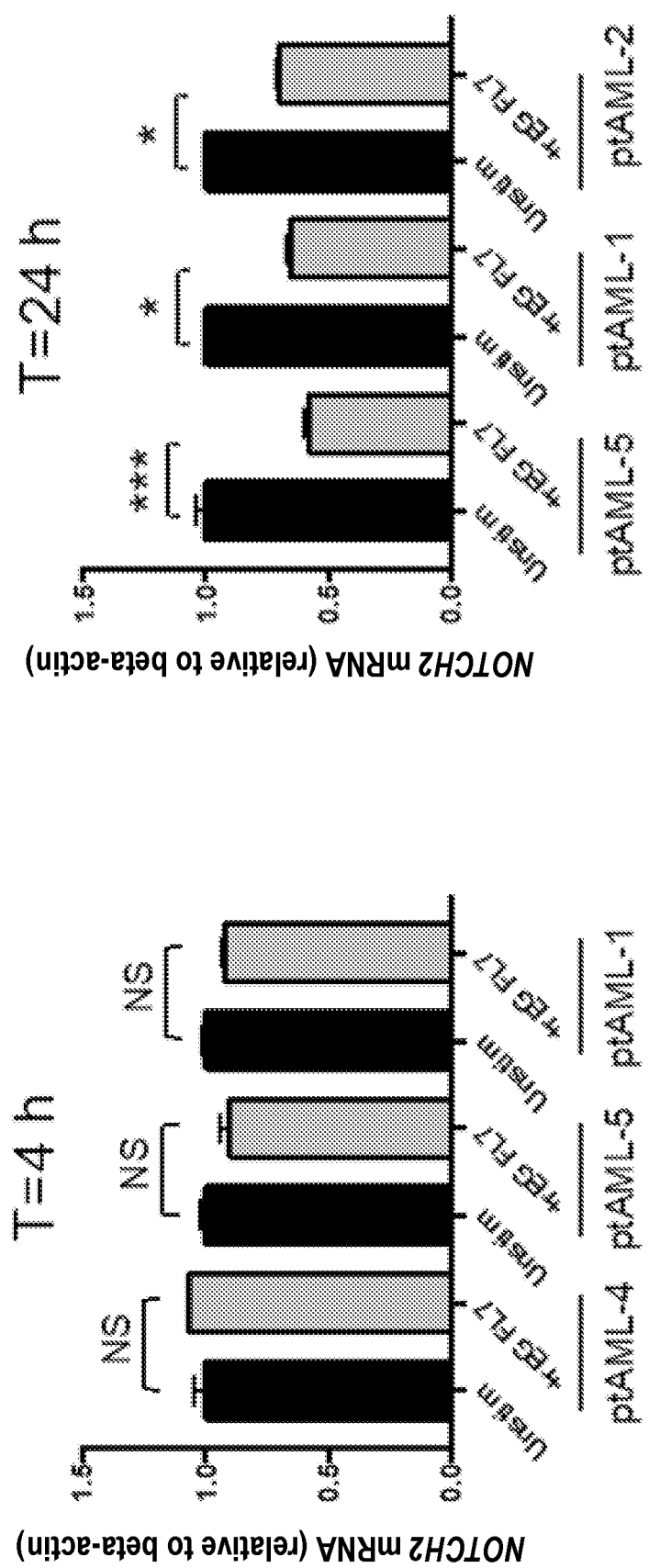
Figure 23D:
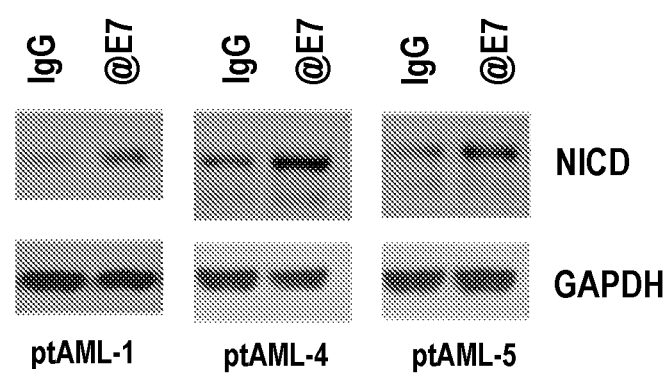
Figure 23E:
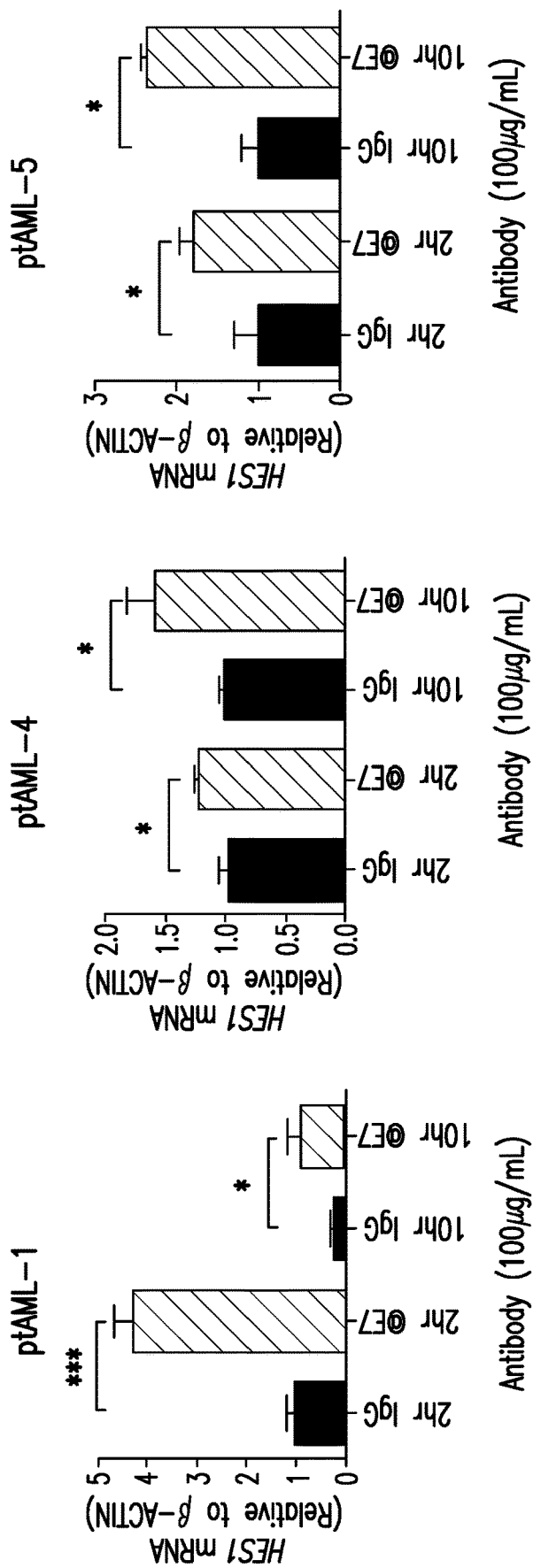
Figure 26:
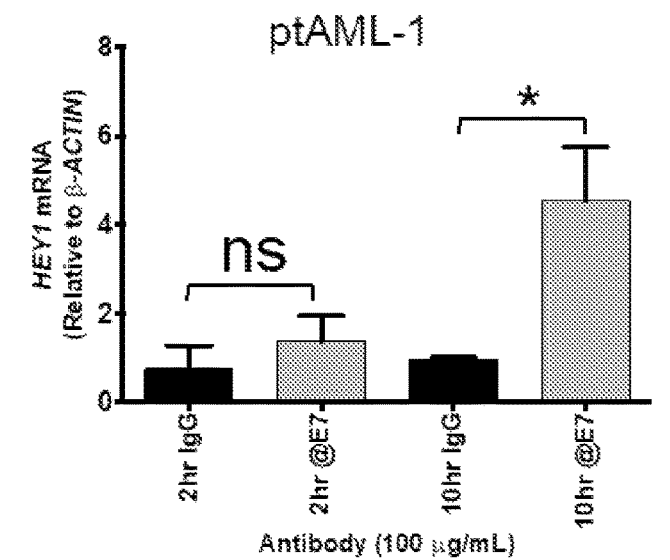
FIG. 26. Blocking EGFL7 increases the NOTCH downstream target, HEY1, in human AML patient blasts (A) Primary blasts from AML patients were cultured in SFEM medium with 10% FBS in the absence or presence of 100 µg/ml of IgG or anti-human EGFL7 antibody for 2 and 10 h. Total RNAs were extracted for qRT-PCR analysis of HEY1 mRNA with β-ACTIN as internal control. $*p<0.05$, $***p<0.001$ vs IgG; ns=not significant.
Figure 26:
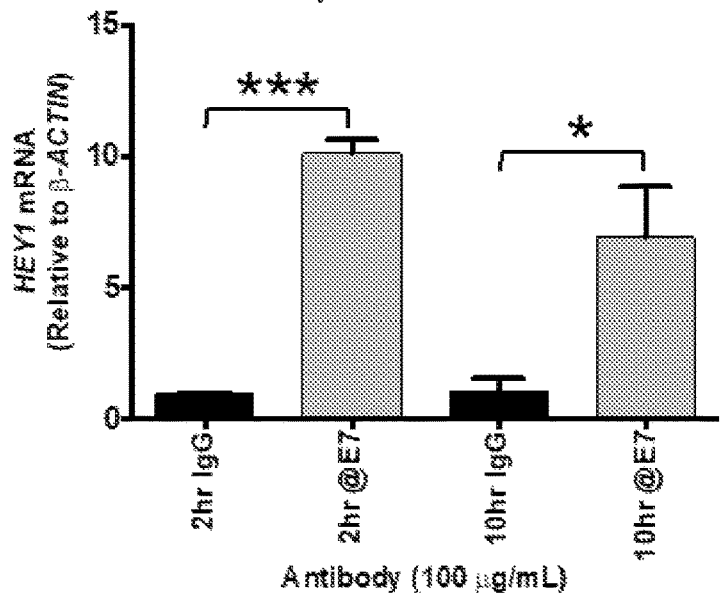

To determine whether EGFL7 binding of NOTCH results in alterations of NOTCH signaling in AML patient blasts, the levels of the NOTCH intracellular cleavage product (NICD) produced in response to rEGFL7 stimulation of primary AML patient samples were investigated. Stimulation with rEGFL7 resulted in significant reductions in the levels of activated NOTCH2 (NICD) but not total NOTCH2 protein in primary human AML samples, indicating that EGFL7 inhibits NOTCH activation (FIG. 23A). To test whether EGFL7-mediated down regulation of NOTCH activity (NICD) results in decreased expression of NOTCH2 downstream target genes, one of the best characterized NOTCH target genes, HEST, was assessed. Primary AML patient samples were stimulated with rEGFL7 resulting in decreased levels of HEST mRNA levels in primary AML blasts (n=3, FIG. 23B). Interestingly at 4 hrs post-rEGFL7 stimulation it was found no changes in NOTCH2 mRNA, however, significant decreases in NOTCH2 transcription was found at 24 hrs post stimulation (FIG. 23C), indicating a potential negative feedback loop involving EGFL7 and NOTCH2 transcriptional down regulation. Next, it was examined whether NOTCH reactivation could be achieved by blocking EGFL7. Activated NICD levels were measured 2 hrs post-stimulation with anti-EGFL7 and significant increases in NICD levels in primary human AML samples were found (n=3, FIG. 23D). It was also found that there were concomitant increases in the expression of HES1 at 2 and 10 hrs post anti-EGFL7 treatment (FIG. 23E). In addition, increases were also observed in a second well-known NOTCH target, HEY1 mRNA. (FIG. 26). Altogether these data support the role of EGFL7 in blocking NOTCH activation in primary AML blasts.

EGFL7 Prevents NOTCH Ligand Induced NOTCH Signaling Activation in AML Cells

Figure 24A:
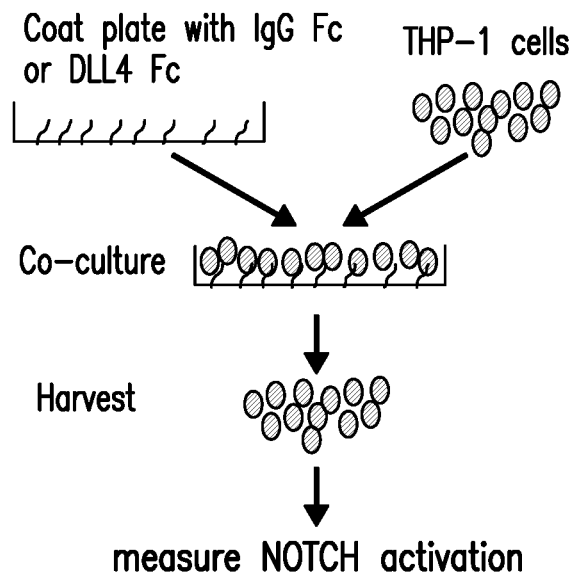
FIG. 24A-24G. EGFL7 prevents activation of NOTCH signaling in AML cells.
Figure 24B:
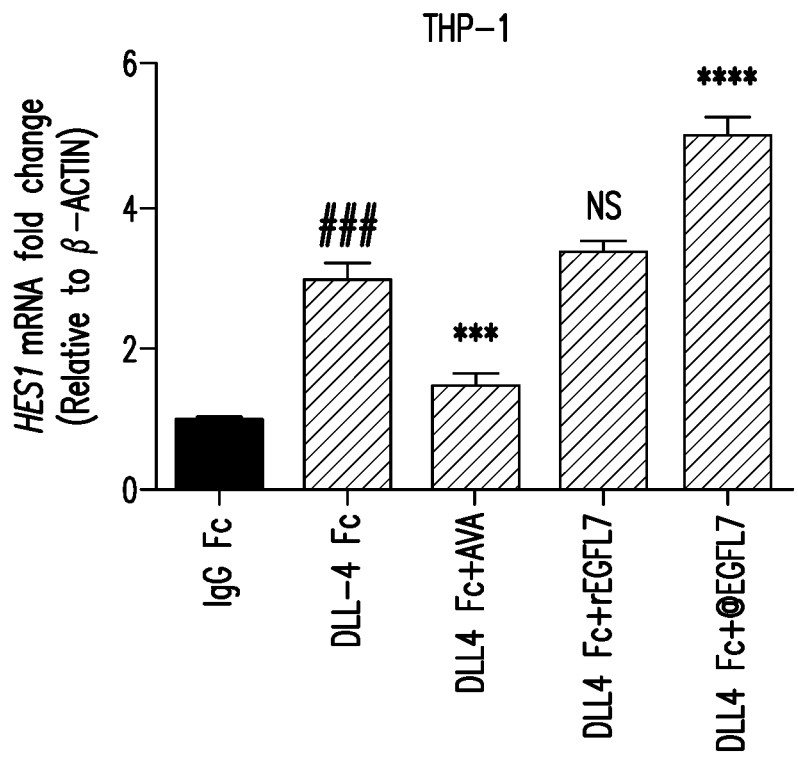
Figure 27:
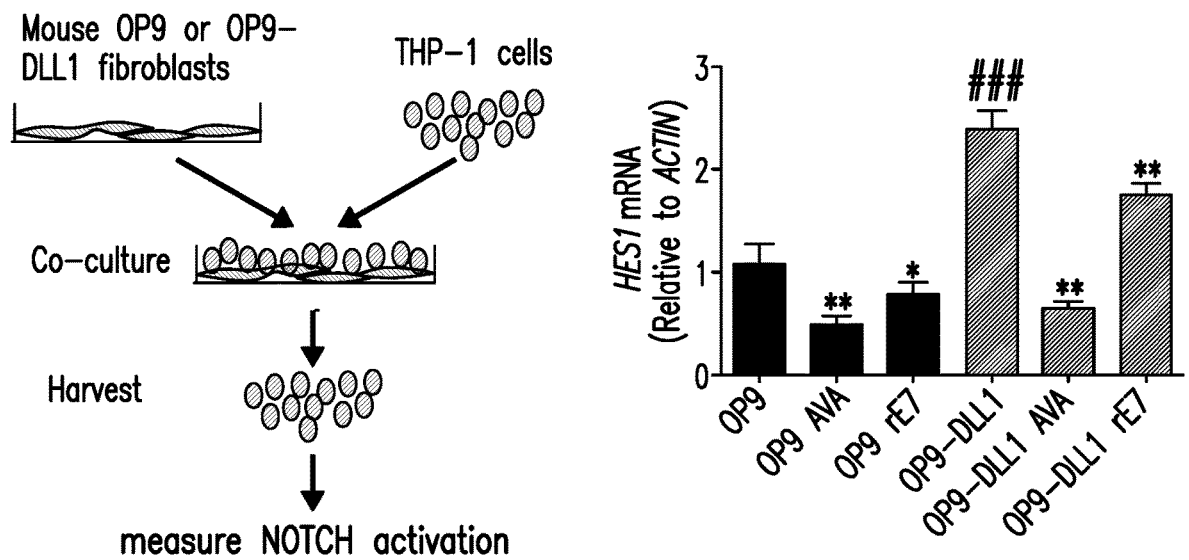
FIG. 27. EGFL7 prevents NOTCH ligand inactivation of Notch signaling in AML cells. (A) Overview of experiments involving co-culture of THP-1 cells with mouse stromal cells overexpressing DLL1. (B) Total RNA was extracted for RT-PCR analysis of HES1 with β-ACTIN as internal control. $\#\#\#\#P<0.001$ OP9-DLL1 vs OP9; $*P<0.05$, $**P<0.01$ vs untreated control.
Figure 28:
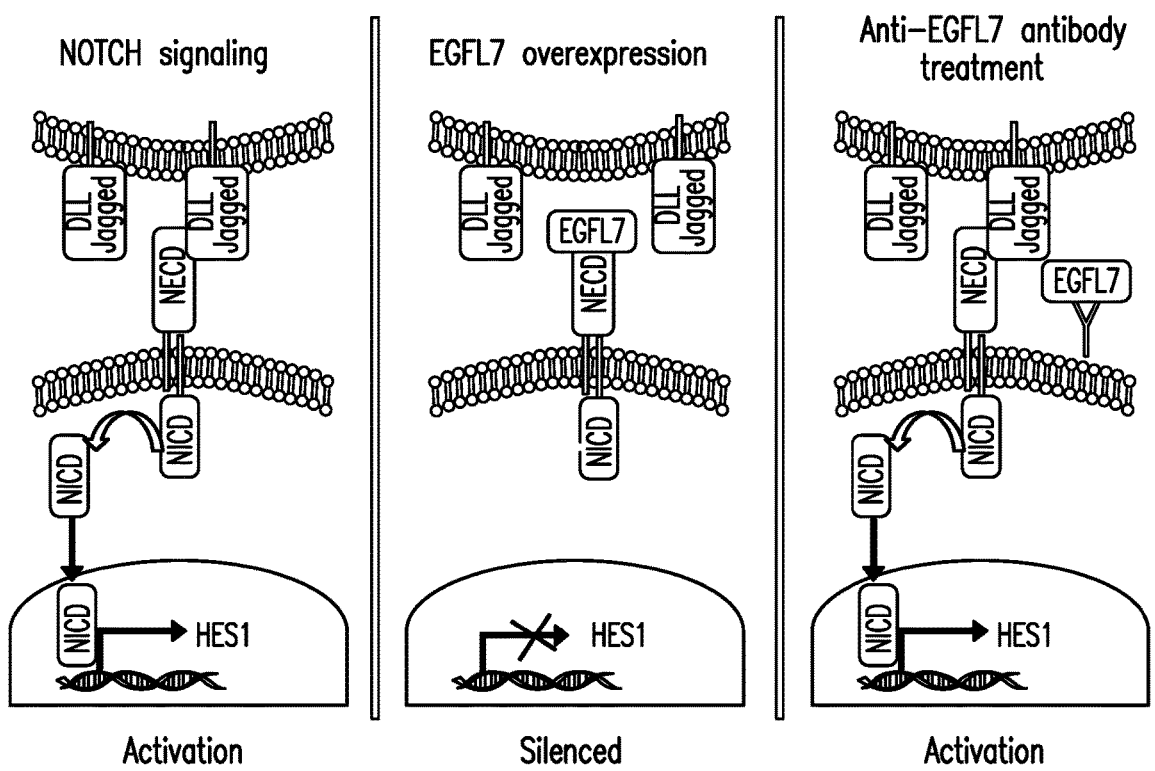
FIG. 28. Schematic model of the biology and therapeutic significance of EGFL7 regulation of NOTCH signaling in AML.

It was next determined whether EGFL7 is inhibiting NOTCH signaling in AML cells by competing with canonical NOTCH ligand binding. To perform these experiments, THP-1 cells were cultured on DLL4-Fc and IgG-Fc (control) coated plates to activate NOTCH signaling. The effect of rEGFL7 and anti-EGFL7 on this DLL4-Fc NOTCH activation was also tested (FIG. 24A). It was found that DLL4-Fc resulted in increases in NOTCH activation assessed by HES1 expression. Addition of rEGFL7 or γ-secretase inhibitor (AVA) significantly reduced DLL4-Fc-mediated NOTCH activation, while addition of anti-EGFL7 blocking antibody enhanced DLL4-Fc-mediated NOTCH activation (FIG. 24B). To validate these results, another well-known NOTCH ligand DLL1 was used. For these experiments, co-culture was performed of THP-1 cells with stromal cells (OP9) overexpressing membrane bound DLL1 (OP9-DLL1)[25] (FIG. 27A). It was found that similar to DLL4-FC, THP-1 cells co-cultured with OP9-DLL1, also resulted in significant increases in NOTCH activation assessed by HES1 expression (FIG. 27B, OP9 vs OP9-DLL1, p<0.05). Addition of rEGFL7 or AVA significantly reduced DLL1-mediated NOTCH activation (FIG. 27B, OP9-DLL1 vs. OP9-DLL1+rE7, p<0.05).

Figure 24C:
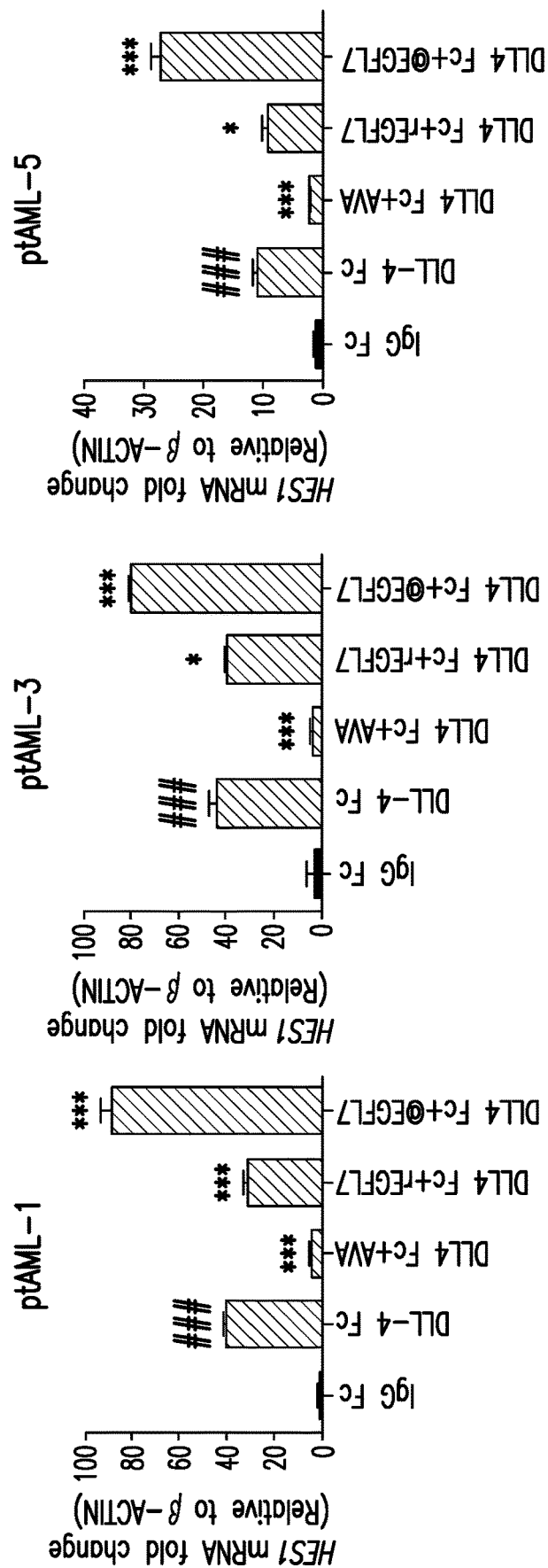
Figure 24D:
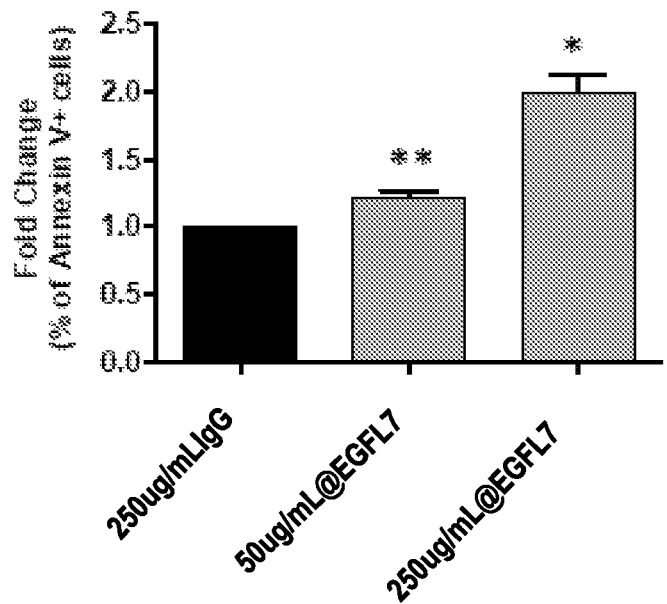
Figure 24E:
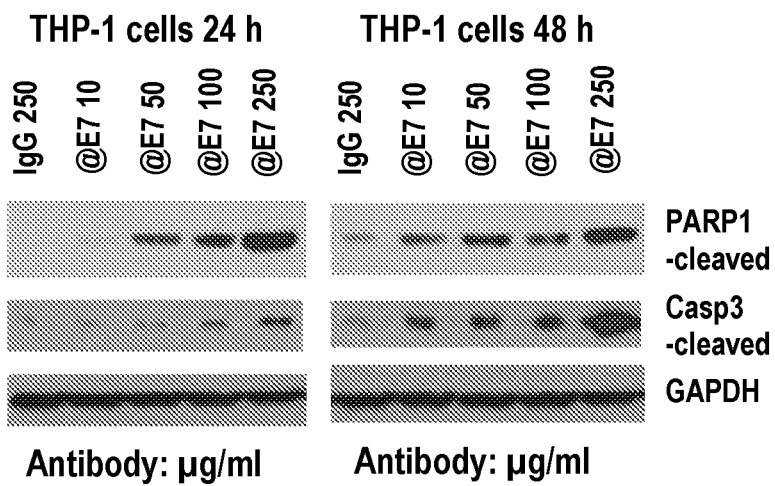
Figure 24F:
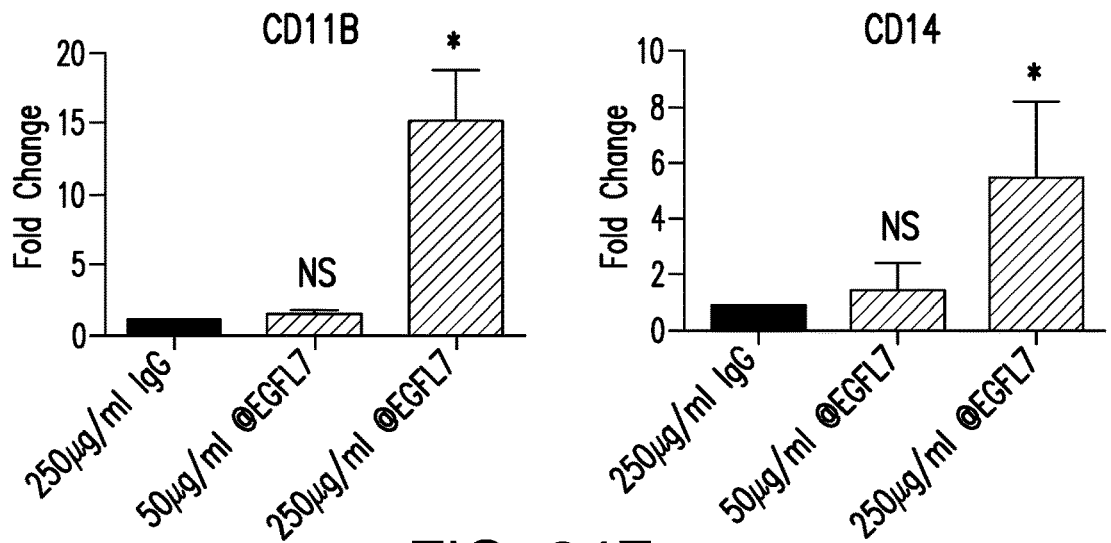
Figure 24G:
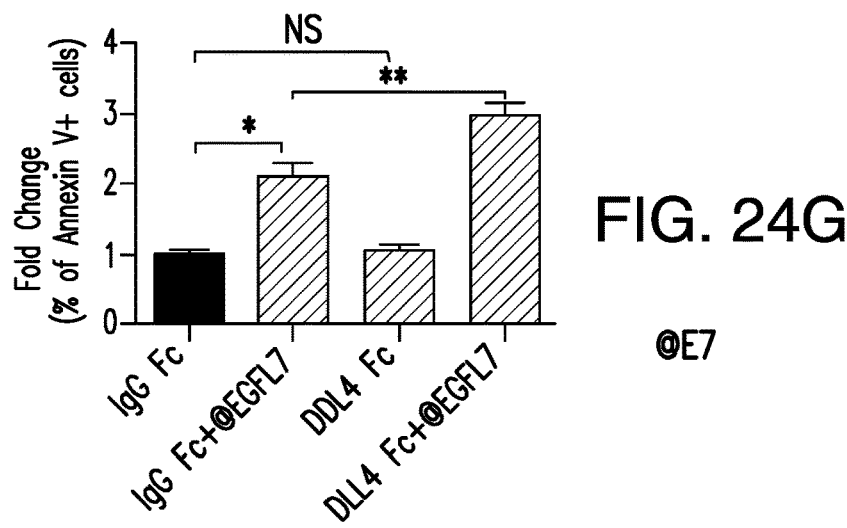

As described in the examples above, anti-EGFL7 treatment of AML cells resulted in decreased blast growth and survival. To determine whether reactivation of NOTCH in AML cells leads to leukemic cell differentiation and survival, THP-1 cells were treated with anti-EGFL7 and apoptosis and differentiation were measured. An increase in AnnexinV+ was observed in apoptotic cells after anti-EGFL7 treatment (FIG. 24C). These findings were supported by western blots demonstrating an increase in PARP1 and CASP3 cleavage as a result of anti-EGFL7 treatment (FIG. 24D). To determine whether anti-EGFL7 also results in cell differentiation of THP-1 cells, the levels of CD11B and CD14 expression were measured and increases were found in both these markers at 96-hours post anti-EGFL7 treatment (FIG. 24E-F). To determine whether blocking EGFL7 and subsequent activation by DLL4 results in enhanced cell death of AML cells, THP-1 cells were cultured in Parsatuzumab followed by NOTCH activation using DLL4-Fc or IgG-Fc control. Significant increases in apoptosis were observed in THP-1 cells treated with anti-EGFL7+DLL4-Fc compared to both DLL4-Fc or anti-EGFL7 alone. In summary, these data demonstrate the ability of EGFL7 to block key NOTCH ligand binding. EGFL7 binding results in inhibition of canonical NOTCH signaling, this inhibition is reversible in AML, and can be re-activated by blocking EGFL7 with a monoclonal antibody.

Figure 25A:
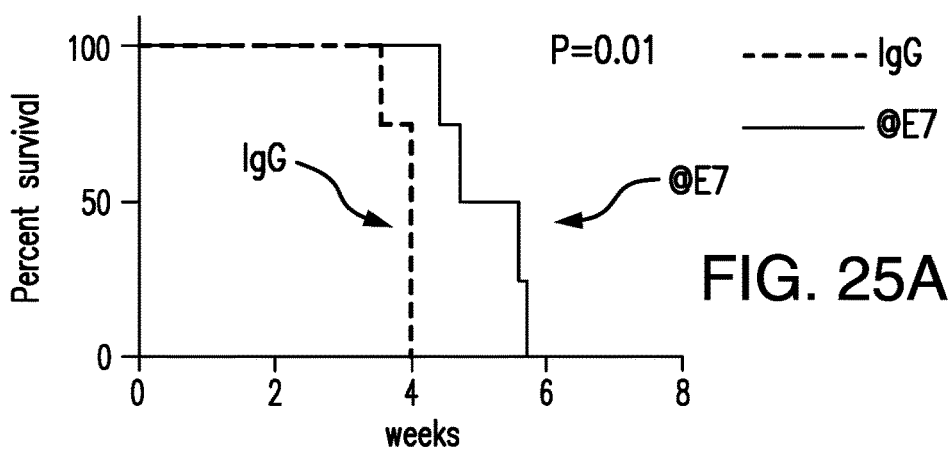
FIG. 25A-25B. Anti-EGFL7 antibody prolongs survival in an AML mouse xenograft model.
Figure 25B:
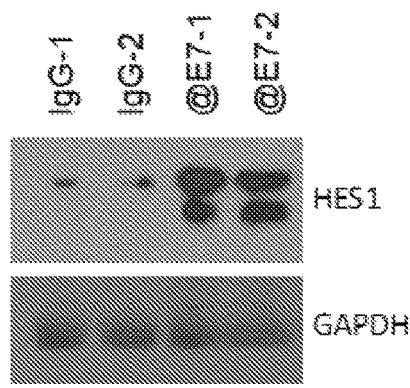

Anti-EGFL7 Antibody Activates Notch Signaling In Vivo and Prolongs Survival in an AML Xenograft Mouse Model To extend these observations in vivo, an EOL-1 xenograft AML model was used. As shown in the examples above, EOL-1 cells are sensitive to anti-EGFL7 treatment and this leads to substantial cell death and differentiation. Briefly, 10×10^6 EOL-1 cells were transplanted into non-conditioned NSG recipient mice. Two weeks post-transplantation, mice were treated with 50 mpk of anti-EGFL7 or IgG1 control antibody three times per week (FIG. 25A). It was found that treatment with anti-EGFL7 prolonged survival compared to IgG1 controls (FIG. 25B). Furthermore, it was found that in vivo treatment results in reactivation of NOTCH signaling and increased levels of HES1 protein via western blots in the anti-EGFL7 treated mice compared to IgG1 controls (FIG. 25C). Overall, these results demonstrate that EGFL7 targeted therapy leads to NOTCH reactivation in vivo, and represents a novel therapy for patients with AML.

Discussion

EGFL7 is a protein normally secreted by endothelial cells to promote cell growth and migration[13, 18, 26-28]. Several tissues express EGFL7 at low levels but expression can be induced in response to hypoxia, angiogenesis, and vasculature injury[12, 24, 29]. The Egfl7:eGFP transgenic mouse reporter strain demonstrated that Egfl7 expression highly correlated with active sites of angiogenesis[12]. Recently, the role of EGFL7 overexpression has been shown to be clinically important and correlates with tumor grade in many solid tumors such as: laryngeal squamous cell carcinoma, malignant glioma, breast, and hepatocellular[30, 31] In many cases the mechanism of EGFL7-mediated tumorigenesis is thought to involve EGFL7's role to induce vessel formation through regulation of endothelial cell proliferation, survival, and/or migration[13, 18] In the previous examples above, a role for EGFL7 in acute myeloid leukemia (AML) was described. It was found that levels of both EGFL7 mRNA and protein were increased in blasts of patients with acute myeloid leukemia (AML) compared with normal BM cells (NBM). High EGFL7 mRNA expression associated with lower complete remission rates, shorter event-free and shorter overall survival in older (aged ≥60 years) and younger (aged <60 years) patients with cytogenetically normal AML. It was further shown that AML blasts secrete EGFL7 protein, and that increased levels of EGFL7 protein are found in the sera from AML patients compared with sera from healthy controls. Treatment of patient AML blasts with recombinant EGFL7 (rEGFL7) in vitro leads to increases in leukemic blast cell growth. However, the molecular mechanisms underlying EGFL7 induced leukemogenesis has not been fully elucidated. In the example here, it was demonstrated that EGFL7 is able to directly bind multiple proteins on primary AML blasts, including NOTCH. Although EGFL7 has been shown to bind NOTCH in non-hematopoietic cells, whether this binding results in NOTCH activation or repression has been demonstrated to be cell type specific, and has not been determined in AML cells[13, 18].

NOTCH signaling has been shown to be important for normal hematopoiesis and oncogenic activation of NOTCH signaling has been shown to contribute to leukemogenesis in T-ALL[32-36]. However, there is still uncertainty when it comes to the exact role of NOTCH in different hematopoietic compartments. Previously, other groups have shown that the NOTCH signaling pathway is silenced in AML and that re-expression leads to disease elimination, however the mechanism underlying this NOTCH inactivation has remained unknown[9-11]. Feasibly, decreased NOTCH activation could be the result of decreased levels of NOTCH ligands, insufficient levels of NOTCH receptor expression, or inadequate cleavage and/or translocation of NOTCH-IC to the nucleus to activate target gene transcription. Here, one possible mechanism by which the NOTCH pathway remains inactive in AML is through antagonism of normal NOTCH ligand binding to NOTCH receptors on leukemic blasts. However, antagonism of NOTCH2 by EGFL7 binding might not be the only mechanism involving EGFL7-mediated silencing of NOTCH signaling. It was found that in response to EGFL7 stimulation, primary AML blasts had decreased cleavage of NOTCH2 at 4 hours post stimulation. At this early time point, it was shown there are no differences in total NOTCH2 protein or NOTCH2 mRNA. Interestingly, at 24 hours post stimulation, significant decreases in the levels of NOTCH2 mRNA were found. These results show that EGFL7 binding to the NOTCH receptor may also lead to long-term transcriptional repression of NOTCH2, creating a negative feedback loop involving EGFL7, NOTCH signaling inactivation, and NOTCH transcriptional repression. The exact mechanism by which EGFL7 stimulation leads to transcriptional repression of NOTCH2 mRNA is currently unknown, but future studies to determine how this is regulated could provide novel insights into NOTCH gene regulation.

Although the interaction of EGFL7 with such a critical signaling pathway such as NOTCH is important for understanding the cross regulation of these pathways in AML, the results from the antibody array demonstrates the ability for EGFL7 to bind many proteins important for regulating diverse biological processes. Therefore, it seems likely that EGFL7 is functioning in many different signaling pathways important for AML.

Taken together, these data show that targeting EGFL7 is a novel therapeutic target in AML, and that blocking EGFL7 binding with a monoclonal antibody can interfere with the regulation of multiple signaling pathways important for disease pathogenesis.

REFERENCES CITED IN THIS EXAMPLE

1. Heidel F H, Arreba-Tutusaus P, Armstrong S A, Fischer T. Evolutionarily conserved signaling pathways: acting in the shadows of acute myelogenous leukemia's genetic diversity. *Clin Cancer Res* 2015 Jan. 15; 21(2): 240-248.
2. Briot A, Bouloumie A, Iruela-Arispe M L. Notch, lipids, and endothelial cells. *Curr Opin Lipidol* 2016 Jul. 22.
3. D'Souza B, Meloty-Kapella L, Weinmaster G. Canonical and non-canonical Notch ligands. *Curr Top Dev Biol* 2010; 92: 73-129.
4. Acar A, Simoes B M, Clarke R B, Brennan K. A Role for Notch Signalling in Breast Cancer and Endocrine Resistance. *Stem Cells Int* 2016; 2016: 2498764.
5. Lu J, Xia Y, Chen K, Zheng Y, Wang J, Lu W, et al. Oncogenic role of the Notch pathway in primary liver cancer. *Oncol Lett* 2016 July; 12(1): 3-10.
6. Lobry C, Oh P, Mansour M R, Look A T, Aifantis I. Notch signaling: switching an oncogene to a tumor suppressor. *Blood* 2014 Apr. 17; 123(16): 2451-2459.
7. Ntziachristos P, Lim J S, Sage J, Aifantis I. From fly wings to targeted cancer therapies: a centennial for notch signaling. *Cancer Cell* 2014 Mar. 17; 25(3): 318-334.
8. Oh P, Lobry C, Gao J, Tikhonova A, Loizou E, Manet J, et al. In vivo mapping of notch pathway activity in normal and stress hematopoiesis. *Cell Stem Cell* 2013 Aug. 1; 13(2): 190-204.
9. Kannan S, Sutphin R M, Hall M G, Golfman L S, Fang W, Nolo R M, et al. Notch activation inhibits AML growth and survival: a potential therapeutic approach. *J Exp Med* 2013 Feb. 11; 210(2): 321-337.
10. Lobry C, Ntziachristos P, Ndiaye-Lobry D, Oh P, Cimmino L, Zhu N, et al. Notch pathway activation targets 10. AML-initiating cell homeostasis and differentiation. *J Exp Med* 2013 Feb. 11; 210(2): 301-319.
11. Kato T, Sakata-Yanagimoto M, Nishikii H, Ueno M, Miyake Y, Yokoyama Y, et al. Hes1 suppresses acute myeloid leukemia development through FLT3 repression. *Leukemia* 2015 March; 29(3): 576-585.
12. Bambino K, Lacko L A, Hajjar K A, Stuhlmann H. Epidermal growth factor-like domain 7 is a marker of the endothelial lineage and active angiogenesis. *Genesis* 2014 July; 52(7): 657-670.
13. Nichol D, Stuhlmann H. EGFL7: a unique angiogenic signaling factor in vascular development and disease. *Blood* 2012 Feb. 9; 119(6): 1345-1352.
14. Oh J, Park S H, Lee T S, Oh H K, Choi J H, Choi Y S. High expression of epidermal growth factor-like domain 7 is correlated with poor differentiation and poor prognosis in patients with epithelial ovarian cancer. *J Gynecol Oncol* 2014 October; 25(4): 334-341.
15. Fan C, Yang L Y, Wu F, Tao Y M, Liu L S, Zhang J F, et al. The expression of Egfl7 in human normal tissues and epithelial tumors. *Int J Blot Markers* 2013 January-March; 28(1): 71-83.
16. Papaioannou D, Shen C, Nicolet D, McNeil B, Bill M, Karunasiri M, et al. Prognostic and biological significance of the proangiogenic factor EGFL7 in acute myeloid leukemia. *Proc Natl Acad Sci USA* 2017 Jun. 6; 114(23): E4641-E4647.
17. Badiwala M V, Guha D, Tumiati L, Joseph J, Ghashghai A, Ross H J, et al. Epidermal growth factor-like domain 7 is a novel inhibitor of neutrophil adhesion to coronary artery endothelial cells injured by calcineurin inhibition. *Circulation* 2011 Sep. 13; 124(11 Suppl): S197-203.
18. Nichol D, Shawber C, Fitch M J, Bambino K, Sharma A, Kitajewski J, et al. Impaired angiogenesis and altered Notch signaling in mice overexpressing endothelial Egfl7. *Blood* 2010 Dec. 23; 116(26): 6133-6143.
19. Schmidt M H, Bicker F, Nikolic I, Meister J, Babuke T, Picuric S, et al. Epidermal growth factor-like domain 7 (EGFL7) modulates Notch signalling and affects neural stem cell renewal. *Nat Cell Biol* 2009 July; 11(7): 873-880.
20. Massimiani M, Vecchione L, Piccirilli D, Spitalieri P, Amati F, Salvi S, et al. Epidermal growth factor-like domain 7 promotes migration and invasion of human trophoblast cells through activation of MAPK, PI3K and NOTCH signaling pathways. *Mol Hum Reprod* 2015 May; 21(5): 435-451.
21. Dorrance A M, De Vita S, Radu M, Reddy P N, McGuinness M K, Harris C E, et al. The Rac GTPase effector p21-activated kinase is essential for hematopoietic stem/progenitor cell migration and engraftment. *Blood* 2013 Mar. 28; 121(13): 2474-2482.
22. Nikolic I, Stankovic N D, Bicker F, Meister J, Braun H, Awwad K, et al. EGFL7 ligates alphavbeta3 integrin to enhance vessel formation. *Blood* 2013 Apr. 11; 121(15): 3041-3050.
23. Renz M, Otten C, Faurobert E, Rudolph F, Zhu Y, Boulday G, et al. Regulation of beta1 integrin-Klf2-mediated angiogenesis by CCM proteins. *Dev Cell* 2015 Jan. 26; 32(2): 181-190.
24. Badiwala M V, Tumiati L C, Joseph J M, Sheshgiri R, Ross H J, Delgado D H, et al. Epidermal growth factor-like domain 7 suppresses intercellular adhesion molecule 1 expression in response to hypoxia/reoxygenation injury in human coronary artery endothelial cells. *Circulation* 2010 Sep. 14; 122(11 Suppl): S156-161.
25. Schmitt T M, de Pooter R F, Gronski M A, Cho S K, Ohashi P S, Zuniga-Pflucker J C. Induction of T cell development and establishment of T cell competence from embryonic stem cells differentiated in vitro. *Nat Immunol* 2004 April; 5(4): 410-417.
26. Luo B H, Xiong F, Wang J P, Li J H, Zhong M, Liu Q L, et al. Epidermal growth factor-like domain-containing protein 7 (EGFL7) enhances EGF receptor-AKT signaling, epithelial-mesenchymal transition, and metastasis of gastric cancer cells. *PLoS One* 2014; 9(6): e99922.
27. Shen X, Han Y, Xue X, Li W, Guo X, Li P, et al. Epidermal growth factor-like domain 7 promotes cell invasion and angiogenesis in pancreatic carcinoma. *Biomed Pharmacother* 2016 February; 77: 167-175.
28. Wang X X, Yao X B, Qiang Z S, Zhu H L. Attenuation of EGFL7 inhibits human laryngocarcinoma cells growth and invasion. *Int J Clin Exp Med* 2015; 8(3): 3141-3155.
29. Johnson L, Huseni M, Smyczek T, Lima A, Yeung S, Cheng J H, et al. Anti-EGFL7 antibodies enhance stress-induced endothelial cell death and anti-VEGF efficacy. *J Clin Invest* 2013 September; 123(9): 3997-4009.
30. Li J J, Yang X M, Wang S H, Tang Q L. Prognostic role of epidermal growth factor-like domain 7 protein expression in laryngeal squamous cell carcinoma. *J Laryngol Otol* 2011 November; 125(11): 1152-1157.
31. Huang C H, Li X J, Zhou Y Z, Luo Y, Li C, Yuan X R. Expression and clinical significance of EGFL7 in malignant glioma. *J Cancer Res Clin Oncol* 2010 November; 136(11): 1737-1743.
32. Hannon M M, Lohan F, Erbilgin Y, Sayitoglu M, O'Hagan K, Mills K, et al. Elevated TRIB2 with NOTCH1 activation in paediatric/adult T-ALL. *Br J Haematol* 2012 September; 158(5): 626-634.
33. Wang W, Zimmerman G, Huang X, Yu S, Myers J, Wang Y, et al. Aberrant Notch Signaling in the Bone Marrow Microenvironment of Acute Lymphoid Leukemia Suppresses Osteoblast-Mediated Support of Hematopoietic Niche Function. *Cancer Res* 2016 Mar. 15; 76(6): 1641-1652.
34. Stein S J, Mack E A, Rome K S, Pajcini K V, Ohtani T, Xu L, et al. Trib2 Suppresses Tumor Initiation in Notch-Driven T-ALL. *PLoS One* 2016; 11(5): e0155408.
35. Suresh S, Irvine A E. The NOTCH signaling pathway in normal and malignant blood cell production. *J Cell Commun Signal* 2015 March; 9(1): 5-13.
36. He Q, Zhang C, Wang L, Zhang P, Ma D, Lv J, et al. Inflammatory signaling regulates hematopoietic stem and progenitor cell emergence in vertebrates. *Blood* 2015 Feb. 12; 125(7): 1098-1106.

```
EGFL7 SEQUENCES
Human EGFL7 gene sequence (SEQ ID NO: 1):
ACCESSION NM_016215
GCACCAAGCT GGCCCTGCAC GGCTGCAAGG GAGGCTCCTG

TGGACAGGCC AGGCAGGTGG GCCTCAGGAG GTGCCTCCAG

GCGGCCACTG GGCCTGAGGC CCCAGCAAGG GCTAGGGTCC

ATCTCCAGTC CCAGGACACA GCAGCGGCCA CCATGGCCAC

GCCTGGGCTC CAGCAGCATC AGAGCAGCCC CTGTGGTTGG

CAGCAAAGTT CAGCTTGGCT GGGCCCGCTG TGAGGGGCTT

CGCGCTACGC CCTGCGGTGT CCCGAGGGCT GAGGTCTCCT

CATCTTCTCC
```

```
CTAGCAGTGG ATGAGCAACC CAACGGGGGC CCGGGGAGGG

GAACTGGCCC CGAGGGAGAG GAACCCCAAA GCCACATCTG

TAGCCAGGAT GAGCAGTGTG AATCCAGGCA GCCCCCAGGA

CCGGGGAGGC ACAGGTGGCC CCCACCACCC GGAGGAGCAG

CTCCTGCCCC TGTCCGGGGG ATGACTGATT CTCCTCCGCC

AGGCCACCCA GAGGAGAAGG CCACCCCGCC TGGAGGCACA

GGCCATGAGG GGCTCTCAGG AGGTGCTGCT GATGTGGCTT

CTGGTGTTGG CAGTGGGCGG CACAGAGCAC GCCTACCGGC

CCGGCCGTAG GGTGTGTGCT GTCCGGGCTC ACGGGGACCC

TGTCTCCGAG TCGTTCGTGC AGCGTGTGTA CCAGCCCTTC

CTCACCACCT GCGACGGGCA CCGGGCCTGC AGCACCTACC

GAACCATCTA TAGGACCGCC TACCGCCGCA GCCCTGGGCT

GGCCCCTGCC AGGCCTCGCT ACGCGTGCTG CCCCGGCTGG

AAGAGGACCA GCGGGCTTCC TGGGGCCTGT GGAGCAGCAA

TATGCCAGCC GCCATGCCGG AACGGAGGGA GCTGTGTCCA

GCCTGGCCGC TGCCGCTGCC CTGCAGGATG GCGGGGTGAC

ACTTGCCAGT CAGATGTGGA TGAATGCAGT GCTAGGAGGG

GCGGCTGTCC CCAGCGCTGC GTCAACACCG CCGGCAGTTA

CTGGTGCCAG TGTTGGGAGG GGCACAGCCT GTCTGCAGAC

GGTACACTCT GTGTGCCCAA GGGAGGGCCC CCAGGGTGG

CCCCCAACCC GACAGGAGTG GACAGTGCAA TGAAGGAAGA

AGTGCAGAGG CTGCAGTCCA GGGTGGACCT GCTGGAGGAG

AAGCTGCAGC TGGTGCTGGC CCCACTGCAC AGCCTGGCCT

CGCAGGCACT GGAGCATGGG CTCCCGGACC CCGGCAGCCT

CCTGGTGCAC TCCTTCCAGC AGCTCGGCCG CATCGACTCC

CTGAGCGAGC AGATTTCCTT CCTGGAGGAG CAGCTGGGGT

CCTGCTCCTG CAAGAAAGAC TCGTGACTGC CCAGCGCCCC

AGGCTGGACT GAGCCCCTCA CGCCGCCCTG CAGCCCCCAT

GCCCCTGCCC AACATGCTGG GGGTCCAGAA ACCACCTCGG

GGTGACTGAG CGGAAGGCCA GGCAGGGCCT TCCTCCTCTT

CCTCCTCCCC TTCCTCGGGA GGCTCCCCAG ACCCTGGCAT

GGGATGGGCT GGGATCTTCT CTGTGAATCC ACCCCTGGCT

ACCCCCACCC TGGCTACCCC AACGGCATCC CAAGGCCAGG

TGGGCCCTCA GCTGAGGGAA GGTACGAGCT CCCTGCTGGA

GCCTGGGACC CATGGCACAG GCCAGGCAGC CCGGAGGCTG

GGTGGGGCCT CAGTGGGGGC TGCTGCCTGA CCCCCAGCAC

AATAAAAATG AAACGTGAAA AAAAAAAAA AAAA
```

Human EGFL7 amino acid sequence (SEQ ID NO: 2):
ACCESSION NP_057299
MRGSQEVLLMWLLVLAVGGTEHAYRPGRRVCAVRAHGDPVSESFVQRVYQ

PFLTTCDGHRACSTYRTIYRTAYRRSPGLAPARRRYACCPGWKRTSGLPG

ACGAAICQPPCRNGGSCVQPGRCRCPAGWRGDTCQSDVDECSARRGGCPQ

RCVNTAGSYWCQCWEGHSLSADGTLCVPKGGPPRVAPNPTGVDSAMKEEV

QRLQSRVDLLEEKLQLVLAPLHSLASQALEHGLPDPGSLLVHSFQQLGRI

DSLSEQISFLEEQLGSCSCKKDS

EGFL7 Domains:
Signal Peptide (1-19) (SEQ ID NO: 3):
MRGSQEVLLMWLLVLAVGG

EMI Domain (27-104) (SEQ ID NO: 4):
GRRVCAVRAHGDPVSESFVQRVYQPFLTTCDGHRACSTYRTIYRTAYRRS

PGLAPARPRYACCPGWKRTSGLPGACGA

EGF/DSL Domain (107-134) (SEQ ID NO: 5):
CQPPCRNGGSCVQPGRCRCPAGWRGDTC

Ca2+ Binding Domain (141-176) (SEQ ID NO: 6):
CSARRGGCPQRCVNTAGSYWCQCWEGHSLSADGTLC In some embodiments, the EGFL7 amino acid sequence is SEQ ID NO:2. In some embodiments, the antibody or antigen-binding fragment thereof specifically binds to SEQ ID NO:2, or a fragment thereof. In some embodiments, the antibody or antigen-binding fragment thereof specifically binds to the amino acid sequence encoded by SEQ ID NO:3, or a fragment thereof. In some embodiments, the antibody or antigen-binding fragment thereof specifically binds to the amino acid sequence encoded by SEQ ID NO:4, or a fragment thereof. In some embodiments, the antibody or antigen-binding fragment thereof specifically binds to the amino acid sequence encoded by SEQ ID NO:5, or a fragment thereof. In some embodiments, the antibody or antigen-binding fragment thereof specifically binds to the amino acid sequence encoded by SEQ ID NO:6, or a fragment thereof. In some embodiments, the EGFL7 amino acid sequence is at least 60% (for example, at least 60%, at least 65%, at least 70%, at least 75%, at least 80%, at least 85%, at least 90%, at least 95%, at least 99%) identical to SEQ ID NO:2, SEQ ID NO:3, SEQ ID NO:4, SEQ ID NO:5, SEQ ID NO:6, or a fragment thereof.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for treating acute myeloid leukemia (AML), comprising: administering to a subject in need thereof an effective amount of an antibody or antigen-binding fragment thereof that specifically binds to an EGFL7 polypeptide, wherein the antibody or antigen-binding fragment thereof is parsatuzumab.

2. The method of claim 1, wherein the antibody or antigen-binding fragment thereof is administered in combination with a nanoparticle-antagomiR-126 therapy.

3. The method of claim 1, wherein the antibody or antigen-binding fragment thereof is administered in combination with an additional chemotherapeutic agent.

4. The method of claim 3, wherein the additional chemotherapeutic agent is selected from cytarabine, daunorubicin, idarubicin, mitoxantrone, vincristine, Cladribine, Fludarabine, Topotecan, Etoposide, 6-thioguanine, Hydroxyurea, a Corticosteroid drug, Methotrexate, 6-mercaptopurine, Azacitidine, or Decitabine.

5. The method of claim 3, wherein the additional chemotherapeutic agent is a FLT3 inhibitor.

6. The method of claim 5, wherein the FLT3 inhibitor is gilteritinib.

7. The method of claim 1, wherein the acute myeloid leukemia (AML) is cytogenetically normal acute myeloid leukemia (CN-AML).

8. The method of claim 3, wherein the additional chemotherapeutic agent is a BCL-2 inhibitor.

* * * * *